US 12,156,908 B2

United States Patent
Lee et al.

(10) Patent No.: US 12,156,908 B2
(45) Date of Patent: Dec. 3, 2024

(54) VIRUS LIKE NANOPARTICLE COMPOSITIONS AND METHODS THEREOF

(71) Applicants: Regents of the University of Minnesota, Minneapolis, MN (US); New York Blood Center, Inc., New York, NY (US)

(72) Inventors: Frank Jonathan Lee, Minneapolis, MN (US); Qibin Geng, Minneapolis, MN (US); Jian Shang, Minneapolis, MN (US); Marc Jenkins, Minneapolis, MN (US); Sung-Wook Hong, Minneapolis, MN (US); Lanying Du, New York, NY (US); Wanbo Tai, New York, NY (US); Yushun Wan, Minneapolis, MN (US)

(73) Assignees: Regents of the University of Minnesota, Minneapolis, MN (US); New York Blood Center, Inc., New York, NY (US)

( * ) Notice: Subject to any disclaimer, the term of this patent is extended or adjusted under 35 U.S.C. 154(b) by 266 days.

(21) Appl. No.: 17/361,486

(22) Filed: Jun. 29, 2021

(65) Prior Publication Data

US 2022/0001006 A1    Jan. 6, 2022

Related U.S. Application Data

(60) Provisional application No. 63/047,120, filed on Jul. 1, 2020.

(51) Int. Cl.
| | | |
|---|---|---|
| *A61K 39/12* | (2006.01) | |
| *A61K 39/215* | (2006.01) | |
| *C07K 16/10* | (2006.01) | |
| *C12N 7/00* | (2006.01) | |

(52) U.S. Cl.
CPC ............ *A61K 39/12* (2013.01); *A61K 39/215* (2013.01); *C07K 16/1002* (2023.08); *C07K 16/1003* (2023.08); *C12N 7/00* (2013.01); *C07K 2317/52* (2013.01); *C12N 2770/20023* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 7,888,102 B2 | 2/2011 | Van et al. | |
| 2008/0063664 A1 | 3/2008 | Hsiao et al. | |
| 2019/0328865 A1* | 10/2019 | Du | A61K 39/12 |
| 2023/0146256 A1* | 5/2023 | Lee | C07K 14/005 530/350 |
| 2023/0346916 A1* | 11/2023 | Du | A61K 39/12 |

FOREIGN PATENT DOCUMENTS

| | | |
|---|---|---|
| CN | 1884303 A | 12/2006 |
| WO | 2015164865 A1 | 10/2015 |
| WO | 2018215766 A1 | 11/2018 |
| WO | 2022015668 A1 | 1/2022 |

OTHER PUBLICATIONS

Du L, Zhao G, He Y, Guo Y, Zheng BJ, Jiang S, Zhou Y. Receptor-binding domain of SARS-CoV spike protein induces long-term protective immunity in an animal model. Vaccine. Apr. 12, 2007;25(15):2832-8. doi: 10.1016/j.vaccine.2006.10.031. Epub Oct. 30, 2006. PMID: 17092615. (Year: 2007).*
Geng Q, et al. Novel virus-like nanoparticle vaccine effectively protects animal model from SARS-CoV-2 infection. PLoS Pathog. Sep. 7, 2021;17(9):e1009897. doi: 10.1371/journal.ppat.1009897. PMID: 34492082 . . . (Year: 2021).*
López-Sagaseta J, Malito E, Rappuoli R, Bottomley MJ. Self-assembling protein nanoparticles in the design of vaccines. Comput Struct Biotechnol J. Nov. 26, 2015;14:58-68. doi: 10.1016/j.csbj. 2015.11.001. PMID: 26862374 (Year: 2015).*
Hoffmann, M , et al., "SARS-CoV-2 Cell Entry Depends on ACE2 and TMPRSS2 and Is Blocked by a Clinically Proven Protease Inhibitor", Cell 181 (2), 271-280 (2020).
Jiang, S , et al., "An emerging coronavirus causing pneumonia outbreak in Wuhan, China: calling for developing therapeutic and prophylactic strategies", Emerging Microbes & Infections 9, 275-277 (2020).
Jiang, S , et al., "Receptor-binding domains of spike proteins of emerging or re-emerging viruses as targets for development of antiviral vaccines", Emerg Microbes Infect (8), e13.doi: 10.1038/emi.2012.1, 8 pages (2012).
Joyce, M , et al., "A Cryptic Site of Vulnerability on the Receptor Binding Domain of the SARS-CoV-2 Spike Glycoprotein", bioRxiv preprint doi: https://doi.org/10.1101/2020.03.15.992883, 32 pages (2020).
Ju, B , et al., "Potent human neutralizing antibodies elicited 1 by SARS-CoV-2 infection", bioRxiv preprint doi: https://doi.org/10. 1101/2020.03.21.990770, 42 pages (2020).
Lan, J , et al., "Structure of the SARS-CoV-spike receptor-binding domain bound to the ACE2 receptor", Nature 581, 215-220 (2020).
Li, W , et al., "Identification of sialic acid-binding function for the Middle East respiratory syndrome coronavirus spike glycoprotein", Proc Natl Acad Sci 114 (40), E8508-E8517 (2017).
Li, F , "Structural Analysis of Major Species Barriers between Humans and Palm Civets for Severe Acute Respiratory Syndrome Coronavirus Infections", Journal of Virology 82 (14), 6984-6991 (2008).
Li, F, et al., "Structure of SARS Coronavirus Spike Receptor-Binding Domain Complexed with Receptor", Science 309, 1864-1868 (2005).

(Continued)

*Primary Examiner* — Benjamin P Blumel
*Assistant Examiner* — Jeffrey Mark Sifford
(74) *Attorney, Agent, or Firm* — Viksnins Harris Padys Malen LLP

(57) ABSTRACT

The present disclosure provides virus like nanoparticles (VLPs), which are capable of displaying multiple copies of a SARS-CoV-2 antigen, for eliciting protective immunity against a SARS-CoV-2 infection, as well as polypeptides, compositions and methods thereof.

28 Claims, 12 Drawing Sheets

Specification includes a Sequence Listing.

(56) References Cited

OTHER PUBLICATIONS

Lu, L., et al., "Structure-based discovery of Middle East respiratory syndrome coronavirus fusion inhibitor", Nature Communications 5 (3067), DOI:10.1038/ncomms4067, 12 pages (2014).

Ou, X., et al., "Characterization of spike glycoprotein of SARS-CoV-2 on virus entry and its immune cross-reactivity with SARS-CoV", Nature Communications 11, 1620, 1-12, Supplementary Information, 16 pages (2020).

Pallesen, J., et al., "Immunogenicity and structures of a rationally designed prefusion MERS-CoV spike antigen", PNAS, doi/10.1073/pnas.1707304114, E7348-E7357 (2017).

Pati, R., et al., "Nanoparticle Vaccines Against Infectious Diseases", Front Immunol 9, 2224, 16 pages (2018).

Portolano, N., "Recombinant protein expression for structural biology in HEK 293F suspension cells: a novel and accessible approach", J Vis Exp (92), e51897, doi:10.3791/51897, 1-8 (2014).

Sekimukai, H., et al., "Gold nanoparticle-adjuvanted S protein induces a strong antigen-specific IgG response against severe acute respiratory syndrome-related coronavirus infection, but fails to induce protective antibodies and limit eosinophilic infiltration in lungs", Microbiology and Immunology 64, 33-51 (2020) (Epub Nov. 2019).

Shang, J., et al., "Cell entry mechanisms of SARS-CoV-2", PNAS 117 (21), 11727-11734 (2020).

Shang, J., et al., "Structural basis of receptor recognition by SARS-CoV-2", Nature 581, 221-224, 18 pages (2020).

Tai, W., et al., "Characterization of the receptor-binding domain (RBD) of 2019 novel coronavirus: implication for development of RBD protein as a viral attachment inhibitor and vaccine", Cellular & Molecular Immunology 17, 613-620 (2020).

Walls, A., et al., "Elicitation of Potent Neutralizing Antibody Responses by Designed Protein Nanoparticle Vaccines for SARS-CoV-2", Cell 183 (5), 1367-1382, e1317 (2020).

Walls, A., et al., "Structure, Function, and Antigenicity of the SARS-CoV-2 Spike Glycoprotein", Cell 180, 281-292 (2020).

Wang, X., et al., "SARS-CoV-2 infects T lymphocytes through its spike protein-mediated membrane fusion", Cell Mol Immunol, https://doi.org/10.1038/s41423-020-0424-9, 3 pages and two retraction notices 2 pages (2020).

Wang, Q., et al., "Structural and Functional Basis of SARS-CoV-2 Entry by Using Human ACE2", Cell 181, 894-904 (2020).

Wei, Y., et al., "Biomedical Applications of Lumazine Synthase", Journal of Pharmaceutical Sciences 107, 2283-2296 (2018).

Wu, K., et al., "Crystal structure of NL63 respiratory coronavirus receptor-binding domain complexed with its human receptor", PNAS 106 (47), 19970-19974 (2009).

Wu, K., et al., "Mechanisms of Host Receptor Adaptation by Severe Acute Respiratory Syndrome Coronavirus", Journal of Biological Chemistry 287 (12), 8904-8911 (2012).

Xia, S., et al., "A pan-coronavirus fusion inhibitor targeting the HR1 domain of human coronavirus spike", Sci Adv 5 (4), eaav4580, doi: 10.1126/sciadv.aav4580, 1-15 (2019).

Ye, G., et al., "The Development of a Novel Nanobody Therapeutic for SARS-CoV-2", bioRxiv preprint, https://doi.org/10.1101/2020.11.17.386532, 1-48 (2020).

Zhao, R., et al., "Serological diagnostic kit of SARS-CoV-2 antibodies using CHO-expressed full-length SARS-CoV-2 S1 proteins", medRxiv preprint doi: https://doi.org/10.1101/2020.03.26.20042184, 24 pages (2020).

\* cited by examiner

FIGURE 2

293T-hACE2 Cells

[Graph: Relative Pseudovirus Entry (y-axis, 0 to 120000) vs Sera dilution (x-axis, $10^{-2}$, $10^{-3}$, $10^{-4}$, $10^{-5}$)]

- —●— SARS2 RBD-hFc + Nanoparticle Immunized Group-1
- —■— SARS2 RBD-hFc + Nanoparticle Immunized Group-2
- —✶— SARS2 RBD-hFc + Nanoparticle Immunized Group-3
- —✕— SARS2 RBD-hFc + Nanoparticle Immunized Group-4
- —◆— SARS2 RBD-hFc + Nanoparticle Immunized Group-5

FIGURES 7A-7C

FIGURES 8A-8C
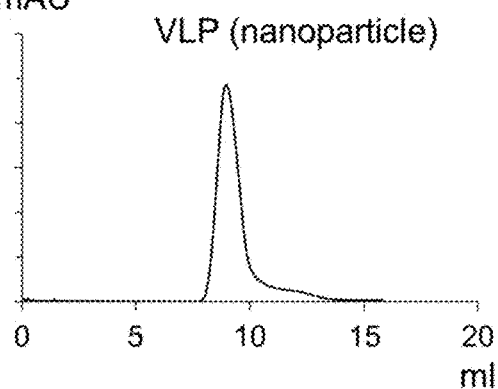
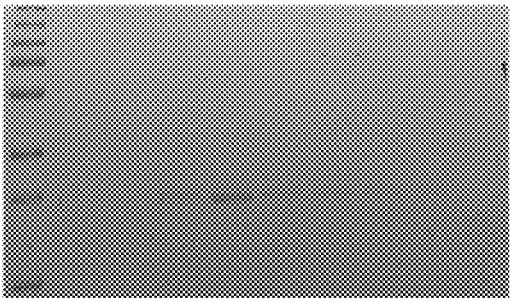
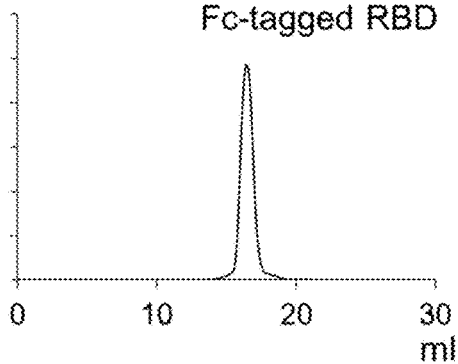
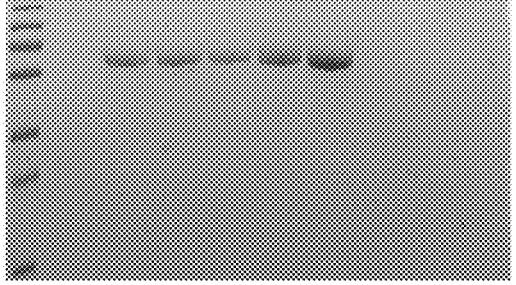
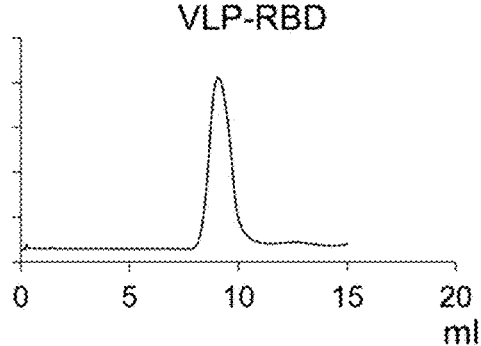
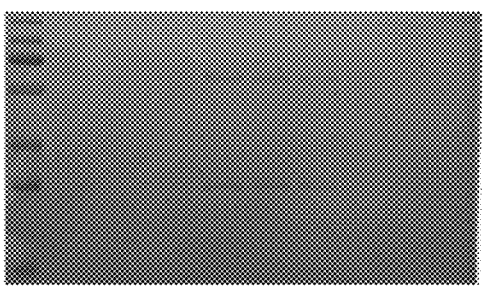

VIRUS LIKE NANOPARTICLE COMPOSITIONS AND METHODS THEREOF

CROSS REFERENCE TO RELATED APPLICATION

This application claims priority to U.S. Provisional Application No. 63/047,120 filed on Jul. 1, 2020, which is incorporated by reference herein.

GOVERNMENT FUNDING

This invention was made with government support under AI139092, AI089728, AI110700, AI149644, AI157253, OD026529, AI007419, AI007151 and CA016086 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 20, 2021, is named 09531_520US1_SL.txt and is 75,590 bytes in size.

BACKGROUND OF THE INVENTION

Coronaviruses, which cause disease in mammals and birds, are a group of enveloped viruses that have a positive-sense single-stranded RNA genome and a nucleocapsid of helical symmetry. Their genome encodes four major structural proteins: Spike (S), membrane (M), envelope (E) and nucleocapsid (N). The S protein mediates binding of the virus to the host cell receptor, and fusion between the two membranes allows for viral entry into the host cell. The S protein of SARS-CoV-2 consists of 2 subunits, S1 and S2. The S1 subunit binds to the host receptor through its receptor-binding domain (RBD) (i.e., binds to human angiotensin-converting enzyme 2 (ACE2)), allowing for conformational changes and membrane fusion.

In humans, coronaviruses cause respiratory tract infections that can range from mild to lethal. Mild illnesses include some cases of the common cold, while more lethal varieties can cause COVID-19, SARS and MERS. SARS-coronavirus 2 (SARS-CoV-2) causes COVID-19, a disease that has spread rapidly and created a global health emergency.

Different types of vaccines are being developed throughout the world to battle COVID-19; however, limitations are associated with these different forms. For example, nucleic acid-based vaccines (e.g., DNA vaccines or mRNA vaccines) often do not elicit sufficient immune responses in a host because the nucleic acid must be translated into a protein after injection, which is often difficult to control. Viral vector-based vaccines (e.g., adenovirus vector expressing SARS-CoV-2 antigens) have been previously associated with severe side effects and may be cleared by the host body quickly due to pre-immunity to the virus. Additionally, virus-based vaccines have been associated with safety concerns. For example, attenuated virus particles may infect immunocompromised people and/or may mutate back to wild type viruses and infect even healthy people. Inactivated virus particles may lose their antigenicity due to the inactivation procedure. Thus, there is a need to develop robust and effective COVID-19 vaccines that prevent or ameliorate these infections.

SUMMARY OF THE INVENTION

Certain embodiments of the invention provide a virus-like nanoparticle (VLP) comprising:
1) a plurality of oligomerized VLP monomer polypeptides, wherein each VLP monomer polypeptide comprises an Fc binding domain amino acid sequence operably linked to a lumazine synthase (LS) amino acid sequence; and
2) a plurality of Spike (S)-antigen-Fc polypeptides, wherein each S-antigen-Fc polypeptide comprises a SARS-CoV-2 Spike protein domain amino acid sequence operably linked to a Fc domain amino acid sequence.

Certain embodiments of the invention provide a method of producing a VLP as described herein, comprising contacting a plurality of oligomerized VLP monomer polypeptides as described herein with a plurality of the S-antigen-Fc polypeptides as described herein, under conditions suitable for Fc binding to occur.

Certain embodiments of the invention provide a VLP produced by a method as described herein.

Certain embodiments of the invention provide a composition comprising:
a) a VLP monomer polypeptide as described herein,
b) a S-antigen-Fc polypeptide, or a multimer thereof (e.g., dimer), as described herein, and/or
c) a VLP as described herein,
and a carrier. For example, in certain embodiments, the composition is a pharmaceutical composition or a vaccine composition. Thus, in certain embodiments, the composition is a pharmaceutical composition comprising a VLP as described herein and a pharmaceutically acceptable carrier.

Certain embodiments of the invention provide a polynucleotide comprising a nucleotide sequence encoding a VLP monomer polypeptide as described herein, or a S-antigen-Fc polypeptide as described herein.

Certain embodiments of the invention provide an expression cassette comprising a promoter operably linked to the polynucleotide as described herein.

Certain embodiments of the invention provide a vector comprising the polynucleotide as described herein, or the expression cassette as described herein.

Certain embodiments of the invention provide a cell comprising the polynucleotide as described herein, the expression cassette as described herein or the vector as described herein.

Certain embodiments of the invention provide a method of immunizing an animal for the prevention of a coronavirus infection (e.g., a SARS-CoV-2 infection), comprising administering a first dose of an effective amount of a VLP as described herein, or a composition as described herein to the animal.

Certain embodiments of the invention provide a method for treating or preventing a coronavirus infection (e.g., a SARS-CoV-2 infection) in an animal, comprising administering an effective amount of a VLP as described herein or a composition as described herein to the animal.

Certain embodiments of the invention provide a method for eliciting a coronavirus (e.g., SARS-CoV-2) neutralizing antibody response in an animal, comprising administering an effective amount of a VLP as described herein or a composition as described herein to the animal.

Certain embodiments of the invention provide a VLP as described herein or a composition as described herein for use in medical therapy.

Certain embodiments of the invention provide a VLP as described herein or a composition as described herein for 1) immunizing an animal for the prevention of a coronavirus infection (e.g., a SARS-CoV-2 infection); 2) the prophylactic or therapeutic treatment of a coronavirus infection (e.g., a SARS-CoV-2 infection); or 3) eliciting a coronavirus (e.g., SARS-CoV-2) neutralizing antibody response in an animal.

Certain embodiments of the invention provide a kit comprising:
1) a VLP as described herein or a composition as described herein;
2) packaging material; and
3) instructions for administering the VLP to an animal for 1) immunizing the animal for the prevention of a coronavirus infection (e.g., SARS-CoV-2 infection); 2) treating or preventing a coronavirus infection (e.g., a SARS-CoV-2 infection) in the animal; or 3) eliciting a coronavirus (e.g., SARS-CoV-2) neutralizing antibody response in the animal.

Certain embodiments of the invention provide a VLP monomer polypeptide as described herein.

Certain embodiments of the invention provide an S-antigen-Fc polypeptide, or a multimer thereof (e.g., dimer thereof), as described herein. For example, certain embodiments provide an S-antigen-Fc polypeptide comprising a SARS-CoV-2 Spike protein domain amino acid sequence linked directly or through a linker group to a Fc domain amino acid sequence, wherein the SARS-CoV-2 Spike protein domain amino acid sequence is a SARS-CoV-2 receptor binding domain (RBD) amino acid sequence (e.g., that is between about 197 to about 275 amino acids in length), and wherein the Fc domain amino acid sequence comprises a human IgG1, IgG2, IgG3 or IgG4 Fc domain amino acid sequence. In certain embodiments, the SARS-CoV-2 RBD amino acid sequence comprises a sequence having at least about 90% sequence identity to SEQ ID NO:1, and wherein the Fc domain amino acid sequence comprises an amino acid sequence having at least about 90% sequence identity to SEQ ID NO:4. In certain embodiments, the S-antigen-Fc polypeptide comprises SEQ ID NO:5 or 6.

Certain embodiments also provide a composition (e.g., a vaccine composition) comprising an S-antigen-Fc polypeptide as described herein and a carrier. Certain embodiments provide a method of 1) immunizing an animal for the prevention of a coronavirus infection; 2) treating or preventing a coronavirus infection in an animal; and/or 3) eliciting a coronavirus neutralizing antibody response in an animal, comprising administering a first dose of such a composition to the animal.

Certain embodiments of the invention provide a protein comprising a first antigen-Fc polypeptide operably linked to a second antigen-Fc polypeptide.

The invention also provides processes and intermediates disclosed herein that are useful for preparing a polypeptide or virus-like particle (VLP) described herein, as well as compositions described herein.

BRIEF DESCRIPTION OF THE FIGURES

FIG. 2. Inhibition of pseudovirus entry by immunized mouse sera. Mice immunized with SARS-CoV-2 RBD-hFc+Nanoparticle generated high-titer antibodies, which could neutralize SARS-CoV-2 pseudovirus entry into 293T-hACE2 cells. In the assay, SARS-CoV-2 pseudoviruses were used to enter target cells (293T-hACE2 cells stably expressing human ACE2). Mouse sera from each group were diluted as indicated and incubated with SARS-CoV-2 pseudoviruses at 37° C. for 1 hour before entering target cells. Pseudovirus entry was characterized as luciferase signal accompanying the entry (measured as relative light units or RLUs). Error bars represent the standard error of the mean (SEM).

(FIG. 3A) Schematic representation of Fc-tagged SARS-CoV-2 RBD, N-terminal protein A tag of nanoparticle, and 60-meric VLP nanoparticle formed by bacterial lumazine synthase (spheres). (FIG. 3B) Negative-stain EM analysis of VLP (left) and VLP-RBD complex (right). (FIG. 3C) Binding of VLP to SARS-CoV-2 RBD as detected using ELISA. SARS-CoV-2 RBD or equal amounts of BSA (negative control) were coated on ELISA plate, and VLP (containing a N-terminal His tag and protein A tag) was added later. Binding of VLP to RBD was detected by anti-His tag antibody. The data are presented as mean SEM (n=12). A Student's two-tailed t-test was performed to analyze the statistical differences among different groups. ***p<0.001. Experiments were repeated twice with similar results.

(FIG. 5D) Mouse sera from day 10 post-$2^{nd}$ immunization were tested for blocking the interaction between SARS-CoV-2 RBD and human ACE2 receptor using flow cytometry. Recombinant RBD was incubated with cells expressing ACE2 in the presence of mouse sera, and efficiency of binding was characterized by flow cytometry signal (i.e., fluorescence intensity of cells). Inhibition (%) was derived from flow cytometry signal in the presence or absence of mouse sera. The data are presented as mean±SEM (n=5 for mice in each group). A Student's two-tailed t-test was performed to analyze the statistical differences among different groups. *$p<0.001$; $p<0.01$; *$p<0.05$_Experiments were repeated twice with similar results.

FIGS. 7A-7C. VLP-RBD vaccine protects mice from SARS-CoV-2 infection in vivo. Mice were immunized with VLP-RBD vaccine, RBD vaccine or PBS, and were then intranasally challenged with a mouse-adapted SARS-CoV-2 strain. Clinical scores (FIG. 7A), body weights (FIG. 7B), and virus titers in the lung tissue (FIG. 7C) of mice were recorded. The data are presented as mean±SEM (n=4-5 for mice in each group). For (FIG. 7B), a two-way ANOVA with a Dunnett's multiple comparisons post-test was performed to analyze the statistical differences among different groups. For (FIG. 7C), a Kruskal-Wallis test with Dunn's multiple comparisons was performed to analyze the statistical differences among different groups. *$p<0.001$; $p<0.01$ FIGS. 8A-8C. Preparation of VLP nanoparticle, SARS-CoV-2 RBD, and VLP-based SARS-CoV-2 RBD vaccine. VLP nanoparticle (FIG. 8A), Fc-tagged SARS-CoV-2 RBD (FIG. 8B), and VLP-RBD complex (FIG. 8C) were each purified to high homogeneity. Left: representative elution profiles of the three proteins from Superose 6 Increase 10/300 GL high-resolution gel filtration chromatography. mAU: milli-absorbance unit at 280 nm wavelength. Right: representative SDS-PAGE gels (stained by coomasie blue) of peak fractions from the gel filtration chromatography. Experiments were repeated twice with similar results.

FIG. 9E shows antibody responses induced by VLP-RBD vaccine potently neutralize the cell entry of pseudotyped SARS-CoV-2 variant containing one of naturally occurring mutations (V367F, G476S, G485R, H519Q, or D614G) in the spike proteins. The experiments were performed in the same way as in FIG. 6, except that the spike protein contains one of the indicated mutations.

DETAILED DESCRIPTION

Figure 1:
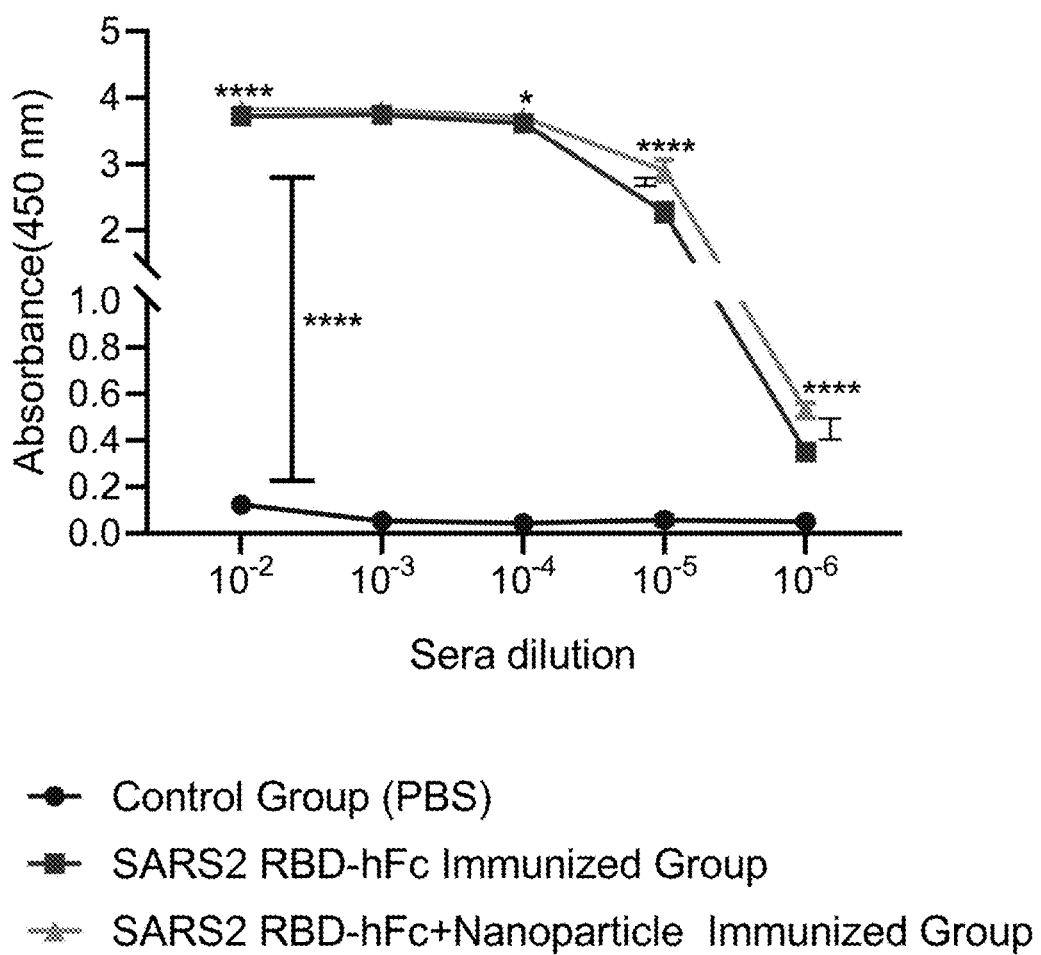
FIG. 1. Binding of immunized mouse sera to SARS-CoV-2 RBD as shown by ELISA. Mice immunized with either SARS-CoV-2 RBD-hFc or SARS-CoV-2 RBD-hFc+Nanoparticle generated high-titer antibodies against SARS-CoV-2 RBD. In the assay, 10 µg/ml SARS-CoV-2 RBD-His protein was coated onto the ELISA plate. Mouse sera from each group were diluted as indicated and added to the ELISA plates and incubated at 37° C. for 1 hour. After washing, 50 µL Peroxidase AffiniPure Goat Anti-Mouse total IgG (H+L) antibodies (1:2000 dilution) (JACKSON IMMUNORESEARCH LABORATORIES INC.) was added and incubated for 1 hour at 37° C. Finally, after more washing, the bound proteins were detected using 50 µL ELISA substrate (tetramethylbenzidine) (SIGMA-ALDRICW). The reaction was stopped using 50 µL 1N $H_2SO_4$. ELISA signal was read using the Epoch Microplate Spectrophotometer (BioTek Instruments) at the 450 nm wavelength. Error bars represent the standard error of the mean (SEM).

While not wishing to be bound by theory, efficacy of protein-based vaccines (e.g., a subunit vaccine) may be suboptimal partly because the human immune system has evolved to recognize not individual viral proteins, but virus particles. More specially, the human immune system efficiently recognizes two features of virus particles: (i) high local density of antigens; and (ii) repetitive patterns of antigen display, which tend to engage B cell receptors and a variety of immune cells more efficiently. As compared to other vaccine approaches, virus like nanoparticle (VLP) vaccines have a reduced risk of side effects and may have an increased efficacy, as the protein scaffold is not infectious and multiple copies (e.g., 5, 10 or 60 or more copies) of an antigen can be displayed in an ordered array on the VLP protein scaffold. Thus, VLP vaccines combine the advantages of both conventional virus-based vaccines and protein-based vaccines, while reducing their drawbacks.

As described in the Examples, a virus-like particle (VLP) vaccine was developed, which combines the effectiveness of virus-based vaccines and the safety of protein-based vaccines. Using the lumazine synthase nanoparticle protein as the structural scaffold and a SARS-CoV-2 receptor-binding domain as the surface immunogen (e.g., 120 copies), this VLP vaccine induced high-titer neutralizing antibody responses in mice that lasted >2 months and potently inhibited SARS-CoV-2, SARS-CoV-1, and their variants. The VLP vaccine also protected mice from high-titer SARS-CoV-2 challenge. Therefore, this VLP vaccine potentially provides effective and long-term protection to the human population against SARS-CoV-2 and its variants.

Accordingly, described herein are VLP monomer polypeptides that comprise a Fc binding domain. These VLP monomer polypeptides (e.g., homo-monomer) can oligomerize to self-assemble to form a VLP scaffold and can bind/display multiple copies of antigen-Fc fusion polypeptides.

Thus, described herein is a virus-like nanoparticle (VLP) scaffold comprising: a plurality of oligomerized VLP monomer polypeptides, wherein each VLP monomer polypeptide comprises an Fc binding domain amino acid sequence (e.g., a Protein A domain or a Protein G domain) operably linked to a lumazine synthase (LS) amino acid sequence.

As used herein, the terms "VLP scaffold" and "nanoparticle" are used interchangeably to refer to a plurality of VLP monomer polypeptides (e.g., homo-monomers) that have oligomerized or self-assembled into a supramolecular protein scaffold. Antigen-Fc fusion polypeptides may be attached to this scaffold to produce a VLP.

Accordingly, certain embodiments provide a virus-like nanoparticle (VLP) comprising:
1) a plurality of oligomerized VLP monomer polypeptides (i.e., a VLP scaffold), wherein each VLP monomer polypeptide comprises an Fc binding domain amino acid sequence operably linked to a lumazine synthase (LS) amino acid sequence; and
2) a plurality of antigen-Fc polypeptides, wherein each antigen-Fc polypeptide comprises an antigen amino acid sequence operably linked to a Fc domain amino acid sequence.

In certain embodiments, the antigen is a SARS-CoV-2 protein, or fragment thereof, such as a Spike protein domain amino acid sequence. In some embodiments, the SARS-CoV-2 protein fragment includes the RBD domain of the Spike protein.

Thus, certain embodiments provide a virus-like nanoparticle (VLP) comprising:
1) a plurality of oligomerized VLP monomer polypeptides, wherein each VLP monomer polypeptide comprises an Fc binding domain amino acid sequence operably linked to a lumazine synthase (LS) amino acid sequence; and
2) a plurality of Spike (S)-antigen-Fc polypeptides, wherein each S-antigen-Fc polypeptide comprises a SARS-CoV-2 Spike protein domain amino acid sequence operably linked to a Fc domain amino acid sequence.

As used herein, the term "plurality" refers to two or more of a particular element. For example, two or more polypeptides. In certain embodiments, a plurality may refer to 2, 3, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 230, 240, 250, 260, 270, 280, 290, 300 or more elements. In certain embodiments, a plurality may refer to 2 to 180, or 5 to 180, or 10 to 180, or 20 to 180, or 30 to 180, or 40 to 180, or 50 to 180, or 60 to 180, or 70 to 180, or 80 to 180, or 90 to 180, or 100 to 180, or 110 to 180, or 120 to 180, or 130 to 180, or 140 to 180, or 150 to 180, or 160 to 180, or 170 to 180, of a given element (e.g., polypeptide). In certain embodiments, a plurality may refer to 2 to 120, or 5 to 120, or 10 to 120, or 20 to 120, or 30 to 120, or 40 to 120, or 50 to 120, or 60 to 120, or 70 to 120, or 80 to 120, or 90 to 120, or 100 to 120, or 110 to 120, of a given element (e.g., polypeptide). In certain embodiments, a plurality may refer to 2 to 60, or 5 to 60, or 10 to 60, or 20 to 60, or 30 to 60, or 40 to 60 or 50 to 60 of a given element (e.g., polypeptide). In certain embodiments, a plurality refers to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 or more of a given element. Additionally, the elements within a plurality may be each independently selected, and therefore, may be the same or different. For example, a VLP as described herein may comprise a plurality of S-antigen-Fc polypeptides, which are the same (i.e., the VLP displays a single type of antigen). In other embodiments, the VLP may comprise a plurality of S-antigen-Fc polypeptides, which are different (e.g., the VLP may display a mixture of antigens).

Thus, in certain embodiments, the VLP comprises five or more VLP monomer polypeptides, wherein the polypeptides are oligomerized. In certain embodiments, the VLP comprises ten or more VLP monomer polypeptides, wherein the polypeptides are oligomerized. In certain embodiments, the VLP comprises sixty or more VLP monomer polypeptides, wherein the polypeptides are oligomerized.

In certain embodiments, the VLP comprises a pentamer of the VLP monomer polypeptides. In certain embodiments, the plurality of oligomerized VLP monomer polypeptides is a pentamer (e.g., to generate a pentameric VLP). In certain embodiments, the VLP comprises a decamer of the VLP monomer polypeptides. In certain embodiments, the plurality of oligomerized VLP monomer polypeptides is a decamer (e.g., to generate a decameric VLP). In certain embodiments, the VLP comprises 60-mer of the VLP monomer polypeptide. In certain embodiments, the plurality of oligomerized VLP monomer polypeptides is a 60-mer (e.g., to generate a 60-meric VLP). In certain embodiments, the VLP is an icosahedral VLP.

As described herein, the VLP comprises a plurality of antigen-Fc polypeptides (e.g., S-antigen-Fc polypeptides). In certain embodiments, two or more of the antigen-Fc polypeptides comprised within the VLP are oligomerized (e.g., dimerized, trimerized, tetramerized, pentamerized, etc.). Therefore, more than one antigen-Fc polypeptide may be bound to each VLP monomer polypeptide. For example, provided the antigen-Fc polypeptides dimerize, 120 copies of the antigen-Fc polypeptide may be displayed on the surface of a 60-meric VLP scaffold comprising oligomerized VLP monomer polypeptides. In certain embodiments, at least about 20%, 30%, 40%, 50%, 60%, 70%, 80%, 90%, 95%, 96%, 97%, 98%, 99% or 100% of the antigen-Fc polypeptides comprised within the VLP are oligomerized. In certain embodiments, two or more of the antigen-Fc polypeptides comprised within the VLP are dimerized. In certain embodiments, at least about 20%, 30%, 40%, 50%, 60%, 70%, 80%, 90%, 95%, 96%, 97%, 98%, 99% or 100% of the antigen-Fc polypeptides comprised within the VLP are dimerized.

In certain embodiments, the VLP comprises about 2, 3, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 230, 240, 250, 260, 270, 280, 290, 300 or more copies of the antigen-Fc polypeptide. In certain embodiments, the VLP comprises about 2 to 120, or 5 to 120, or 10 to 120, or 20 to 120, or 30 to 120, or 40 to 120, or 50 to 120, or 60 to 120, or 70 to 120, or 80 to 120, or 90 to 120, or 100 to 120, or 110 to 120 copies of the antigen-Fc polypeptide. In certain embodiments, the VLP comprises from about 60 copies to 120 copies of the antigen-Fc polypeptide. In certain embodiments, the VLP comprises from about 80 copies to 120 copies of the antigen-Fc polypeptide. In certain embodiments, the VLP comprises from about 100 copies to 120 copies of the antigen-Fc polypeptide. In certain embodiments, the VLP comprises from about 110 copies to 120 copies of the antigen-Fc polypeptide. In certain embodiments, the VLP comprises from about 3 copies to 60 copies of the antigen-Fc polypeptide. In certain embodiments, the VLP comprises from about 5 copies to 60 copies of the antigen-Fc polypeptide. In certain embodiments, the VLP comprises from about 10 copies to 60 copies of the antigen-Fc polypeptide. In certain embodiments, the VLP comprises from about 20 copies to 60 copies of the antigen-Fc polypeptide. In certain embodiments, the VLP comprises from about 30 copies to 60 copies of the antigen-Fc polypeptide. In certain embodiments, the VLP comprises from about 40 copies to 60 copies of the antigen-Fc polypeptide. In certain embodiments, the VLP comprises from about 50 copies to 60 copies of the antigen-Fc polypeptide. In certain embodiments, the VLP comprises about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 or more copies of the antigen-Fc polypeptide. In certain embodiments, the VLP comprises 60 copies of the antigen-Fc polypeptide. In certain embodiments, 60 copies of the antigen-Fc polypeptide are included in the VLP. In certain embodiments, the VLP comprises 120 copies of the antigen-Fc polypeptide. In certain embodiments, 120 copies of the antigen-Fc polypeptide are included in the VLP.

In certain embodiments, the VLP is a single-antigen VLP, wherein only one type of antigen-Fc polypeptide is present in the VLP (e.g., only one type of antigen-Fc polypeptide is displayed on the VLP scaffold). Thus, individual VLPs only comprise multiple copies of one antigen-Fc polypeptide. For example, a VLP scaffold may be contacted with (e.g., mixed with) one type of antigen-Fc polypeptide to produce the single-antigen VLP. In certain embodiments, only SARS CoV-2 S1-Fc is present in a single VLP. In certain embodiments, only SARS CoV-2 RBD-Fc is present in a single VLP.

In other embodiments, the VLP is a multi-antigen VLP. Thus, more than one types of antigen-Fc polypeptides are present in an individual VLP (e.g., a combination of SARS CoV-2 S1-Fc and SARS CoV-2 RBD-Fc polypeptides are present). For example, two or more types of antigen-Fc polypeptides may be contacted (e.g., simultaneously or sequentially) with the VLP scaffold to generate a multi-antigen VLP. Thus, individual VLPs can comprise two or more types of antigen-Fc polypeptides. In certain embodiments, the VLP further comprises a third S-antigen-Fc polypeptide amino acid sequence that comprises a third SARS-CoV-2 Spike protein domain amino acid as described herein.

In certain embodiments, the VLP has a diameter size range of about 10-1000 nm, about 20-900 nm, about 30-800 nm, about 40-700 nm, about 50-600 nm, about 60-500 nm, about 70-400 nm, about 80-300 nm or about 90-200 nm. In certain embodiments, the VLP has a diameter size range of about 20-300 nm. In certain embodiments, the VLP has a diameter size range of about 30-200 nm. In certain embodiments, the VLP has an average diameter size of about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 450, 500, 550, 600, 650, 700, 750, 800, 850 or 900 nm.

Certain embodiments of the invention also provide a method of producing a VLP as described herein, comprising contacting a plurality of oligomerized VLP monomer polypeptides as described herein with a plurality of the antigen-Fc polypeptides as described herein (e.g., an S-antigen-Fc polypeptide described herein), under conditions suitable for Fc binding to occur.

In certain embodiments, prior to the contacting step, the VLP monomer polypeptides are mixed under conditions suitable for oligomerization to occur (e.g., to self-assemble as a VLP scaffold).

In certain embodiments, a polypeptide described herein (e.g., a VLP monomer polypeptide or an antigen-Fc polypeptide) is produced in a host cell. In certain embodiments, the host cell is a bacterial cell (e.g., an *E. coli* cell). In certain embodiments, the host cell is a mammalian cell (e.g., a 293 cell, such as 293F).

A variety of molar ratios of antigen-Fc polypeptide to VLP monomer polypeptide can be used to produce a VLP as described herein. In certain embodiments, the molar ratio of antigen-Fc polypeptide to VLP monomer polypeptide (e.g., molar ratio of dimerized antigen-Fc polypeptide to VLP monomer polypeptide) can be any ratio between about 0.05:1 to about 20:1 (e.g., about 0.1:1, 0.2:1, 0.3:1, 0.4:1, 0.5:1, 0.6:1, 0.7:1, 0.8:1, 0.9:1, 1:1, 1.5:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 or 20:1). In certain embodiments, the molar ratio of antigen-Fc polypeptide to VLP monomer polypeptide is about 0.8:1 to about 2:1. In certain embodiments, the molar ratio of antigen-Fc polypeptide to VLP monomer polypeptide is about 0.8:1. In certain embodiments, the molar ratio of antigen-Fc polypeptide to VLP monomer polypeptide is about 0.9:1. In certain embodiments, the molar ratio of antigen-Fc polypeptide to VLP monomer polypeptide is about 1:1. In certain embodiments, a molar excess of the antigen-Fc polypeptides (e.g., a molar excess of dimerized antigen-Fc polypeptide) is used for contacting (e.g., mixing). In certain embodiments, the molar ratio of antigen-Fc polypeptide to VLP monomer polypeptide is about 1.2:1. In certain embodiments, the molar ratio of antigen-Fc polypeptide to VLP monomer polypeptide is about 1.4:1. In certain embodiments, the molar ratio of antigen-Fc polypeptide to VLP monomer polypeptide is about 1.6:1. In certain embodiments, the molar ratio of antigen-Fc polypeptide to VLP monomer polypeptide is about 1.8:1. In certain embodiments, the molar ratio of antigen-Fc polypeptide to VLP monomer polypeptide is about 2:1. In some embodiments, the molar ratio of antigen-Fc polypeptide to VLP monomer peptide can be any ratio between 0.8:1 to about 2:1. In certain embodiments, the molar ratio of antigen-Fc polypeptide to VLP monomer polypeptide is about 1:1, 2:1, 3:1, 4:1, 5:1, or 6:1.

Certain embodiments of the invention also provide a VLP produced by a method described herein.

VLP Monomer Polypeptides

Certain embodiments of the invention provide a VLP monomer polypeptide as described herein. A plurality of such VLP monomer polypeptides may be included in a VLP described herein.

In certain embodiments, the VLP monomer polypeptide comprises an Fc binding domain amino acid sequence operably linked to a lumazine synthase (LS) amino acid sequence. The LS domain mediates self-assembly of monomers into a VLP and the Fc binding domain amino acid facilitates the attachment of the antigen-Fc polypeptides (e.g., S-antigen-Fc polypeptides). As discussed herein, the antigen-Fc polypeptides may oligomerize (e.g., dimerize). Thus, one Fc binding domain amino acid sequence may bind to an Fc polypeptide present in an antigen-Fc polypeptide oligomer/multimer (e.g., dimer), thereby facilitating the attachment of more than one antigen-Fc polypeptide.

Lumazine Synthase (LS)

Lumazine synthase is a family of bacterial enzymes that comprise a plurality of homo-monomers capable of oligomerizing to self-assemble into supramolecular structures, including pentamer, decamer and icosahedral sixty-mer structures, depending on origin of species. Thus, oligomerized LS amino acid sequences may be used to generate a supramolecular protein scaffold. Antigens may be attached to this scaffold to produce a structure that mimics viral particles (i.e., a VLP).

In certain embodiments, the LS amino acid sequence is derived from a bacteria species selected from *Aquifex aeolicus*, *Brucella* spp., *Brucella abortus*, or *Bacillus anthracis*. In certain embodiments, the LS amino acid sequence is derived from a bacteria species described in Wei et al., Journal of Pharmaceutical Sciences 107 (2018) 2283-2296, which is incorporated herein by reference for all purposes.

In certain embodiments, a VLP monomer polypeptide described herein can self-assemble into a decameric VLP. In certain embodiments, the LS amino acid sequence is derived from *Brucella* spp.

In certain embodiments, a VLP monomer polypeptide described herein can self-assemble into an icosahedral sixty-mer VLP. In certain embodiments, the LS amino acid sequence is derived from *Aquifex aeolicus* (e.g., NCBI accession no. WP_010880027.1).

In certain embodiments, the LS amino acid sequence comprises one or more point mutations compared to a wild-type LS amino acid sequence. For example, the LS amino acid sequence (e.g., SEQ ID NO:12) may comprise C37A and N102Q mutations compared to wild-type *Aquifex aeolicus* LS amino acid sequence (SEQ ID NO:30). In certain embodiments, the LS amino acid sequence comprises an amino acid sequence having at least about 80% sequence identity to SEQ ID NO:12. In certain embodiments, the LS amino acid sequence comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:12. In certain embodiments, the LS amino acid sequence comprises an amino acid sequence having at least about 85% sequence identity to SEQ ID NO: 12. In certain embodiments, the LS amino acid sequence comprises an amino acid sequence having at least about 90% sequence identity to SEQ ID NO: 12. In certain embodiments, the LS amino acid sequence comprises an amino acid sequence having at least about 95% sequence identity to SEQ ID NO:12. In certain embodiments, the LS amino acid sequence comprises an amino acid sequence having at least about 98% sequence identity to SEQ ID NO: 12. In certain embodiments, the LS amino acid sequence comprises SEQ ID NO: 12. In certain embodiments, the LS amino acid sequence consists of SEQ ID NO:12.

In certain embodiments, the LS amino acid sequence comprises an amino acid sequence having at least about 80% sequence identity to SEQ ID NO:30. In certain embodiments, the LS amino acid sequence comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:30. In certain embodiments, the LS amino acid sequence comprises an amino acid sequence having at least about 85% sequence identity to SEQ ID NO:30. In certain embodiments, the LS amino acid sequence comprises an amino acid sequence having at least about 90% sequence identity to SEQ ID NO:30. In certain embodiments, the LS amino acid sequence comprises an amino acid sequence having at least about 95% sequence identity to SEQ ID NO:30. In certain embodiments, the LS amino acid sequence comprises an amino acid sequence having at least about 98% sequence identity to SEQ ID NO:30. In certain embodiments, the LS amino acid sequence comprises SEQ ID NO:30. In certain embodiments, the LS amino acid sequence consists of SEQ ID NO:30.

Fc Binding Domain

Protein A (e.g., UniProt accession number P38507) and Protein G are bacterial proteins capable of binding an Fc domain within an immunoglobulin (e.g., IgG, IgM, IgA, IgE). Accordingly, in certain embodiments, the Fc binding domain amino acid sequence comprises a Protein A or Protein G amino acid sequence, or an Fc binding fragment thereof.

In certain embodiments, the Fc binding domain amino acid sequence comprises a Protein G amino acid sequence, or an Fc binding fragment thereof. In certain embodiments, the Fc binding domain amino acid sequence consists of a Protein G amino acid sequence, or an Fc binding fragment thereof.

In certain embodiments, the Fc binding domain amino acid sequence present in the VLP monomer polypeptide comprises a Protein A domain sequence, or a fragment thereof, that has affinity for a Fc domain (e.g., NCBI Reference Sequence: WP_171840220.1). Thus, in certain embodiments, the Fc binding domain amino acid sequence comprises a Protein A amino acid sequence, or an Fc binding fragment thereof. In certain embodiments, the Fc binding domain amino acid sequence consists of a Protein A amino acid sequence, or an Fc binding fragment thereof. In certain embodiments, the Fc binding domain amino acid sequence present in the VLP monomer polypeptide comprises domain B of Protein A, or a fragment thereof. In certain embodiments, the Fc binding domain amino acid sequence present in the VLP monomer polypeptide comprises domain C of Protein A, or a fragment thereof. In certain embodiments, the Protein A domain sequence is an engineered and/or mutated Protein A domain sequence with enhanced Fc binding and/or biomanufacturing stability (e.g., alkaline stability).

In certain embodiments, the Protein A domain amino acid sequence is between about 50 to about 85 amino acids in length. In certain embodiments, the Protein A domain amino acid sequence is between about 55 to about 65 amino acids in length. In certain embodiments, the Protein A domain amino acid sequence is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, or 84 amino acids in length. In certain embodiments, the Protein A domain amino acid sequence is 57, 58 or 59 amino acids in length. In certain embodiments, the Protein A domain amino acid sequence is 59 amino acids in length.

In certain embodiments, the Protein A domain sequence comprises an amino acid sequence having at least about 80% sequence identity to SEQ ID NO:11. In certain embodiments, the Protein A domain sequence comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:11. In certain embodiments, the Protein A domain sequence comprises an amino acid sequence having at least about 85% sequence identity to SEQ ID NO:11. In certain embodiments, the Protein A domain sequence comprises an amino acid sequence having at least about 90% sequence identity to SEQ ID NO: 11. In certain embodiments, the Protein A domain sequence comprises an amino acid sequence having at least about 95% sequence identity to SEQ ID NO: 11. In certain embodiments, the Protein A domain sequence comprises an amino acid sequence having at least about 98% sequence identity to SEQ ID NO: 11. In certain embodiments, the Protein A domain sequence comprises SEQ ID NO:11. In certain embodiments, the Protein A domain sequence consists of SEQ ID NO: 11. In certain embodiments, the Fc binding domain amino acid sequence consists of SEQ ID NO:11.

Linker Group, Tag and Signal Peptide

In certain embodiments, elements within the VLP monomer polypeptide are directly linked to each other (e.g., through a peptide bond). For example, in certain embodiments, the Fc binding domain amino acid sequence is directly linked to the LS amino acid sequence (e.g., through a peptide bond).

In certain other embodiments, the VLP monomer polypeptide further comprises one or more linker group(s). Such a linker group may be used to link together elements present in the VLP monomer polypeptide. The nature of the linker group is not critical, provided that the linker group does not interfere with the function of the VLP monomer polypeptide or elements comprised within the polypeptide, which are being linked together.

In certain embodiments, the Fc binding domain amino acid sequence is operably linked to the lumazine synthase (LS) amino acid sequence via a linker group. In certain embodiments, the linker group is an amino acid sequence (e.g., a sequence described herein). In certain embodiments, the linker group is an amino acid sequence about 1 to about 50 amino acids in length, or about 1 to about 40 amino acids in length, or about 1 to about 30 amino acids in length, or about 1 to about 25 amino acids in length, or about 5 to about 25 amino acids in length, or about 10 to about 25 amino acids in length, or about 10 to about 20 amino acids in length, or about 15 to about 20 amino acids in length (e.g., 15, 16, 17, 18, 19 or 20 amino acids in length). In certain embodiments, the linker group is a GS rich linker. In certain embodiments, the linker group sequence comprises an amino acid sequence having at least about 80% sequence identity to SEQ ID NO:10. In certain embodiments, the linker group sequence comprises an amino acid sequence having at least about 85% sequence identity to SEQ ID NO:10. In certain embodiments, the linker group sequence comprises an amino acid sequence having at least about 90% sequence identity to SEQ ID NO: 10. In certain embodiments, the linker group sequence comprises an amino acid sequence having at least about 95% sequence identity to SEQ ID NO:10. In certain embodiments, the linker group sequence comprises SEQ ID NO:10. In certain embodiments, the linker group sequence consists of SEQ ID NO:10.

In certain embodiments, the VLP monomer polypeptide further comprises an affinity tag (e.g., poly(His) tag or a myc tag). The location of the affinity tag is not critical, provided that it does not interfere with the function of the LS amino acid sequence or the Fc binding domain amino acid sequence. In certain embodiments, the affinity tag operably linked to the N-terminus or C-terminus of the VLP monomer polypeptide. In certain embodiments, the affinity tag is included within the VLP monomer polypeptide (i.e., not at either terminus).

In certain embodiments, the affinity tag is directly linked to the Fc binding domain amino acid sequence (e.g., via a peptide bond).

In certain embodiments, the affinity tag is operably linked to the Fc binding domain amino acid sequence (e.g., the N-terminus of the Fc binding domain) via a linker group. In certain embodiments, the linker group is an amino acid sequence, such as a linker group amino acid sequence described herein. In certain embodiments, the linker group amino acid sequence is between about 1 to about 25 amino acids in length, or about 1 to about 20 amino acids in length, or about 1 to about 15 amino acids in length, or about 1 to about 10 amino acids in length (e.g., 1, 2, 3, 4, 5, 6, 7, 8, 9 or 10 amino acids in length). In certain embodiments, the linker group sequence comprises an amino acid sequence having at least about 80% sequence identity to SEQ ID NO: 9. In certain embodiments, the linker group sequence comprises an amino acid sequence having at least about 85% sequence identity to SEQ ID NO: 9. In certain embodiments, the linker group sequence comprises an amino acid sequence having at least about 90% sequence identity to SEQ ID NO: 9. In certain embodiments, the linker group sequence comprises an amino acid sequence having at least about 95% sequence identity to SEQ ID NO: 9. In certain embodiments, the linker group sequence comprises SEQ ID NO:9. In certain embodiments, the linker group sequence consists of SEQ ID NO:9.

In certain embodiments, the VLP monomer polypeptide further comprises a signal peptide. In certain embodiments, the signal peptide is tPA signal peptide. In certain embodiments, the signal peptide is cleaved from the polypeptide prior to secretion.

In certain embodiments, the signal peptide is operably linked to the N-terminus of the VLP monomer polypeptide amino acid sequence.

In certain embodiments, the signal peptide is directly linked to the VLP monomer polypeptide amino acid sequence (e.g., directly linked to an affinity tag or directly linked to the Fc binding domain amino acid sequence). In certain embodiments, the signal peptide is linked to the VLP monomer polypeptide amino acid sequence through a linker group (e.g., an amino acid linker group).

Thus, in certain embodiments, the VLP monomer polypeptide further comprises one or more linker group(s), an affinity tag and/or a signal peptide sequence.

In certain embodiments, the VLP monomer polypeptide comprises an amino acid sequence having at least about 80% identity to SEQ ID NO:15, 16, 17 or 22. In certain embodiments, the VLP monomer polypeptide comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:15, 16, 17 or 22. In certain embodiments, the VLP monomer polypeptide comprises an amino acid sequence having at least about 85% sequence identity to SEQ ID NO:

15, 16, 17 or 22. In certain embodiments, the VLP monomer polypeptide comprises an amino acid sequence having at least about 90% sequence identity to SEQ ID NO:15, 16, 17 or 22. In certain embodiments, the VLP monomer polypeptide comprises an amino acid sequence having at least about 95% sequence identity to SEQ ID NO: 15, 16, 17 or 22. In certain embodiments, the VLP monomer polypeptide comprises an amino acid sequence having at least about 99% sequence identity to SEQ ID NO:15, 16, 17 or 22. In certain embodiments, the VLP monomer polypeptide comprises SEQ ID NO:15, 16, 17 or 22. In certain embodiments, the VLP monomer polypeptide comprises SEQ ID NO: 15. In certain embodiments, the VLP monomer polypeptide consists of SEQ ID NO: 15. In certain embodiments, the VLP monomer polypeptide comprises SEQ ID NO: 16. In certain embodiments, the VLP monomer polypeptide consists of SEQ ID NO:16. In certain embodiments, the VLP monomer polypeptide comprises SEQ ID NO: 17. In certain embodiments, the VLP monomer polypeptide consists of SEQ ID NO: 17. In certain embodiments, the VLP monomer polypeptide comprises SEQ ID NO:22. In certain embodiments, the VLP monomer polypeptide consists of SEQ ID NO:22.

Antigen-Fc Polypeptides

Certain embodiments of the invention provide an antigen-Fc polypeptide comprising an antigen operably linked to a Fc domain amino acid sequence. The Fc domain amino acid sequence enables binding between the antigen-Fc polypeptide and the Fc binding domain present in the VLP monomer polypeptide, thereby facilitating the attachment of the antigen to the LS-based protein scaffold. In certain embodiments, the antigen-Fc polypeptides may be oligomerized (e.g., in the form of an oligomer/multimer, such as a dimer). For example, two or more antigen-Fc polypeptides may be linked, e.g., linked by a covalent bond, such as a disulfide bond, or by non-covalent interactions such as electrostatic interactions, hydrogen bonding, etc. Thus, one Fc binding domain amino acid sequence may bind to an Fc polypeptide present in an antigen-Fc polypeptide oligomer/multimer (e.g., dimer), and thereby facilitate the attachment of more than one antigen-Fc polypeptide to the VLP scaffold. Thus, a plurality of antigen-Fc polypeptides may be incorporated into a VLP described herein.

In certain embodiments, the antigen is a viral or bacterial antigen. In certain embodiments, the antigen is a coronavirus antigen (e.g., a coronavirus Spike protein antigen). In certain embodiments, the antigen is a MERS antigen. In certain embodiments, the antigen is a SARS-CoV antigen. In certain embodiments, the antigen is a SARS-CoV-2 antigen (e.g., Spike protein, S1, S2, or RBD). Accordingly, certain embodiments provide an antigen-Fc polypeptide comprising a SARS-CoV-2 antigen (e.g., a Spike (S)-antigen) operably linked to a Fc domain amino acid sequence.

In certain embodiments, the SARS-CoV-2 antigen comprises an amino acid sequence derived from a SARS-CoV-2 Spike (S) protein domain (e.g., NCBI Accession number QHD43416.1), or a fragment thereof. Accordingly, certain embodiments provide an S-antigen-Fc polypeptide comprising a SARS-CoV-2 Spike protein domain amino acid sequence operably linked to a Fc domain amino acid sequence.

In certain embodiments, the SARS-CoV-2 Spike protein domain amino acid sequence, or a fragment thereof, is capable of binding human ACE2. In certain embodiments, the SARS-CoV-2 Spike protein domain amino acid sequence, or fragment thereof, comprises/consists of a SARS-CoV-2 S1 amino acid sequence, or a fragment thereof. In certain embodiments, the SARS-CoV-2 Spike protein domain amino acid sequence, or fragment thereof, comprises/consists of a SARS-CoV-2 receptor binding domain (RBD) amino acid sequence, or a fragment thereof.

In certain embodiments, the Spike protein domain amino acid sequence is between about 197 to about 1,273 amino acids in length. In certain embodiments, the Spike protein domain amino acid sequence is between about 200 to about 1,000 amino acids in length. In certain embodiments, the Spike protein domain amino acid sequence is between about 300 to about 800 amino acids in length. In certain embodiments, the Spike protein domain amino acid sequence is between about 400 to about 700 amino acids in length. In certain embodiments, the Spike protein domain amino acid sequence is between about 200 to about 400 amino acids in length. In certain embodiments, the Spike protein domain amino acid sequence is between about 200 to about 300 amino acids in length.

In certain embodiments, the Spike protein domain (e.g., S1) amino acid sequence is between about 600 to about 700 amino acids in length. In certain embodiments, the Spike protein domain (e.g., S1) amino acid sequence is between about 650 to about 690 amino acids in length. In certain embodiments, the Spike protein domain (e.g., S1) amino acid sequence is about 685 amino acids in length. In certain embodiments, the Spike protein domain (e.g., S1) amino acid sequence is about 664 amino acids in length.

In certain embodiments, the RBD amino acid sequence is between about 197 to about 275 amino acids in length. In certain embodiments, the RBD amino acid sequence is between about 197 to about 270 amino acids in length. In certain embodiments, the RBD amino acid sequence is between about 207 to about 270 amino acids in length. In certain embodiments, the RBD amino acid sequence is between about 207 to about 250 amino acids in length. In certain embodiments, the SARS-CoV-2 RBD amino acid sequence is between about 207 to about 227 amino acids in length. In certain embodiments, the SARS-CoV-2 RBD amino acid sequence is between about 197 to about 237 amino acids in length. In certain embodiments, the SARS-CoV-2 RBD amino acid sequence is between about 210 to about 225 amino acids in length. In certain embodiments, the SARS-CoV-2 RBD amino acid sequence is between about 210 to about 222 amino acids in length. In certain embodiments, the SARS-CoV-2 RBD amino acid sequence is between about 211 to about 222 amino acids in length. In certain embodiments, the SARS-CoV-2 RBD amino acid sequence is between about 212 to about 222 amino acids in length. In certain embodiments, the SARS-CoV-2 RBD amino acid sequence is between about 213 to about 221 amino acids in length. In certain embodiments, the RBD amino acid sequence is between about 215 and about 219 amino acids in length. In certain embodiments, the SARS-CoV-2 RBD amino acid sequence is between about 216 to about 218 amino acids in length. In certain embodiments, the SARS-CoV-2 RBD amino acid sequence is 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236 or 237 amino acids in length. In certain embodiments, the RBD amino acid sequence is about 217 amino acids in length. In certain embodiments, the RBD amino acid sequence is between about 225 and about 229 amino acids in length. In certain embodiments, the RBD amino acid sequence is about 227 amino acids in length. In certain embodiments, the RBD amino acid sequence is between about 248 and about 252 amino acids in length.

In certain embodiments, the RBD amino acid sequence is about 200 amino acids in length. In certain embodiments, the RBD amino acid sequence is about 215 amino acids in length. In certain embodiments, the RBD amino acid sequence is about 217 amino acids in length. In certain embodiments, the RBD amino acid sequence is about 225 amino acids in length. In certain embodiments, the RBD amino acid sequence is about 227 amino acids in length. In certain embodiments, the RBD amino acid sequence is about 245 amino acids in length. In certain embodiments, the RBD amino acid sequence is about 250 amino acids in length. In certain embodiments, the RBD amino acid sequence is about 253 amino acids in length.

In certain embodiments, the Spike protein domain (e.g., RBD, or S1) amino acid sequence comprises an amino acid sequence having at least about 80% identity to SEQ ID NO: 1, or 2. In certain embodiments, the Spike protein domain amino acid sequence comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 1, or 2. In certain embodiments, the Spike protein domain amino acid sequence comprises an amino acid sequence having at least about 85% sequence identity to SEQ ID NO: 1, or 2. In certain embodiments, the Spike protein domain amino acid sequence comprises an amino acid sequence having at least about 90% sequence identity to SEQ ID NO:1, or 2. In certain embodiments, the Spike protein domain amino acid sequence comprises an amino acid sequence having at least about 95% sequence identity to SEQ ID NO: 1, or 2. In certain embodiments, the Spike protein domain amino acid sequence comprises an amino acid sequence having at least about 99% sequence identity to SEQ ID NO: 1, or 2. In certain embodiments, the Spike protein domain amino acid sequence comprises SEQ ID NO: 1. In certain embodiments, the Spike protein domain amino acid sequence consists of SEQ ID NO:1. In certain embodiments, the Spike protein domain amino acid sequence comprises SEQ ID NO: 2. In certain embodiments, the Spike protein domain amino acid sequence consists of SEQ ID NO: 2.

In certain embodiments, the SARS-CoV-2 RBD comprises an amino acid sequence having at least about 80% sequence identity to SEQ ID NO:24. In certain embodiments, the SARS-CoV-2 RBD comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:24. In certain embodiments, the SARS-CoV-2 RBD comprises an amino acid sequence having at least about 85% sequence identity to SEQ ID NO:24. In certain embodiments, the SARS-CoV-2 RBD comprises an amino acid sequence having at least about 90% sequence identity to SEQ ID NO:24. In certain embodiments, the SARS-CoV-2 RBD comprises an amino acid sequence having at least about 95% sequence identity to SEQ ID NO:24. In certain embodiments, the SARS-CoV-2 RBD comprises an amino acid sequence having at least about 99% sequence identity to SEQ ID NO:24. In certain embodiments, the SARS-CoV-2 RBD comprises SEQ ID NO:24. In certain embodiments, the SARS-CoV-2 RBD consists of SEQ ID NO:24.

In certain embodiments, 1, 2, 3, 4, 5, 6, 7, 8, 9, or 10 amino acids located at positions 1-10 in reference to SEQ ID NO:24 are not comprised within the SARS-CoV-2 RBD amino acid sequence. In certain embodiments, 1, 2, 3, 4, 5, 6, 7, 8, 9, or 10 amino acids located at positions 228-237 in reference to SEQ ID NO:24 are not comprised within the SARS-CoV-2 RBD amino acid sequence.

In certain embodiments, the SARS-CoV-2 RBD comprises an amino acid sequence having at least 90% identity to the sequence corresponding to SEQ ID NO:24, wherein from 1 to 10 (e.g., consecutive) amino acids located at positions 1-10 in reference to the sequence corresponding to SEQ ID NO:24 are not comprised within the SARS-CoV-2 RBD amino acid sequence. In certain embodiments, from 1 to 9 (e.g., consecutive) amino acids located at positions 1-9; or from 1 to 8 (e.g., consecutive) amino acids located at positions 1-8; or from 1 to 7 (e.g., consecutive) amino acids located at positions 1-7; or from 1 to 6 (e.g., consecutive) amino acids located at positions 1-6; or from 1 to 5 (e.g., consecutive) amino acids located at positions 1-5; or from 1 to 4 (e.g., consecutive) amino acids located at positions 1-4; or from 1 to 3 (e.g., consecutive) amino acids located at positions 1-3; or from 1 to 2 (e.g., consecutive) amino acids located at positions 1-2; or 1 amino acid located at position 1, in reference to the sequence corresponding to SEQ ID NO:24 are not comprised within the SARS-CoV-2 RBD amino acid sequence.

In certain embodiments, the SARS-CoV-2 RBD comprises an amino acid sequence having at least 90% identity to a sequence corresponding to SEQ ID NO:24, and wherein from 1 to 10 (e.g., consecutive) amino acids located at positions 228-237 in reference to the sequence corresponding to SEQ ID NO:24 are not comprised within the SARS-CoV-2 RBD amino acid sequence. In certain embodiments, from 1 to 9 (e.g., consecutive) amino acids located at positions 229-237; or from 1 to 8 (e.g., consecutive) amino acids located at positions 230-237; or from 1 to 7 (e.g., consecutive) amino acids located at positions 231-237; or from 1 to 6 (e.g., consecutive) amino acids located at positions 232-237; or from 1 to 5 (e.g., consecutive) amino acids located at positions 233-237; or from 1 to 4 (e.g., consecutive) amino acids located at positions 234-237; or from 1 to 3 (e.g., consecutive) amino acids located at positions 235-237; or from 1 to 2 (e.g., consecutive) amino acids located at positions 236-237; or 1 amino acid located at position 237, in reference to the sequence corresponding to SEQ ID NO:24 are not comprised within the SARS-CoV-2 RBD amino acid sequence.

In certain embodiments, the SARS-CoV-2 RBD comprises an amino acid sequence having at least 90% identity to the sequence corresponding to SEQ ID NO:24, wherein from 1 to 10 amino acids located at positions 1-10 in reference to the sequence corresponding to SEQ ID NO:24 are not comprised within the SARS-CoV-2 RBD amino acid sequence (or a smaller range as recited above), and wherein from 1 to 10 amino acids located at positions 228-237 in reference to the sequence corresponding to SEQ ID NO:24 are not comprised within the SARS-CoV-2 RBD amino acid sequence (or a smaller range as recited above).

In certain embodiments, the amino acid at the C-terminus of SARS-CoV-2 RBD is lysine (K). In certain embodiments, the last seven amino acids at the C-terminus of the SARS-CoV-2 RBD is KSTNLVK (SEQ ID NO: 31). In certain embodiments, the last six amino acids at the C-terminal of the SARS-CoV-2 RBD is STNLVK (SEQ ID NO: 32). For example, in certain embodiments, the SARS-CoV-2 RBD amino acid sequence ends with a segment of STNLVK (SEQ ID NO: 32) at the C-terminus.

In certain embodiments, the last seven amino acids at the C-terminus of the SARS-CoV-2 RBD is not NKCVNFS (SEQ ID NO: 33). In certain embodiments, the last six amino acids at the C-terminus of the SARS-CoV-2 RBD is not NKCVNF (SEQ ID NO: 34). For example, in certain embodiments, the SARS-CoV-2 RBD does not end with a segment of NKCVNFS (SEQ ID NO: 33) or NKCVNF (SEQ ID NO: 34) at the C-terminus.

In certain embodiments, 1, 2, 3, 4, 5, 6, 7, 8, 9 or 10 amino acids located at positions 1-10 in reference to SEQ ID NO:1 are not comprised within the SARS-CoV-2 RBD amino acid sequence. In certain embodiments, 1, 2, 3, 4, 5, 6, 7, 8, 9 or 10 amino acids located at positions 208-217 in reference to SEQ ID NO:1 are not comprised within the SARS-CoV-2 RBD amino acid sequence.

In certain embodiments, the SARS-CoV-2 RBD comprises an amino acid sequence having at least 90% identity to the sequence corresponding to SEQ ID NO: 1, wherein from 1 to 10 amino acids located at positions 1-10 in reference to the sequence corresponding to SEQ ID NO:1 are not comprised within the SARS-CoV-2 RBD amino acid sequence. In certain embodiments, from 1 to 9 (e.g., consecutive) amino acids located at positions 1-9; or from 1 to 8 (e.g., consecutive) amino acids located at positions 1-8; or from 1 to 7 (e.g., consecutive) amino acids located at positions 1-7; or from 1 to 6 (e.g., consecutive) amino acids located at positions 1-6; or from 1 to 5 (e.g., consecutive) amino acids located at positions 1-5; or from 1 to 4 (e.g., consecutive) amino acids located at positions 1-4; or from 1 to 3 (e.g., consecutive) amino acids located at positions 1-3; or from 1 to 2 (e.g., consecutive) amino acids located at positions 1-2; or 1 amino acid located at position 1, in reference to the sequence corresponding to SEQ ID NO:1 are not comprised within the SARS-CoV-2 RBD amino acid sequence.

In certain embodiments, the SARS-CoV-2 RBD comprises an amino acid sequence having at least 90% identity to the sequence corresponding to SEQ ID NO: 1, wherein from 1 to 10 (e.g., consecutive) amino acids located at positions 208-217 in reference to the sequence corresponding to SEQ ID NO:1 are not comprised within the SARS-CoV-2 RBD amino acid sequence. In certain embodiments, from 1 to 9 (e.g., consecutive) amino acids located at positions 209-217; or from 1 to 8 (e.g., consecutive) amino acids located at positions 210-217; or from 1 to 7 (e.g., consecutive) amino acids located at positions 211-217; or from 1 to 6 (e.g., consecutive) amino acids located at positions 212-217; or from 1 to 5 (e.g., consecutive) amino acids located at positions 213-217; or from 1 to 4 (e.g., consecutive) amino acids located at positions 214-217; or from 1 to 3 (e.g., consecutive) amino acids located at positions 215-217; or from 1 to 2 (e.g., consecutive) amino acids located at positions 216-217; or 1 amino acid located at position 217, in reference to the sequence corresponding to SEQ ID NO:1 are not comprised within the SARS-CoV-2 RBD amino acid sequence.

In certain embodiments, the SARS-CoV-2 RBD comprises an amino acid sequence having at least 90% identity to the sequence of SEQ ID NO:1, and wherein from 1 to 10 amino acids located at positions 1-10 in reference to the sequence corresponding to SEQ ID NO:1 are not comprised within the SARS-CoV-2 RBD amino acid sequence (or a smaller range as recited above), and wherein from 1 to 10 amino acids located at positions 208-217 in reference to the sequence corresponding to SEQ ID NO:1 are not comprised within the SARS-CoV-2 RBD amino acid sequence (or a smaller range as recited above).

In certain embodiments, the SARS-CoV-2 RBD comprises an amino acid sequence having at least 90% identity to a sequence corresponding to SEQ ID NO:25. In certain embodiments, the SARS-CoV-2 RBD further comprises from 1 to 10 (e.g., consecutive) amino acids provided in a sequence corresponding to SEQ ID NO:26. For example, in certain embodiments, the SARS-CoV-2 RBD the amino-terminus comprises RVQPTESIVR (SEQ ID NO: 26), VQPTESIVR (SEQ ID NO: 35), QPTESIVR (SEQ ID NO: 36), PTESIVR (SEQ ID NO: 37), TESIVR (SEQ ID NO: 38), ESIVR (SEQ ID NO: 39), SIVR (SEQ ID NO: 40), IVR, VR, or R. In certain embodiments, the SARS-CoV-2 RBD further comprises from 1 to 10 amino acids provided in a sequence corresponding to SEQ ID NO:27. In certain embodiments, the SARS-CoV-2 RBD carboxy-terminus comprises GPKKSTNLVK (SEQ ID NO: 27), GPKKSTNLV (SEQ ID NO: 41), GPKKSTNL (SEQ ID NO: 42), GPKKSTN (SEQ ID NO: 43), GPKKST (SEQ ID NO: 44), GPKKS (SEQ ID NO: 45), GPKK (SEQ ID NO: 46), GPK, GP, or G. In certain embodiments, the SARS-CoV-2 RBD further comprises 1 to 10 amino acids provided in a sequence corresponding to SEQ ID NO:26, and further comprises from 1 to 10 amino acids provided in a sequence corresponding to SEQ ID NO:27. In certain embodiments, the SARS-CoV-2 RBD the amino-terminus comprises RVQPTESIVR (SEQ ID NO: 26), VQPTESIVR (SEQ ID NO: 35), QPTESIVR (SEQ ID NO: 36), PTESIVR (SEQ ID NO: 37), TESIVR (SEQ ID NO: 38), ESIVR (SEQ ID NO: 39), SIVR (SEQ ID NO: 40), IVR, VR, or R and the carboxy-terminus comprises GPKKSTNLV (SEQ ID NO: 41), GPKKSTNL (SEQ ID NO: 42), GPKKSTN (SEQ ID NO: 43), GPKKST (SEQ ID NO: 44), GPKKS (SEQ ID NO: 45), GPKK (SEQ ID NO: 46), GPK, GP, or G.

In certain embodiments, the SARS-CoV-2 RBD comprises an amino acid sequence having at least 90% identity to a sequence corresponding to SEQ ID NO:1. In certain embodiments, the SARS-CoV-2 RBD further comprises from 1 to 10 amino acids provided in the sequence corresponding to SEQ ID NO:28. For example, in certain embodiments, the SARS-CoV-2 RBD the amino-terminus comprises EKGIYQTSNF (SEQ ID NO: 28), KGIYQTSNF (SEQ ID NO: 47), GIYQTSNF (SEQ ID NO: 48), IYQTSNF (SEQ ID NO: 49), YQTSNF (SEQ ID NO: 50), QTSNF (SEQ ID NO: 51), TSNF (SEQ ID NO: 52), SNF, NF or F. In certain embodiments, the SARS-CoV-2 RBD further comprises from 1 to 10 amino acids provided in the sequence corresponding to SEQ ID NO:29. In certain embodiments, the SARS-CoV-2 RBD carboxy-terminus comprises NKCVNFNFNG (SEQ ID NO: 29), NKCVNFNFN (SEQ ID NO: 53), NKCVNFNF (SEQ ID NO: 54), NKCVNFN (SEQ ID NO: 55), NKCVNF (SEQ ID NO: 34), NKCVN (SEQ ID NO: 56), NKCV (SEQ ID NO: 57), NKC, NK, or N. In certain embodiments, the SARS-CoV-2 RBD further comprises 1 to 10 amino acids provided in the sequence corresponding to SEQ ID NO:28, and further comprises from 1 to 10 amino acids provided in the sequence corresponding to SEQ ID NO:29. In certain embodiments, the SARS-CoV-2 RBD the amino-terminus comprises EKGIYQTSNF (SEQ ID NO: 28), KGIYQTSNF (SEQ ID NO: 47), GIYQTSNF (SEQ ID NO: 48), IYQTSNF (SEQ ID NO: 49), YQTSNF (SEQ ID NO: 50), QTSNF (SEQ ID NO: 51), TSNF (SEQ ID NO: 52), SNF, NF or F, and the carboxy-terminus comprises NKCVNFNFN (SEQ ID NO: 53), NKCVNFNF (SEQ ID NO: 54), NKCVNFN (SEQ ID NO: 55), NKCVNF (SEQ ID NO: 34), NKCVN (SEQ ID NO: 56), NKCV (SEQ ID NO: 57), NKC, NK, or N.

Fc (Fragment Crystallizable) Domain

In certain embodiments, the Fc domain amino acid sequence comprises a human Fc domain amino acid sequence. In certain embodiments, the Fc domain amino acid sequence comprises a human IgG1, IgG2, IgG3 or IgG4 Fc domain amino acid sequence. In certain embodiments, the Fc domain amino acid sequence comprises a human IgG1, IgG2 or IgG4 Fc domain amino acid sequence. In certain embodiments, the Fc domain amino acid sequence comprises a human IgG4 Fc domain amino acid sequence.

In certain embodiments, the Fc domain amino acid sequence comprises an amino acid sequence having at least about 80% identity to SEQ ID NO:4. In certain embodiments, the Fc domain amino acid sequence comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:4. In certain embodiments, the Fc domain amino acid sequence comprises an amino acid sequence having at least about 85% sequence identity to SEQ ID NO:4. In certain embodiments, the Fc domain amino acid sequence comprises an amino acid sequence having at least about 90% sequence identity to SEQ ID NO:4. In certain embodiments, the Fc domain amino acid sequence comprises an amino acid sequence having at least about 95% sequence identity to SEQ ID NO:4. In certain embodiments, the Fc domain amino acid sequence comprises an amino acid sequence having at least about 99% sequence identity to SEQ ID NO:4. In certain embodiments, the Fc domain amino acid sequence comprises SEQ ID NO:4 In certain embodiments, the Fc domain amino acid sequence consists of SEQ ID NO: 4.

Linker Group, Tag and Signal Peptide

In certain embodiments, elements within the antigen-Fc polypeptide (e.g., S-antigen-Fc polypeptide) are directly linked to each other (e.g., through a peptide bond). For example, in certain embodiments, the SARS-CoV-2 Spike protein domain amino acid sequence is directly linked to the Fc domain amino acid sequence (e.g., through a peptide bond).

In certain embodiments, the antigen-Fc polypeptide further comprises one or more linker group(s). Such a linker group may be used to link together elements present in the antigen-Fc polypeptide. The nature of the linker group is not critical, provided that the linker group does not interfere with the function of the antigen-Fc polypeptide or elements comprised within the polypeptide that are being linked together.

In certain embodiments, the antigen amino acid sequence (e.g., a SARS-CoV-2 Spike protein domain sequence) is operably linked to the Fc domain amino acid sequence via a linker group (e.g., the antigen amino acid sequence is linked to the N-terminus of the Fc domain sequence). In certain embodiments, the linker group is an amino acid sequence (e.g., a sequence described herein). In certain embodiments, the linker group amino acid sequence is between about 1 to about 25 amino acids in length, or about 1 to about 20 amino acids in length, or about 1 to about 15 amino acids in length, or about 1 to about 10 amino acids in length (e.g., 1, 2, 3, 4, 5, 6, 7, 8, 9 or 10 amino acids in length). In certain embodiments, the linker group sequence comprises an amino acid sequence having at least about 80% sequence identity to SEQ ID NO:8. In certain embodiments, the linker group sequence comprises an amino acid sequence having at least about 85% sequence identity to SEQ ID NO:8. In certain embodiments, the linker group sequence comprises an amino acid sequence having at least about 90% sequence identity to SEQ ID NO:8. In certain embodiments, the linker group sequence comprises an amino acid sequence having at least about 95% sequence identity to SEQ ID NO:8. In certain embodiments, the linker group sequence comprises SEQ ID NO:8. In certain embodiments, the linker group sequence consists of SEQ ID NO:8.

In certain embodiments, the antigen-Fc polypeptide further comprises an affinity tag (e.g., poly(His) tag or a myc tag). The location of the affinity tag is not critical, provided that it does not interfere with the function of the antigen amino acid sequence or the Fc binding domain amino acid sequence. In certain embodiments, the affinity tag operably linked to the N-terminus or C-terminus of the antigen-Fc polypeptide. In certain embodiments, the affinity tag is included within the antigen-Fc polypeptide (i.e., not at either terminus). In certain embodiments the affinity tag is operably linked to the N-terminus of the antigen amino acid sequence (e.g., at the N-terminus of the Spike protein domain amino acid sequence).

In certain embodiments, the affinity tag is operably linked to the antigen amino acid sequence (e.g., the Spike protein domain amino acid sequence) via a direct bond (e.g., a peptide bond).

In certain embodiments, the affinity tag is operably linked to the antigen amino acid sequence (e.g., the Spike protein domain amino acid sequence) via a linker group. In certain embodiments, the linker group is an amino acid sequence such as a linker group amino acid sequence described herein. In certain embodiments, the linker group amino acid sequence is between about 1 to about 25 amino acids in length, or about 1 to about 20 amino acids in length, or about 1 to about 15 amino acids in length, or about 1 to about 10 amino acids in length (e.g., 1, 2, 3, 4, 5, 6, 7, 8, 9 or 10 amino acids in length). In certain embodiments, the linker group sequence comprises an amino acid sequence having at least about 80% sequence identity to SEQ ID NO: 9. In certain embodiments, the linker group sequence comprises an amino acid sequence having at least about 85% sequence identity to SEQ ID NO: 9. In certain embodiments, the linker group sequence comprises an amino acid sequence having at least about 90% sequence identity to SEQ ID NO: 9. In certain embodiments, the linker group sequence comprises an amino acid sequence having at least about 95% sequence identity to SEQ ID NO: 9. In certain embodiments, the linker group sequence comprises SEQ ID NO:9. In certain embodiments, the linker group sequence consists of SEQ ID NO:9.

In certain embodiments, the antigen-Fc polypeptide further comprises a signal peptide. In certain embodiments, the signal peptide is tPA signal peptide. In certain embodiments, the signal peptide is cleaved from the polypeptide prior to secretion. In some embodiments, the antigen-Fc polypeptide does not include a signal peptide.

In certain embodiments, the signal peptide is operably linked to the N-terminus of the antigen-Fc polypeptide amino acid sequence.

In certain embodiments, the signal peptide is directly linked to the antigen-Fc polypeptide amino acid sequence (e.g., directly linked to an affinity tag or directly linked to the antigen amino acid sequence). In certain embodiments, the signal peptide is linked to the antigen-Fc polypeptide amino acid sequence through a linker group (e.g., an amino acid linker group).

Thus, in certain embodiments, the antigen-Fc polypeptide may further comprise one or more linker group(s), an affinity tag(s) and/or a signal peptide sequence.

In certain embodiments, the S-antigen-Fc polypeptide comprises an amino acid sequence having at least about 80% identity to SEQ ID NO:5, 6, 7, or 21. In certain embodiments, the S-antigen-Fc polypeptide comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:5, 6, 7, or 21. In certain embodiments, the S-antigen-Fc polypeptide comprises an amino acid sequence having at least about 85% sequence identity to SEQ ID NO:5, 6, 7, or 21. In certain embodiments, the S-antigen-Fc polypeptide comprises an amino acid sequence having at least about 90% sequence identity to SEQ ID NO:5, 6, 7, or 21. In certain embodiments, the S-antigen-Fc polypeptide comprises an amino acid sequence having at least about 95% sequence identity to SEQ ID NO:5, 6, 7, or 21. In certain embodiments, the S-antigen-Fc polypeptide comprises an amino acid sequence having at least about 99% sequence identity to SEQ ID NO:5, 6, 7, or 21. In certain embodiments, the S-antigen-Fc polypeptide comprises SEQ ID NO:5. In certain embodiments, the S-antigen-Fc polypeptide consists of SEQ ID NO:5. In certain embodiments, the S-antigen-Fc polypeptide comprises SEQ ID NO:6. In certain embodiments, the S-antigen-Fc polypeptide consists of SEQ ID NO:6. In certain embodiments, the S-antigen-Fc polypeptide comprises SEQ ID NO:7. In certain embodiments, the S-antigen-Fc polypeptide consists of SEQ ID NO:7. In certain embodiments, the S-antigen-Fc polypeptide comprises SEQ ID NO:21. In certain embodiments, the S-antigen-Fc polypeptide consists of SEQ ID NO:21.

The length of the antigen-Fc polypeptide will vary, e.g., depending on the antigen selected. However, in certain embodiments, the antigen-Fc polypeptide is between about 197 to about 2,500 amino acids in length. In certain embodiments, the antigen-Fc polypeptide is between about 197 to about 2,000 amino acids in length. In certain embodiments, the antigen-Fc polypeptide is between about 197 to about 1,500 amino acids in length. In certain embodiments, the antigen-Fc polypeptide is between about 197 to about 1,000 amino acids in length. In certain embodiments, the antigen-Fc polypeptide is between about 197 to about 750 amino acids in length. In certain embodiments, the antigen-Fc polypeptide is between about 197 to about 500 amino acids in length.

In certain embodiments, the antigen-Fc polypeptide is between about 400 and about 500 amino acids in length. In certain embodiments, the antigen-Fc polypeptide is between about 425 and about 500 amino acids in length. In certain embodiments, the antigen-Fc polypeptide is between about 425 and about 485 amino acids in length. In certain embodiments, the antigen-Fc polypeptide is between about 440 and about 480 amino acids in length. In certain embodiments, the antigen-Fc polypeptide is between about 440 and about 455 amino acids in length. In certain embodiments, the antigen-Fc polypeptide is between about 445 and about 449 amino acids in length. In certain embodiments, the antigen-Fc polypeptide is about 447 amino acids in length. In certain embodiments, the antigen-Fc polypeptide is between about 460 and about 480 amino acids in length. In certain embodiments, the antigen-Fc polypeptide is between about 468 and about 472 amino acids in length. In certain embodiments, the antigen-Fc polypeptide is about 470 amino acids in length.

In certain embodiments, the antigen-Fc polypeptide is between about 850 and about 950 amino acids in length. In certain embodiments, the antigen-Fc polypeptide is between about 870 and about 925 amino acids in length. In certain embodiments, the antigen-Fc polypeptide is between about 885 and about 925 amino acids in length. In certain embodiments, the antigen-Fc polypeptide is between about 892 and about 894 amino acids in length. In certain embodiments, the antigen-Fc polypeptide is about 894 amino acids in length. In certain embodiments, the antigen-Fc polypeptide is between about 907 and about 927 amino acids in length. In certain embodiments, the antigen-Fc polypeptide is between about 915 and about 919 amino acids in length. In certain embodiments, the antigen-Fc polypeptide is about 917 amino acids in length.

In certain embodiments, the antigen-Fc polypeptide is at least about 400, 425, 447, 470, 500, 550, 600, 650, 700, 750, 800, 850, 894, 900, or 917 amino acids in length.

In certain embodiments, the antigen-Fc polypeptide comprises a spike RBD amino acid sequence but does not comprise other spike protein domains. For example, in certain embodiments the antigen-Fc polypeptide does not comprise an N-terminal domain, an S2 domain, a transmembrane domain, and/or an intracellular domain. In certain embodiments the antigen-Fc polypeptide does not comprise the following spike protein domains: an N-terminal domain, an S2 domain, a transmembrane domain, and an intracellular domain. In certain embodiments, the antigen-Fc polypeptide is a SARS-COV-2 RBD amino acid sequence (e.g., an RBD amino acid sequence described herein) operably linked to a Fc domain amino acid sequence (e.g., a human IgG1, IgG2, IgG3 or IgG4 Fc domain amino acid sequence). In certain embodiments, the antigen-Fc polypeptide consists of a SARS-CoV-2 RBD amino acid sequence (e.g., an RBD amino acid sequence described herein) linked directly or through a linker group to a Fc domain amino acid sequence (e.g., a human IgG1, IgG2, IgG3 or IgG4 Fc domain amino acid sequence). In certain embodiments, the signal peptide is operably linked to the N-terminus of the antigen-Fc polypeptide amino acid sequence.

Nucleic Acids, Expression Cassettes and Vectors

In some embodiments, the polypeptides described herein are prepared using recombinant methods. Accordingly, certain embodiments provide polynucleotides (e.g., isolated polynucleotides) comprising a nucleic acid sequence encoding any of the polypeptides described herein. The polynucleotides may be single-stranded or double-stranded. In some embodiments, the polynucleotide is DNA. In some embodiments, the polynucleotide is cDNA. In some embodiments, the polynucleotide is RNA. In some embodiments, the polynucleotide comprises a nucleic acid sequence that has at least about 90% (e.g., at least about 90%, 91%, 92%, 93%, 94%, 95%, 96%, 97%, 98%, 99% or 100%) sequence identity to SEQ ID NO: 18, 19, 20, or 23.

In certain embodiments, the nucleic acid further comprises a promoter.

Certain embodiments of the invention provide an expression cassette comprising a nucleic acid sequence described herein and a promoter operably linked to the nucleic acid.

In certain embodiments, the promoter is a regulatable promoter. In certain embodiments, the promoter is a constitutive promoter.

In certain embodiments, the expression cassette further comprises an expression control sequence (e.g., an enhancer) operably linked to the nucleic acid sequence. Expression control sequences and techniques for operably linking sequences together are well known in the art.

Nucleic acids/expression cassettes encoding a polypeptide described herein can be engineered into a vector using standard ligation techniques, such as those described in Sambrook and Russell, Molecular Cloning: A Laboratory Manual, Cold Spring Harbor Laboratory Press Cold Spring Harbor, NY (2001). For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration).

Accordingly, certain embodiments of the invention provide a vector comprising an expression cassette described herein. In particular, certain embodiments provide a vector comprising an expression cassette comprising a promoter operably linked to a nucleic acid sequence encoding a polypeptide as described herein.

Non-limiting examples of vectors include plasmids and viral expression systems, such as a lentiviral, adenoviral, and adeno-associated virus (AAV) expression systems. Further non-limiting examples mammalian expression vectors include the pRc/CMV, pSV2gpt, pSV2neo, pcDNA3, pcDNAI/amp, pcDNAI/neo, pSV2-dhfr, pMSG, pSVT7, pTk2, pRSVneo, pko-neo, and pHyg-derived vectors. In certain embodiments, the vector is a lentivirus vector. In certain embodiments, the vector is a vector described herein. In certain embodiments, the vector is pCMV SPORT vector.

Cells

Certain embodiments of the invention provide a cell comprising a polypeptide described herein, a nucleic acid described herein, an expression cassette described herein, or a vector described herein.

In certain embodiments, the cell is a mammalian cell.

In certain embodiments, the cell is a human mammalian cell. In certain embodiments, the cell is a human embryonic kidney (HIEK) 293 cell. In certain embodiments, the cell is a 293F cell. In certain embodiments, the cell is a 293T cell. In certain embodiments, the cell is a human embryonic retinal (PER.C6) cell. In certain embodiments, the cell is a HT-1080 cell. In certain embodiments, the cell is a Huh-7 cell.

In certain embodiments, the cell is a non-human mammalian cell. In certain embodiments, the cell is a Monkey kidney epithelial (Vero) cell. In certain embodiments, the cell is a Chinese Hamster Ovary (CHO) cell. In certain embodiments, the cell is a baby hamster kidney (BHK) cell.

In certain embodiments, the cell is a non-mammalian cell. In certain embodiments, the cell is an insect cell. In certain embodiments, the cell is a yeast cell. In certain embodiments, the cell is a bacteria cell (e.g., *E. coli* cells such as BL21 cells).

Certain embodiments provide a cell produced using a method described herein. For example, certain embodiments of the invention provide a method of making a genetically modified cell capable of producing a polypeptide described herein, the method comprising transfecting or transducing a cell with a nucleic acid, expression cassette or vector described herein. In certain embodiments, the vector comprises a selectable marker. In certain embodiments, the vector is a lentivirus vector.

Certain embodiments also provide a method of producing a polypeptide described herein, comprising transfecting or transducing a cell with a nucleic acid, expression cassette or vector described herein. In certain embodiments, the vector comprises a selectable marker. In certain embodiments, the vector is a lentivirus vector.

In certain embodiments, a method described herein may be used to produce a polypeptide as described herein 1) that is biologically active and/or 2) which is properly folded.

In certain embodiments, a cell described herein is capable of producing a high yield of a polypeptide described herein. For example, in certain embodiments, the cell is capable of producing at least about 30 mg/liter cell culture of the polypeptide. In certain embodiments, the cell is capable of producing at least about 35 mg/liter cell culture of the polypeptide. In certain embodiments, the cell is capable of producing at least about 40 mg/liter cell culture of the polypeptide. In certain embodiments, the cell is capable of producing at least about 45 mg/liter cell culture of the polypeptide. In certain embodiments, the cell is capable of producing at least about 50 mg/liter cell culture of the polypeptide. In certain embodiments, the cell is capable of producing at least about 55 mg/liter cell culture of the polypeptide. In certain embodiments, the cell is capable of producing at least about 60 mg/liter cell culture of the polypeptide. In certain embodiments, the cell is capable of producing at least about 65 mg/liter cell culture of the polypeptide. In certain embodiments, the cell is capable of producing at least about 70 mg/liter cell culture of the polypeptide. In certain embodiments, the cell is capable of producing about 30 mg/liter cell culture to about 70 mg/liter cell culture of the polypeptide. In certain embodiments, the cell is capable of producing about 35 mg/liter cell culture to about 65 mg/liter cell culture of the polypeptide. In certain embodiments, the cell is capable of producing about 40 mg/liter cell culture to about 60 mg/liter cell culture of the polypeptide.

Compositions

Certain embodiments of the invention provide a composition comprising a polypeptide as described herein or a VLP as described herein and a carrier. For example, certain embodiments of the invention provide a composition comprising
  a) a VLP monomer polypeptide as described herein,
  b) a S-antigen-Fc polypeptide, or a multimer thereof, as described herein, and/or
  c) a VLP or a VLP scaffold as described herein, and a carrier.

In certain embodiments, the composition comprises a VLP scaffold as described herein.

In certain embodiments, the composition comprises a VLP as described herein.

In certain embodiments, the composition comprises a S-antigen-Fc polypeptide, or a multimer thereof, as described herein. For example, in certain embodiments, the composition comprises a S-antigen-Fc polypeptide comprising a SARS-CoV-2 Spike protein domain amino acid sequence linked directly or through a linker group to a Fc domain amino acid sequence, wherein the SARS-CoV-2 Spike protein domain amino acid sequence is a SARS-CoV-2 receptor binding domain (RBD) amino acid sequence, and wherein the Fc domain amino acid sequence comprises a human IgG1, IgG2, IgG3 or IgG4 Fc domain amino acid sequence.

In certain embodiments, the VLP is a multi-antigen VLP (e.g., comprises a combination of SARS CoV-2 S1-Fc and SARS CoV-2 RBD-Fc polypeptides).

In certain embodiments, the VLP is a single-antigen VLP, wherein only one type of antigen-Fc polypeptide is present in the VLP (e.g., displayed on the VLP scaffold). In certain embodiments, only SARS CoV-2 S1-Fc is present in a single VLP. In certain embodiments, only SARS CoV-2 RBD-Fc is present in a single VLP.

In certain embodiments, once generated, different types of single-antigen VLPs can be mixed together to produce a composition comprising two or more distinct types of single-antigen VLPs.

For example, in certain embodiments, the composition comprises:

a first single-antigen VLP comprising a first S-antigen-Fc polypeptide as described herein and a second single-antigen VLP comprising a second S-antigen-Fc polypeptide as described herein.

In certain embodiments, the first S-antigen-Fc polypeptide amino acid comprises a SARS-CoV-2 S1 amino acid sequence as described herein, and the second S-antigen-Fc polypeptide amino acid comprises a SARS-CoV-2 RBD amino acid sequence as described herein.

In certain embodiments, the composition is a pharmaceutical composition comprising a pharmaceutically acceptable carrier.

In certain embodiments, the composition is a vaccine composition. In certain embodiments, the composition is a liquid composition. In certain embodiments, the vaccine composition is an emulsion formulation. In certain embodiments, the composition is a lyophilized composition that further comprises one or more excipients selected from the group consisting of a cryo-lyoprotectant (e.g., trehalose, sucrose) and a bulking agent (e.g., mannitol, glycine).

Vaccines of the Invention

As described herein, the present invention also provides vaccine compositions (e.g., comprising a polypeptide or VLP as described herein), and methods of vaccination (e.g., effective to immunize a susceptible animal (e.g., a mammal, such as a human) against a coronavirus infection (e.g., a SARS-CoV-2 infection)).

Certain embodiments of the invention provide a vaccine composition comprising a VLP as described herein and a pharmaceutically acceptable carrier. Certain embodiments of the invention also provide a vaccine composition comprising an S-antigen-Fc polypeptide as described herein and a pharmaceutically acceptable carrier. For example, in certain embodiments, the vaccine composition comprises a S-antigen-Fc polypeptide comprising a SARS-CoV-2 Spike protein domain amino acid sequence linked directly or through a linker group to a Fc domain amino acid sequence, wherein the SARS-CoV-2 Spike protein domain amino acid sequence is a SARS-CoV-2 receptor binding domain (RBD) amino acid sequence, and wherein the Fc domain amino acid sequence comprises a human IgG1, IgG2, IgG3 or IgG4 Fc domain amino acid sequence.

In certain embodiments, the vaccine composition further comprises one or more adjuvants.

The term "adjuvant" as used herein refers to non-specific stimulators of the immune response or substances that allow generation of a depot in the host, which when combined with the vaccine and pharmaceutical composition, respectively, of the present invention may provide for an even more enhanced immune response. Vaccines commonly contain two components: antigen and adjuvant. The antigen is the molecular structure encoded by the pathogen against which the immune response is directed. To activate an antigen-specific immune response, the antigen must be presented in the appropriate immunostimulatory microenvironment. In certain embodiments, adjuvants establish such microenvironments by stimulating the production of immune-activating molecules such as proinflammatory cytokines. Vaccine efficacy depends on the types of antigen and adjuvant, and how they are administered.

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-α, 1-β, 2, 4, 5, 6, 7, 8 and 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE); oil-in-water emulsions, such as MF59 (U.S. Pat. No. 6,299,884) (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, MA)), and SAF (containing 10% Squalene, 0.4% Tween 80, 5% pluronic-blocked polymer L121, and thr-MDP, either microfluidized into a submicron emulsion or vortexed to generate a larger particle size emulsion); aluminum salts (alum), such as aluminum hydroxide, aluminum phosphate, aluminum sulfate; Amphigen; Avridine; L121/squalene; D-lactide-polylactide/glycoside; pluronic polyols; killed *Bordetella*; saponins, such as Stimulon™ QS-21 (Antigenics, Framingham, MA.), described in U.S. Pat. No. 5,057,540, ISCOMATRIX (CSL Limited, Parkville, Australia), described in U.S. Pat. No. 5,254,339, and immunostimulating complexes (ISCOMS); *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

Suitable adjuvants used to enhance an immune response further include, without limitation, MPL™ (3-O-deacylated monophosphoryl lipid A, Corixa, Hamilton, MT), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, MT), and which are described in U.S. Pat. No. 6,113,918. One such AGP is 2-[(R)-3-Tetradecanoyloxytetradecanoylamino] ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Suitable adjuvants also include, but are not limited to, surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.*, 30:3-15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

In certain embodiments, the adjuvant comprises aluminum salt (e.g., aluminum hydroxide, aluminum phosphate, alum (e.g., potassium aluminum sulfate), or mixed aluminum salts). In certain embodiments, the adjuvant comprises a Toll like receptor agonist (e.g., monophosphoryl lipid A (MPL-A), a lipopeptide, and a synthetic nucleic acid sequence such as CpG and poly(I:C)). In certain embodiments, the adjuvant comprises squalene. In certain embodiments, the adjuvant comprises ASO4.

In certain embodiments, the adjuvant comprises Complete Freund's Adjuvant (CFA). In certain embodiments, the adjuvant comprises Incomplete Freund's Adjuvant (IFA). In certain embodiments, the adjuvant comprises aluminum salt (e.g., Alum). In certain embodiments, the adjuvant comprises monophosphoryl lipid A. In certain embodiments, the adjuvant comprises aluminum salt (e.g., Alum) and monophosphoryl lipid A.

A polypeptide described herein can be conjugated or linked to another peptide or to a polysaccharide. For example, immunogenic proteins well-known in the art, also known as "carriers," may be employed. Useful immunogenic proteins include keyhole limpet hemocyanin (KLH), bovine serum albumin (BSA), ovalbumin, human serum albumin, human gamma globulin, chicken immunoglobulin G and bovine gamma globulin. Useful immunogenic polysaccharides include polysaccharides from other pathogens, such as those that are effective as vaccines. The immunogenic polysaccharides or proteins of other pathogens can be conjugated to, linked to, or mixed with the polypeptide described herein.

To prepare a vaccine, a polypeptide described herein can be isolated, lyophilized and stabilized. The polypeptide described herein may then be adjusted to an appropriate concentration, optionally combined with a suitable vaccine adjuvant, and packaged for use.

In certain embodiments, the present invention comprises two or more immunogenic polypeptides. In certain embodiments, one or more polypeptides are adjusted to an appropriate concentration and can be formulated with any suitable adjuvant, diluent, pharmaceutically acceptable carrier, or any combination thereof. As used herein the phrase "pharmaceutically acceptable carrier" is intended to include any and all solvents, dispersion media, coatings, antibacterial and antifungal agents, isotonic and absorption delaying agents, excipients and the like, compatible with pharmaceutical administration. The use of such media and agents for pharmaceutically active substances is well known in the art. Physiologically acceptable vehicles may be used as carriers and/or diluents. A pharmaceutically acceptable vehicle is understood to designate a compound or a combination of compounds entering into a pharmaceutical or immunogenic composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen. These include, but are not limited to, water, Ringer's solution, an appropriate isotonic medium, glycerol, ethanol and other conventional solvents, phosphate buffered saline, and the like.

As used herein, the term "therapeutic agent" or "therapeutic complex" refers to any agent or material that has a beneficial effect on the mammalian recipient. Thus, "therapeutic agent" embraces both therapeutic and prophylactic molecules having nucleic acid or protein components.

"Antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. An antigen can have one or more epitopes (B- and/or T-cell epitopes). Antigens as used herein may also be mixtures of several individual antigens. "Antigenic determinant" refers to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

The term, "antibody", is used herein in the broadest sense and specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., SARS-CoV-2 binding and or neutralizing.

An "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier. Preferably, antigen presenting cell may be activated.

A substance that "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In certain embodiments, the immune response in enhanced by a factor of at least about 2, such as by a factor of about 3 or more. The amount or type of cytokines secreted may also be altered. Alternatively, the amount of antibodies induced or their subclasses may be altered.

The terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

The term "immunotherapeutic" refers to a composition for the treatment of diseases, disorders or conditions. More specifically, the term is used to refer to a method of treatment wherein a beneficial immune response is generated by vaccination or by transfer of immune molecules. An "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition, the antigen, the route of immunization, the individual, the prior immune or physiologic state etc.

The term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes. As used herein "correspond essentially to" refers to an epitope that will elicit an immunological response at least substantially equivalent to the response generated by the native epitope. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response. An "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount." The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Methods of Use

Certain embodiments of the invention also provide a method of immunizing an animal for the prevention of an infection, such as a SARS-CoV-2 infection, comprising administering to the animal a first dose of an effective amount of a VLP or composition as described herein.

Certain embodiments also provide a method of treating or preventing an infection in an animal (e.g., a mammal, such as a human) comprising administering to the animal an effective amount of a VLP or composition described herein.

In certain embodiments, the infection is a coronavirus infection. In certain embodiments, the infection is a SARS-CoV-1 infection. In certain embodiments, the infection is a SARS-CoV-1-like bat coronavirus infection (e.g., bat coronavirus SHC014 infection). In certain embodiments, the infection is a SARS-CoV-2 infection. In certain embodiments, the SARS-CoV-2 infection is caused by a wild-type SARS-CoV-2 strain or variant thereof. For example, in certain embodiments, the variant is a variant as described in Garcia-Beltran W F, et al. (2021) *Cell.* 2021; 184(9):2372-83, which is incorporated by reference herein for all purposes. In certain embodiments, the SARS-CoV-2 variant comprises one or more spike protein mutations selected from the group consisting of L18F, T20N, P26S, D138Y, R190S, D80A, D215G, R246I, H655Y, A701V, T716I, S982A, T1027I, D1118H, V1176F, K417T/N, E484K, N501Y, V367F, G476S, G485R, H519Q and D614G. In certain embodiments, the SARS-CoV-2 variant comprises one or more spike protein mutations selected from the group consisting of K417T/N, E484K, N501Y, V367F, G476S, G485R, H519Q and D614G. In certain embodiments, the SARS-CoV-2 variant is P.1 strain, or its derivative strain thereof, comprising K417T, E484K, and N501Y. In certain embodiments, the SARS-CoV-2 variant is B.1.1.7 strain, or its derivative strain thereof, comprising N501Y. In certain embodiments, the SARS-CoV-2 variant is B.1.351 strain, or its derivative strain thereof, comprising K417N, E484K, and N501Y.

Certain embodiments also provide a method for eliciting a neutralizing antibody response (e.g., a coronavirus neutralizing antibody response) in an animal (e.g., a mammal, such as a human) comprising administering to the animal an effective amount of a VLP or composition described herein. In certain embodiments, the neutralizing antibody response blocks Spike protein-ACE2 binding. In certain embodiments, the neutralizing antibody response prevents cell entry of a pathogen (e.g., a coronavirus). In certain embodiments, the neutralizing antibody response is an IgG neutralizing antibody response (e.g., IgG coronavirus neutralizing antibody response). In certain embodiments, the neutralizing antibody response is an IgA neutralizing antibody response (e.g., an IgA coronavirus neutralizing antibody response). In certain embodiments, the neutralizing antibody response is an IgG and IgA neutralizing antibody response. In certain embodiments, the neutralizing antibody response is a SARS-CoV-1 response, a SARS-CoV-1-like bat coronavirus response (e.g., bat coronavirus SHC014 infection) or a SARS-CoV-2 response (e.g., a wildtype strain or variant thereof, such as variant described herein).

Certain embodiments also provide a method of treating or preventing a SARS-CoV-2 infection (e.g., a wildtype strain or a variant thereof) in an animal (e.g., a mammal, such as a human) comprising administering to the animal an effective amount of a VLP or composition described herein.

Certain embodiments also provide a method for eliciting a SARS-CoV-2 (e.g., a wildtype strain or a variant thereof) neutralizing antibody response in an animal (e.g., a mammal, such as a human) comprising administering to the animal an effective amount of a VLP or composition described herein.

In certain embodiments, the neutralizing antibody response blocks Spike protein-ACE2 binding. In certain embodiments, the neutralizing antibody response is an IgG SARS-CoV-2 neutralizing antibody response. In certain embodiments, the neutralizing antibody response is an IgA SARS-CoV-2 neutralizing antibody response. In certain embodiments, the neutralizing antibody response is an IgG and IgA SARS-CoV-2 neutralizing antibody response.

In certain embodiments, the method further comprises administering a second dose of an effective amount of a VLP or composition as described herein. In certain embodiments, the second dose is administered about 2 to 9 weeks after the first dose was administered. In certain embodiments, the second dose is administered about 3 to 6 weeks after the first dose was administered. In certain embodiments, the second dose is administered about 4 to 5 weeks after the first dose was administered.

In certain embodiments, the first and/or second dose is administered intramuscularly. In certain embodiments, the first and/or second dose is administered subcutaneously.

In certain embodiments, the method further comprises administering to the animal at least one additional agent. In certain embodiments, the at least one additional agent is an adjuvant (e.g., an adjuvant described herein or a combination thereof). In certain embodiments, the adjuvant is selected from the group consisting of monophosphoryl lipid A (MPL-A), aluminum salt (e.g., aluminum hydroxide, aluminum phosphate, or Alum), Complete Freund's Adjuvant (CFA), Incomplete Freund's Adjuvant (IFA), MF59, Montanide ISA 51, CpG, Glucopyranosyl Lipid Adjuvant (GLA), QS-21, and combinations thereof. In certain embodiments, a combination of monophosphoryl lipid A (MPL-A) and aluminum salt (e.g., aluminum hydroxide, aluminum phosphate or Alum) is administered to the animal.

In certain embodiments, the at least one additional agent is administered sequentially with the first dose and/or second dose. In certain embodiments, at least one additional agent is administered simultaneously with the first dose and/or second dose (e.g., separately or within the same composition as the first dose and/or second dose).

In certain embodiments, the animal is a human.

Certain embodiments of the invention also provide the use of a VLP or composition described herein for use in medical therapy.

Certain embodiments of the invention provide a VLP or composition described herein for use in 1) immunizing the animal for the prevention of an infection; 2) treating or preventing an infection in the animal; or 3) eliciting a neutralizing antibody response in the animal.

Certain embodiments of the invention also provide the use of a VLP or composition described herein to prepare a medicament for 1) immunizing the animal for the prevention of an infection; 2) treating or preventing an infection in the animal; or 3) eliciting a neutralizing antibody response in the animal.

In certain embodiments, the infection/response is a coronavirus infection/response. In certain embodiments, the infection/response is a SARS-CoV-1 infection/response, a SARS-CoV-1-like bat coronavirus infection/response (e.g., bat coronavirus SHC014 infection/response) or a SARS-CoV-2 infection/response (e.g., a wild-type SARS-CoV-2 strain or variant thereof, such as variant described herein).

Kits

Certain embodiments of the invention also provide a kit comprising:
a VLP or a composition as described herein;
packaging material; and
instructions for administering the VLP or the composition to an animal for 1) immunizing the animal for the prevention of an infection; 2) treating or preventing an infection in the animal; or 3) eliciting a neutralizing antibody response in the animal.

In certain embodiments, the infection/response is a coronavirus infection/response. In certain embodiments, the infection/response is a SARS-CoV-1 infection/response, a SARS-CoV-1-like bat coronavirus infection/response (e.g., bat coronavirus SHC014 infection/response) or a SARS-CoV-2 infection/response (e.g., a wild-type SARS-CoV-2 strain or variant thereof, such as variant described herein).

In certain embodiments, the kit further comprises at least one additional agent (e.g., a therapeutic agent, such as an adjuvant).

In certain embodiments, the kit comprises a syringe (e.g., pre-filled syringe) or vial comprising a VLP or a composition as described herein.

In certain embodiments, the kit comprises an atomizer nozzle that is or could be fitted with the syringe or vial to generate a spray or mist (e.g., for nasal or pulmonary delivery).

In certain embodiments, the kit comprises a needle that is or could be fitted with the syringe to deliver an injection (e.g., for subcutaneous, intradermal or intramuscular delivery).

Administration

In certain embodiments, an effective amount of a polypeptide, VLP or composition described herein is administered to the subject. "Effective amount" or "therapeutically effective amount" or "immunologically effective amount" are used interchangeably herein, and refer to an amount of a compound, formulation, material, or composition, as described herein effective to achieve a particular biological result. Such results may include, but are not limited to the inhibition of virus infection as determined by any means suitable in the art.

In certain embodiments, an amount of the vaccine is administered in order to immunize to the subject. As used herein, "immunization" or "vaccination" are used interchangeably herein and are intended for prophylactic or therapeutic immunization or vaccination.

In certain embodiments, a polypeptide, VLP or composition described herein is administered via intramuscular, intradermal, or subcutaneous delivery. In certain embodiments, a polypeptide, VLP or composition described herein is administered via a mucosal surface, such as an oral, or intranasal surface or via pulmonary delivery.

In certain embodiments, "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The polypeptides, VLPs and compositions of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present polypeptides or VLPs may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides or VLPs may be combined with one or more excipients and used in the form of ingestible tablets, buccal tablets, troches, capsules, elixirs, suspensions, syrups, wafers, and the like. Such compositions and preparations should contain at least 0.1% of polypeptides/VLPs. The percentage of the compositions and preparations may, of course, be varied and may conveniently be between about 2 to about 60% of the weight of a given unit dosage form. The amount of the polypeptides or VLPs in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides or VLPs, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides or VLPs may be incorporated into sustained-release preparations and devices.

The polypeptides or VLPs may also be administered intravenously or intraperitoneally by infusion or injection. Solutions of the polypeptides or VLPs can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the polypeptides or VLPs which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polypeptides or VLPs in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the polypeptides or VLPs plus any additional desired ingredient present in the previously sterile-filtered solutions.

For topical administration, the present polypeptides or VLPs may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present polypeptides or VLPs can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the polypeptides or VLPs to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

To immunize a subject, a polypeptide, VLP or composition described herein is administered parenterally, usually by intramuscular or subcutaneous injection in an appropriate vehicle. Other modes of administration, however, such as oral delivery or intranasal delivery, are also acceptable. Vaccine formulations will contain an effective amount of the active ingredient in a vehicle.

Formulations will contain an effective amount of the active ingredient in a vehicle, the effective amount being readily determined by one skilled in the art. The active ingredient may typically range from about 1% to about 95% (w/w) of the composition, or even higher or lower if appropriate. The amount for any particular application can vary depending on such factors as the severity of the condition. The quantity to be administered depends upon factors such as the age, weight and physical condition of the animal considered for vaccination and kind of concurrent treatment, if any. The quantity also depends upon the capacity of the animal's immune system to synthesize antibodies, and the degree of protection desired. Typically, dosages used in vitro may provide useful guidance in the amounts useful for in situ administration of the composition, and animal models may be used to determine effective dosages for treatment of particular disorders. Various considerations are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990, each of which is herein incorporated by reference. Additionally, effective dosages can be readily established by one of ordinary skill in the art through routine trials establishing dose response curves. The subject is immunized by administration of the composition thereof in one or more doses. Multiple doses may be administered as is required to maintain a state of immunity to the target. For example, the initial dose may be followed up with a booster dosage after a period of about four weeks to enhance the immunogenic response. Further booster dosages may also be administered. The composition may be administered multiple (e.g., 2, 3, 4 or 5) times at an interval of, e.g., about 1, 2, 3, 4, 5, 6 or 7, 14, or 21 days apart.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

Thus, the present compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the present compositions may be combined with one or more excipients and used in the form of ingestible tablets, buccal tablets, troches, capsules, elixirs, suspensions, syrups, wafers, and the like. Such preparations should contain at least 0.1% of the present composition. The percentage of the compositions may, of course, be varied and may conveniently be between about 2 to about 60% of the weight of a given unit dosage form. The amount of present composition in such therapeutically useful preparations is such that an effective dosage level will be obtained.

Useful dosages of the compositions of the present invention can be determined by comparing their in vitro activity, and in vivo activity in animal models. The amount of the compositions described herein required for use in treatment will vary with the route of administration and the age and condition of the subject and will be ultimately at the discretion of the attendant veterinarian or clinician.

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations; such as multiple inhalations from an insufflator or by application of a plurality of drops into the eye.

Polypeptides or VLPs of the invention can also be administered in combination with other therapeutic agents. Accordingly, one embodiment the invention also provides a composition comprising a polypeptide or VLP, at least one other therapeutic agent, and a pharmaceutically acceptable diluent or carrier.

Certain Embodiments

Embodiment 1. A virus-like nanoparticle (VLP) comprising:
1) a plurality of oligomerized VLP monomer polypeptides, wherein each VLP monomer polypeptide comprises an Fc binding domain amino acid sequence operably linked to a lumazine synthase (LS) amino acid sequence; and
2) a plurality of S-antigen-Fc polypeptides, wherein each S-antigen-Fc polypeptide comprises a SARS-CoV-2 Spike protein domain amino acid sequence operably linked to a Fc domain amino acid sequence.

Embodiment 2. The VLP of embodiment 1, wherein the VLP comprises 5 or more VLP monomer polypeptides, wherein the polypeptides are oligomerized.

Embodiment 3. The VLP of embodiment 1, wherein the VLP comprises 10 or more VLP monomer polypeptides, wherein the polypeptides are oligomerized.

Embodiment 4. The VLP of embodiment 1, wherein the VLP comprises 60 or more VLP monomer polypeptides, wherein the polypeptides are oligomerized.

Embodiment 5. The VLP of any one of embodiments 1-4, wherein the LS amino acid sequence is derived from the LS of *Aquifex aeolicus, Brucella* spp., *Brucella abortus*, or *Bacillus anthracis*.

Embodiment 6. The VLP of embodiment 5, wherein the LS amino acid sequence is derived from the LS of *Aquifex aeolicus*.

Embodiment 7. The VLP of embodiment 6, wherein the LS amino acid sequence comprises an amino acid sequence having at least about 90% sequence identity to SEQ ID NO:12.

Embodiment 8. The VLP of embodiment 6, wherein the LS amino acid sequence comprises an amino acid sequence having at least about 95% sequence identity to SEQ ID NO:12.

Embodiment 9. The VLP of embodiment 6, wherein the LS amino acid sequence comprises SEQ ID NO:12.

Embodiment 10. The VLP of embodiment 6, wherein the LS amino acid sequence consists of SEQ ID NO:12.

Embodiment 11. The VLP of any one of embodiments 1-10, wherein the Fc binding domain amino acid sequence comprises a Protein A domain sequence (e.g., the domain B of Protein A or a fragment thereof).

Embodiment 12. The VLP of embodiment 11, wherein the Protein A domain sequence is between about 50 to about 85 amino acids in length.

Embodiment 13. The VLP of embodiment 11, wherein the Protein A domain sequence is between about 55 to about 65 amino acids in length.

Embodiment 14. The VLP of embodiment 11, wherein the Protein A domain sequence is 59 amino acids in length.

Embodiment 15. The VLP of embodiment 11, wherein the Protein A domain sequence comprises an amino acid sequence having at least about 90% sequence identity to SEQ ID NO:11.

Embodiment 16. The VLP of embodiment 11, wherein the Protein A domain sequence comprises an amino acid sequence having at least about 95% sequence identity to SEQ ID NO:11.

Embodiment 17. The VLP of embodiment 11, wherein the Protein A domain sequence comprises SEQ ID NO:11.

Embodiment 18. The VLP of embodiment 11, wherein the Protein A domain sequence consists of SEQ ID NO:11.

Embodiment 19. The VLP of any one of embodiments 1-18, wherein the VLP monomer polypeptide further comprises one or more linker group(s).

Embodiment 20. The VLP of embodiment 19, wherein the Fc binding domain amino acid sequence is operably linked to the lumazine synthase (LS) amino acid sequence via a linker group.

Embodiment 21. The VLP of embodiment 20, wherein the linker group comprises an amino acid sequence having at least about 90% sequence identity to SEQ ID NO:10.

Embodiment 22. The VLP of any one of embodiments 1-21, wherein the VLP monomer polypeptide is operably linked to an affinity tag (e.g., poly(His) tag).

Embodiment 23. The VLP of embodiment 22, wherein the affinity tag is operably linked to the Fc binding domain amino acid sequence via a linker group.

Embodiment 24. The VLP of any one of embodiments 1-23, wherein the VLP monomer polypeptide further comprises a signal peptide sequence.

Embodiment 25. The VLP of any one of embodiments 1-24, wherein the VLP monomer polypeptide comprises an amino acid sequence having at least about 90% sequence identity to SEQ ID NO:15, 16, 17 or 22.

Embodiment 26. The VLP of any one of embodiments 1-25, wherein the SARS-CoV-2 Spike protein domain amino acid sequence comprises a SARS-CoV-2 receptor binding domain (RBD) amino acid sequence or SARS-CoV-2 S1 amino acid sequence.

Embodiment 27. The VLP of embodiment 26, wherein the SARS-CoV-2 Spike protein domain amino acid sequence comprises an amino acid sequence having at least about 90% sequence identity to SEQ ID NO:1, or SEQ ID NO:2.

Embodiment 28. The VLP of embodiment 26, wherein the SARS-CoV-2 Spike protein domain amino acid sequence comprises an amino acid sequence having at least about 95% sequence identity to SEQ ID NO:1 or SEQ ID NO:2.

Embodiment 29. The VLP of embodiment 26, wherein the SARS-CoV-2 Spike protein domain amino acid sequence comprises SEQ ID NO:1 or SEQ ID NO:2.

Embodiment 30. The VLP of embodiment 26, wherein the SARS-CoV-2 Spike protein domain amino acid sequence comprises SEQ ID NO: 1.

Embodiment 31. The VLP of embodiment 26, wherein the SARS-CoV-2 Spike protein domain amino acid sequence comprises SEQ ID NO:2.

Embodiment 32. The VLP of embodiment 26, wherein the SARS-CoV-2 Spike protein domain amino acid sequence consists of SEQ ID NO:1.

Embodiment 33. The VLP of embodiment 26, wherein the SARS-CoV-2 Spike protein domain amino acid sequence consists of SEQ ID NO:2.

Embodiment 34. The VLP of embodiment 26, wherein the SARS-CoV-2 Spike protein domain amino acid sequence comprises a SARS-CoV-2 receptor binding domain (RBD) amino acid sequence operably linked (e.g., directly or through a linker group) to the Fc domain amino acid sequence, wherein the SARS-CoV-2 RBD amino acid sequence is between about 197 to about 237 amino acids in length.

Embodiment 35. The VLP of embodiment 34, wherein the SARS-CoV-2 RBD comprises an amino acid sequence having at least about 90% sequence identity to SEQ ID NO:24.

Embodiment 36. The VLP of embodiment 34, wherein the SARS-CoV-2 RBD comprises an amino acid sequence having at least about 90% sequence identity to SEQ ID NO:1.

Embodiment 37. The VLP of embodiment 36, wherein the SARS-CoV-2 RBD comprises an amino acid sequence having at least about 95% sequence identity to SEQ ID NO:1.

Embodiment 38. The VLP of embodiment 36, wherein the SARS-CoV-2 RBD comprises an amino acid sequence having at least about 99% sequence identity to SEQ ID NO:1.

Embodiment 39. The VLP of embodiment 36, wherein the SARS-CoV-2 RBD comprises SEQ ID NO: 1.

Embodiment 40. The VLP of embodiment 35, wherein from 1 to 10 amino acids located at positions 1-10 in reference to the sequence corresponding to SEQ ID NO:24 are not comprised within the SARS-CoV-2 RBD amino acid sequence.

Embodiment 41. The VLP of embodiment 35, wherein from 1 to 10 amino acids located at positions 228-237 in reference to the sequence corresponding to SEQ ID NO:24 are not comprised within the SARS-CoV-2 RBD amino acid sequence.

Embodiment 42. The VLP of embodiment 35, wherein from 1 to 10 amino acids located at positions 1-10 in reference to the sequence corresponding to SEQ ID NO:24 are not comprised within the SARS-CoV-2 RBD amino acid sequence, and wherein from 1 to 10 amino acids located at positions 228-237 in reference to the sequence corresponding to SEQ ID NO:24 are not comprised within the SARS-CoV-2 RBD amino acid sequence.

Embodiment 43. The VLP of embodiment 36, wherein from 1 to 10 amino acids located at positions 1-10 in reference to the sequence corresponding to SEQ ID NO:1 are not comprised within the SARS-CoV-2 RBD amino acid sequence.

Embodiment 44. The VLP of embodiment 36, wherein from 1 to 10 amino acids located at positions 208-217 in reference to the sequence corresponding to SEQ ID NO:1 are not comprised within the SARS-CoV-2 RBD amino acid sequence.

Embodiment 45. The VLP of embodiment 36, wherein from 1 to 10 amino acids located at positions 1-10 in reference to the sequence corresponding to SEQ ID NO:1 are not comprised within the SARS-CoV-2 RBD amino acid sequence, and wherein from 1 to 10 amino acids located at positions 208-217 in reference to the sequence corresponding to SEQ ID NO:1 are not comprised within the SARS-CoV-2 RBD amino acid sequence.

Embodiment 46. The VLP of embodiment 34, wherein the SARS-CoV-2 RBD comprises an amino acid sequence having at least about 90% identity to a sequence corresponding to SEQ ID NO:25.

Embodiment 47. The VLP of embodiment 46, wherein the SARS-CoV-2 RBD further comprises from 1 to 10 amino acids provided in a sequence corresponding to SEQ ID NO:26.

Embodiment 48. The VLP of embodiment 46, wherein the SARS-CoV-2 RBD further comprises from 1 to 10 amino acids provided in a sequence corresponding to SEQ ID NO:27.

Embodiment 49. The VLP of embodiment 46, wherein the SARS-CoV-2 RBD further comprises 1 to 10 amino acids provided in a sequence corresponding to SEQ ID NO:26, and further comprises from 1 to 10 amino acids provided in a sequence corresponding to SEQ ID NO:27.

Embodiment 50. The VLP of embodiment 36, wherein the SARS-CoV-2 RBD further comprises from 1 to 10 amino acids provided in the sequence corresponding to SEQ ID NO:28.

Embodiment 51. The VLP of embodiment 36, wherein the SARS-CoV-2 RBD further comprises from 1 to 10 amino acids provided in the sequence corresponding to SEQ ID NO:29.

Embodiment 52. The VLP of embodiment 36, wherein the SARS-CoV-2 RBD further comprises 1 to 10 amino acids provided in the sequence corresponding to SEQ ID NO:28, and further comprises from 1 to 10 amino acids provided in the sequence corresponding to SEQ ID NO:29.

Embodiment 53. The polypeptide of any one of embodiments 34-52, wherein the SARS-CoV-2 RBD is between about 207 to about 227 amino acids in length.

Embodiment 54. The polypeptide of any one of embodiments 34-52, wherein the SARS-CoV-2 RBD is between about 213 to about 221 amino acids in length.

Embodiment 55. The polypeptide of any one of embodiments 34-52, wherein the SARS-CoV-2 RBD is between about 215 to about 219 amino acids in length.

Embodiment 56. The polypeptide of any one of embodiments 34-52, wherein the SARS-CoV-2 RBD is 217 amino acids in length.

Embodiment 57. The VLP of any one of embodiments 1-56, wherein the Fc domain amino acid sequence comprises a human Fc domain amino acid sequence.

Embodiment 58. The VLP of any one of embodiments 1-56, wherein the Fc domain amino acid sequence comprises a human IgG1, IgG2, IgG3 or IgG4 Fc domain amino acid sequence.

Embodiment 59. The VLP of any one of embodiments 1-56, wherein the Fc domain amino acid sequence comprises a human IgG4 Fc domain amino acid sequence.

Embodiment 60. The VLP of embodiment 59, wherein the Fc domain amino acid sequence comprises an amino acid sequence having at least about 90% sequence identity to SEQ ID NO:4 Embodiment 61. The VLP of embodiment 59, wherein the Fc domain amino acid sequence comprises an amino acid sequence having at least about 95% sequence identity to SEQ ID NO:4.

Embodiment 62. The VLP of embodiment 59, wherein the Fc domain amino acid sequence comprises SEQ ID NO:4.

Embodiment 63. The VLP of any one of embodiments 1-62, wherein the S-antigen-Fc polypeptide further comprises one or more linker group(s).

Embodiment 64. The VLP of embodiment 63, wherein the SARS-CoV-2 Spike protein domain amino acid sequence is operably linked to the Fc domain amino acid sequence via a linker group.

Embodiment 65. The VLP of any one of embodiments 1-64, wherein the S-antigen-Fc polypeptide further comprises a signal peptide sequence.

Embodiment 66. The VLP of any one of embodiments 1-65, wherein the S-antigen-Fc polypeptide comprises an amino acid sequence having at least about 90%, 95%, 99% or 100% sequence identity to SEQ ID NO:5, 6, 7, or 21.

Embodiment 67. The VLP of any one of embodiments 1-65, wherein the S-antigen-Fc polypeptide consists of SEQ ID NO:5, 6, 7, or 21.

Embodiment 68. The VLP of any one of embodiments 1-43, wherein two or more of the S-antigen-Fc polypeptides are dimerized.

Embodiment 69. The VLP of any one of embodiments 1-44, wherein at least about 80% of the S-antigen-Fc polypeptides are dimerized.

Embodiment 70. The VLP of any one of embodiments 1-44, wherein at least about 95% of the S-antigen-Fc polypeptides are dimerized.

Embodiment 71. The VLP of any one of embodiments 1-46, wherein the VLP comprises between about 100 to about 120 S-antigen-Fc polypeptides.

Embodiment 72. The VLP of any one of embodiments 1-46, wherein the VLP comprises about 120 S-antigen-Fc polypeptides.

Embodiment 73. A VLP monomer polypeptide as described in any one of embodiments 1-25.

Embodiment 74. An S-antigen-Fc polypeptide, or dimer thereof, as described in any one of embodiments 1 and 26-67.

Embodiment 75. A method of producing a VLP as described in any one of embodiments 1-48, comprising contacting a plurality of oligomerized VLP monomer polypeptides as described in any one of embodiments 1-25 with a plurality of the S-antigen-Fc polypeptides as described in any one of embodiments 1 and 26-72, under conditions suitable for Fc binding to occur.

Embodiment 76. The method of embodiment 75, wherein a molar excess of the S-antigen-Fc polypeptides is used.

Embodiment 77. The method of embodiment 75, the molar ratio of S-antigen-Fc polypeptide (e.g., dimerized) to VLP monomer polypeptide is from about 0.8:1 to 2:1.

Embodiment 78. The method of embodiment 76, wherein the molar ratio of S-antigen-Fc polypeptide (e.g., dimerized) to VLP monomer polypeptide is 1.6:1.

Embodiment 79. A VLP produced by a method as described in any one of embodiments 75-78.

Embodiment 80. A composition comprising:
a) a VLP monomer polypeptide as described in any one of embodiments 1-25,
b) a S-antigen-Fc polypeptide, or a dimer thereof, as described in any one of embodiments 1 and 26-67, and/or
c) a VLP as described in any one of embodiments 1-72 and 79,
and a carrier.

Embodiment 81. The composition of embodiment 80, a VLP monomer polypeptide as described in any one of embodiments 1-25, and a carrier.

Embodiment 82. The composition of embodiment 80, comprising a S-antigen-Fc polypeptide (e.g., or a dimer thereof), as described in any one of embodiments 1 and 26-67 and a carrier.

Embodiment 83. The composition of embodiment 80, comprising a VLP as described in any one of embodiments 1-72 and 79, and a carrier.

Embodiment 84. The composition of any one of embodiments 80-83, which is a pharmaceutical composition comprising a pharmaceutically acceptable carrier.

Embodiment 85. The composition of any one of embodiments 80-83, which is a vaccine composition.

Embodiment 86. The composition of any one of embodiments 80-85, which is a vaccine composition comprising one or more adjuvant(s) (e.g., monophosphoryl lipid A and/or aluminum salt (e.g., aluminum hydroxide, aluminum phosphate or Alum)).

Embodiment 87. A polynucleotide comprising a nucleotide sequence encoding a VLP monomer polypeptide as described in any one of embodiments 1-25, or a S-antigen-Fc polypeptide as described in any one of embodiments 1 and 26-67.

Embodiment 88. The polynucleotide of embodiment 87, which comprises a nucleic acid sequence having at least about 90% sequence identity to SEQ ID NO:18, SEQ ID NO:19, SEQ ID NO:20, or SEQ ID NO:23.

Embodiment 89. An expression cassette comprising a promoter operably linked to the polynucleotide of embodiment 87 or 88.

Embodiment 90. A vector comprising the polynucleotide of embodiment 87 or 88, or the expression cassette of embodiment 89.

Embodiment 91. A cell comprising the polynucleotide of embodiment 87 or 88, the expression cassette of embodiment 89 or the vector of embodiment 90.

Embodiment 92. The cell of embodiment 91, which is a mammalian cell.

Embodiment 93. The cell of embodiment 92, which is a human embryonic kidney (HEK) 293 cell (e.g., a 293F cell).

Embodiment 94. The cell of embodiment 91, which is a bacterial cell.

Embodiment 95. A method of making a cell as described in any one of claims 91-94, the method comprising transfecting or transducing the cell with the polynucleotide of claim 97 or 88, the expression cassette of claim 89 or the vector of claim 90.

Embodiment 96. A method of producing a polypeptide, the method comprising transfecting or transducing a cell with the polynucleotide of claim 87 or 88, the expression cassette of claim 89 or the vector of claim 90.

Embodiment 97. A method of producing a polypeptide, the method comprising culturing a cell as described in any one of claims 91-94 under conditions appropriate for polypeptide expression.

Embodiment 98. The method of embodiment 97, further comprising isolating the polypeptide from the cell, cellular components and/or growth media.

Embodiment 99. The method of embodiment 98, wherein the isolated protein comprises less than about 10% contaminants.

Embodiment 100. The method of any one of embodiments 96-99, which produces at least about 40 mg/liter cell culture of the polypeptide.

Embodiment 101. A polypeptide produced by a method as described in any one of claims 96-70.

Embodiment 102. A method of immunizing an animal for the prevention of a coronavirus infection (e.g., a SARS-CoV-2), comprising administering a first dose of an effective amount of a VLP as described in any one of embodiments 1-72 and 79, a S-antigen-Fc polypeptide as described in embodiment 74, or a composition as described in any one of embodiments 80-86 to the animal.

Embodiment 103. The method of embodiment 102, further comprising administering a second dose of an effective amount of the VLP as described in any one of embodiments 1-72 and 79, a S-antigen-Fc polypeptide as described in embodiment 74, or the composition as described in any one of embodiments 80-86 the animal.

Embodiment 104. The method of embodiment 103, wherein the second dose is administered about 2 to 9 weeks after the first dose was administered.

Embodiment 105. The method of embodiment 103, wherein the second dose is administered about 3 to 6 weeks after the first dose was administered.

Embodiment 106. The method of embodiment 103, wherein the second dose is administered about 4 to 5 weeks after the first dose was administered.

Embodiment 107. A method for treating or preventing a coronavirus (e.g., a SARS-CoV-2) infection in an animal, comprising administering an effective amount of a VLP as described in any one of embodiments 1-72 and 79, a S-antigen-Fc polypeptide as described in embodiment 74, or a composition as described in any one of embodiments 80-86 to the animal.

Embodiment 108. The method of any one of embodiments 102-107, wherein the coronavirus infection is a SARS-CoV-1 infection, a SARS-CoV-1-like bat coronavirus infection, or a SARS-CoV-2 infection.

Embodiment 109. The method of embodiment 108, wherein the coronavirus infection is SARS-CoV-2 infection.

Embodiment 110. The method of embodiment 109, wherein the SARS-CoV-2 infection is caused by a SARS-CoV-2 variant (e.g., K417T/N, E484K, N501Y, V367F, G476S, G485R, H519Q or D614G).

Embodiment 111. A method for eliciting a coronavirus (e.g., SARS-CoV-2) neutralizing antibody response in an animal, comprising administering an effective amount of a VLP as described in any one of embodiments 1-72 and 79, a S-antigen-Fc polypeptide as described in embodiment 74, or a composition as described in any one of embodiments 80-86 to the animal.

Embodiment 112. The method of embodiment 111, wherein the coronavirus neutralizing antibody response is a SARS-CoV-1 response, a SARS-CoV-1-like bat coronavirus response, or a SARS-CoV-2 response.

Embodiment 113. The method of embodiment 112, wherein the coronavirus neutralizing antibody response is SARS-CoV-2 response.

Embodiment 114. The method of embodiment 113, wherein the SARS-CoV-2 response is caused by a SARS-CoV-2 variant (e.g., K417T/N, E484K, N501Y, V367F, G476S, G485R, H519Q or D614G).

Embodiment 115. The method of any one of embodiments 102-114, further comprising administering to the animal at least one additional agent.

Embodiment 116. The method of embodiment 115, wherein the at least one additional agent is an adjuvant.

Embodiment 117. The method of embodiment 116, wherein the adjuvant is selected from the group consisting of monophosphoryl lipid A, aluminum salt (e.g., aluminum hydroxide, aluminum phosphate or Alum), Complete Freund's Adjuvant (CFA), Incomplete Freund's Adjuvant (IFA), MF59, Montanide ISA 51, CpG, Glucopyranosyl Lipid Adjuvant (GLA), QS-21, and combinations thereof.

Embodiment 118. The method of embodiment 117, wherein a combination of monophosphoryl lipid A and aluminum salt (e.g., Alum) is administered to the animal.

Embodiment 119. The method of any one of embodiments 115-118, wherein the at least one additional agent is administered sequentially with the first dose and/or second dose.

Embodiment 120. The method of any one of embodiments 115-118, wherein the at least one additional agent is administered simultaneously with the first dose and/or second dose.

Embodiment 121. The method of any one of embodiments 102-120, wherein the animal is a human.

Embodiment 122. A VLP as described in any one of embodiments 1-72 and 79, a S-antigen-Fc polypeptide as described in embodiment 74, or a composition as described in any one of embodiments 80-86 for use in medical therapy.

Embodiment 123. A VLP as described in any one of embodiments 1-72 and 79, a S-antigen-Fc polypeptide as described in embodiment 74, or a composition as described in any one of embodiments 80-86 for 1) immunizing an animal for the prevention of a coronavirus (e.g., SARS-CoV-2) infection; 2) the prophylactic or therapeutic treatment of a coronavirus infection; or 3) eliciting a coronavirus neutralizing antibody response in an animal.

Embodiment 124. The use of a VLP as described in any one of embodiments 1-72 and 79, a S-antigen-Fc polypeptide as described in embodiment 74, or a composition as described in any one of embodiments 80-86 to prepare a medicament for 1) immunizing an animal for the prevention of a coronavirus (e.g., SARS-CoV-2) infection; 2) the treatment or prevention of a coronavirus infection; or 3) eliciting a coronavirus neutralizing antibody response in an animal.

Embodiment 125. A kit comprising:
1) a VLP as described in any one of embodiments 1-72 and 79, a S-antigen-Fc polypeptide as described in embodiment 74, or a composition as described in any one of embodiments 80-86;
2) packaging material; and
3) instructions for administering the VLP, polypeptide or composition to an animal for 1) immunizing the animal for the prevention of a coronavirus (e.g., SARS-CoV-2) infection; 2) treating or preventing a coronavirus infection in the animal; or 3) eliciting a coronavirus neutralizing antibody response in the animal.

Embodiment 126. The kit of embodiment 125, further comprising at least one additional agent (e.g., a therapeutic agent).

Certain Definitions

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acids Res., 19:508; Ohtsuka et al. (1985) JBC, 260:2605; Rossolini et al. (1994) Mol. Cell. Probes, 8:91. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$) alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a conjugate of formula I through the carboxy terminus, the amino terminus, or through any other convenient point of attachment, such as, for example, through the sulfur of a cysteine.

The terms "protein," "peptide" and "polypeptide" are used interchangeably herein. Polypeptide sequences specifically recited herein are written with the amino terminus on the left and the carboxy terminus on the right.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

"Wild-type" refers to the normal gene, or organism found in nature without any known mutation.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, NY: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

A "vector" is defined to include, inter alia, any viral vector, plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al. (1995) Mol. Biotech. 3:225).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position+1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

As used herein, the term "operably linked" refers to a linkage of two elements in a functional relationship. For example, "operably linked" may refer to a linkage of polynucleotide elements or polypeptide elements in a functional relationship. A nucleic acid is "operably linked" when it is placed into a functional relationship with another nucleic acid sequence. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. "Operably-linked" also refers to the association two chemical moieties so that the function of one is affected by the other, e.g., an arrangement of elements wherein the components so described are configured so as to perform their usual function.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wisconsin, USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the Blast program (e.g., BlastN, version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87% 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) Proc. Natl. Acad. Sci. USA 82:488; Kunkel et al. (1987) Meth. Enzymol. 154:367; U.S. Pat. No. 4,873,192; Walker and Gaastra (1983) Techniques in Mol. Biol. (MacMillan Publishing Co., and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. In certain embodiments, the deletions, insertions, and substitutions of the polypeptide sequence encompassed herein may not produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," "transduced" and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a polypeptide of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, a "subject" is an animal, e.g., a mammal, e.g., a human, monkey, dog, cat, horse, cow, pig, goat, rabbit, or mouse.

The invention will now be illustrated by the following non-limiting Examples.

Example 1

The VLP used in this study (Nanominne) is based on a bacterial lumazine synthase protein, which can self-assemble into a 60-metric particle with icosahedral symmetry capable of binding a plurality of copies of antigen-Fc polypeptide (e.g., sixty copies of a dimerized antigen-Fc polypeptide), for example, SARS-CoV-2 RBD or S1 fused with human Fc proteins. In this application, SARS-CoV-2 RBD or S1 was displayed on the surface of a VLP scaffold to increase the antigen multi-valency needed for enhanced immunization. The binding of antigen-Fc polypeptide to the nanoparticles was confirmed by ELISA.

Design and Production of VLP Monomer Polypeptides

The VLP monomer polypeptide was designed with a lumazine synthase sequence derived from hyperthermophile *Aquifex aeolicus* bacterium (SEQ ID NO:12). To confer Fc binding ability, the domain B of protein A from *S. aureus* (SEQ ID NO: 11) was linked to the N-terminus of the LS amino acid sequence via a linking group (SEQ ID NO:10).

In addition, a Hiss tag (SEQ ID NO: 13) was linked to the N-terminus of the Protein A amino acid sequence via a linking group (SEQ ID NO:9) for affinity purification by nickel-chelating HP column (GE Healthcare). The mammalian tissue plasminogen activator signal peptide (tPA-SP) was further included at the N-terminus of the polypeptide to enable secretion of the VLP from mammalian cells for further affinity purification (see, SEQ ID NO:17). The DNA sequence (SEQ ID NO: 18) was inserted into the pCMV SPORT vector (Life Technologies) for mammalian expression.

The VLP monomer polypeptides were expressed from 293F cells using the FreeStyle 293 expression system (Invitrogen). The proteins with His-tag were harvested and purified sequentially on the HiTrap nickel-chelating HP column (GE Healthcare) and HiLoad™ 16/600 Superdex™ 200 pg gel filtration column (GE Healthcare), and stored in a buffer containing 20 mM Tris pH 7.2 and 150 mM NaCl.

The VLP monomer polypeptide (e.g., SEQ ID NO:22) was also successfully expressed in a soluble form in the prokaryotic system for further affinity purification. The VLPs were expressed from bacterial *E. coli* BL21 cells using Luria Broth medium (Tryptone: 10 g/l; Sodium Chloride: 10 g/l; Yeast Extract: 5 g/l) (Research Products International, RPI). The induction was performed by Isopropyl-β-D-thiogalactoside and Isopropyl-beta-D-thiogalactoside (Santa Cruz Biotechnology, Inc.) at a final concentration of 1 mM when the OD of *E. coli* BL21 reached 0.6-0.8. Then the inducted bacteria were further incubated at 37° C. for 4-5 hours (shake speed 250 rpm). The proteins with His-tag were harvested and purified sequentially on the HiTrap nickel-chelating HP column (GE Healthcare) and HiPrep™ 26/60 Sephacryl® 5-200 HR gel filtration column (GE Healthcare) and stored in a buffer containing 20 mM Tris pH 7.2 and 150 mM NaCl.

Design and Production of Antigen-Fc Polypeptide

The SARS2-RBD-hFc polypeptide was designed to include a SARS-Cov-2 RBD (SEQ ID NO:1) linked to the N-terminus of a human Fc domain (SEQ ID NO:4) via a linking group (SEQ ID NO:8). Additionally, a tPA signal was included at the N-terminus of the polypeptide. The DNA sequence (SEQ ID NO:19) was inserted into the pCMV SPORT vector (Life Technologies) for mammalian expression.

The SARS2-RBD-hFc protein (SEQ ID NO:6) was purified from the cell supernatants 3-4 days post-transfection by protein A affinity chromatography (GE Healthcare). The SARS2-RBD-hFc proteins were eluted using the acid solution (0.1 M citric acid at pH 2.7) and neutralized immediately using Tris-HCl at pH 9.6 (0.125 M final concentration). Then the proteins were further purified using HiLoad™ 16/600 Superdex™ 200 pg gel filtration column (GE Healthcare) and stored in a buffer containing 20 mM Tris pH 7.2 and 150 mM NaCl. The purified proteins were stored at −80° C. until further use.

The SARS2-S1-hFc polypeptide (e.g., SEQ ID NO:7) was produced using a similar method.

The purified VLP scaffolds (i.e., oligomerized VLP monomers) were combined with antigen-Fc proteins in a proper molar ratio to maximize the potency of antigen-Fc polypeptide.

ELISA

ELISA was carried out to detect SARS-CoV-2 S-RBD-specific antibodies in the immunized mouse sera. Specifically, ELISA plates were coated with SARS-CoV-2 RBD-Fc protein (10 μg/ml) overnight at 4° C. and blocked with 2% non-fat milk in PBS containing 0.5% Tween-20 (PBST) at 37° C. for 2 h. After three washes, the plates were incubated with serial dilutions of mouse sera and HRP-conjugated anti-mouse IgG (1:2,000) antibody at 37° C. for 1 h. The plates were then incubated with TMB (3,3',5,5'-tetramethylbenzidine) substrate, and $H_2SO_4$ (1N) to stop the reaction. Absorbance at 450 nm was measured by ELISA plate reader.

Pseudovirus Inhibition Assay

The immunized mouse sera were assayed for their ability to inhibit SARS-CoV-2 pseudovirus entry into hACE2-expressing cells using a pseudovirus neutralization assay. Specifically, 293T cells were co-transfected with a plasmid encoding SARS-CoV-2 spike protein and a plasmid encoding Env-defective, luciferase-expressing HIV-1 genome. Culture supernatants containing pseudoviruses were collected at 72 h after transfection, and incubated with serial dilutions of mouse sera at 37° C. for 1 h. The sera-virus mixtures were added to hACE2-expressing cells, and cultured at 37° C. Three days later, the cells were lysed, transferred into luminometer plates, and assayed for relative luciferase activity, based on which inhibitory ability of serum antibodies against SARS-CoV-2 pseudovirus entry was calculated.

Mouse Vaccination Study 1

Female C57BL/6 mice of 6-8 week age mice were used in the study. The animal protocols were approved by the Committee on the Ethics of Animal Experiments of the University of Minnesota. Specifically, C57BL/6 mice were subcutaneous (s.c.) immunized with the vaccine in the presence of the CFA (Complete Freund's Adjuvant) (initial immunization) or IFA (Incomplete Freund's Adjuvant) (subsequent immunization). The preparation of the vaccine included vortexing or mixing vigorously for several minutes just before use to form an emulsion.

The animals were divided into five groups, and each group had five animals.

For initial immunization:

Group 1: Phosphate-buffered saline (PBS) (50 μl)+CFA (50 μl);

Group 2: SARS-CoV-2 RBD-hFc (10 μg) in PBS (50 μl)+CFA (50 μl);

Group 3: SARS-CoV-2 RBD-hFc (10 μg)+VLP Nanoparticle (2.5 μg) in PBS (50 μl)+CFA (50 μl);

Group 4: SARS-CoV-2 RBD-hFc (50 μg)+VLP Nanoparticle (12.5 μg) in PBS (50 μl)+CFA (50 μl);

Group 5: VLP Nanoparticle (2.5 μg) in PBS (50 μl)+CFA (50 μl);

For subsequent immunization, the same regime was used. However, the IFA was used to replace with CFA. Immunized mice were boosted twice with the same immunogen and adjuvant at a 3-week interval, and sera samples were collected by eye-bleeding two weeks after each immunization for detection of neutralizing antibodies.

Mouse Vaccination Study 2

A vaccination protocol for a second study is shown in Table 1 below. The 1st dose was administered, and blood samples were obtained. The second dose is administered 4 weeks after 1st dose. Specifically, groups of 6 male and female BALB/c mice were immunized intramuscularly (I.M.) with each SARS-CoV-2 RBD-hFc or S1-hFc protein (10 µg/mouse) according to the protocol described in Table 1, in the presence of aluminum hydroxide (Alum, 500 µg/mouse) and MPL-A (10 µg/mouse) adjuvants. In the case where VLPs were used as the immunogen, the nanoparticles were incubated in advance with RBD-hFc or S1-hFc (e.g., dimerized RBD-hFc polypeptide, or dimerized S1-hFc polypeptide) at the molar ratio of 1.2:1 or 1.6:1 (RBD-hFc:Nanoparticle) for one hour at room temperature before being mixed with Alum+MPL-A adjuvants. The immunized mice were boosted once with the same immunogen and adjuvants at 28 days later. Sera were collected at 10 days post-each immunization for the detection of SARS-CoV-2 S-RBD-specific antibody responses and neutralizing antibodies.

120 copies of SARS-CoV-2 RBD on its surface is described. This VLP-RBD vaccine mimics virus-based vaccines in immunogen display, which boosts its efficacy, while maintaining the safety of protein-based subunit vaccines. Compared to the RBD vaccine, the VLP-RBD vaccine induced five times more neutralizing antibodies in mice that efficiently blocked SARS-CoV-2 from attaching to its ACE2 receptor and potently neutralized the cell entry of variant SARS-CoV-2 strains, SARS-CoV-1, and SARS-CoV-1-related bat coronavirus. These neutralizing immune responses induced by the VLP-RBD vaccine did not wane during the two-month study period.

Furthermore, the VLP-RBD vaccine effectively protected mice from SARS-CoV-2 challenge, dramatically reducing the development of clinical signs and pathological changes in immunized mice. The VLP-RBD vaccine provides one potentially effective solution to controlling the spread of SARS-CoV-2.

Introduction

Efficacious and safe vaccines are key to controlling the spread of viral infections. Thus far 50 viral vaccines have

TABLE 1

| Group BALB/c | 1st immunization + Dosage | 2nd immunization + Dosage (4-week interval) |
| --- | --- | --- |
| PBS | 280 µl PBS + 70 µl MPL-A + 350 µl Alum 100 µl/mouse (I.M.) | 280 µl PBS + 70 µl MPL-A + 350 µl Alum 100 µl/mouse (I.M.) |
| SARS-CoV-2 RBD-hFc | 6.3 µl SARS-CoV-2 RBD-hFc protein + 273.7 µl PBS + 70 µl MPL-A + 350 µl Alum 100 µl/mouse | 6.3 µl SARS-CoV-2 RBD-hFc protein + 273.7 µl PBS + 70 µl MPL-A + 350 µl Alum 100 µl/mouse |
| SARS-CoV-2 RBD-hFc (RBD):Nanoparticle = 1.2:1 (molar ratio) | 6.3 µl SARS-CoV-2 RBD-hFc + 7.91 µl Nanoparticle + 265.79 µl PBS + 70 µl MPL-A + 350 µl Alum 100 µl/mouse | 6.3 µl SARS-CoV-2 RBD-hFc + 7.91 µl Nanoparticle + 265.79 µl PBS + 70 µl MPL-A + 350 µl Alum 100 µl/mouse |
| SARS-CoV-2 RBD-hFc (RBD):Nanoparticle = 1.6:1 (molar ratio) | 6.3 µl SARS-CoV-2 RBD-hFc + 5.95 µl Nanoparticle + 267.75 µl PBS + 70 µl MPL-A + 350 µl Alum 100 µl/mouse | 6.3 µl SARS-CoV-2 RBD-hFc + 5.95 µl Nanoparticle + 267.75 µl PBS + 70 µl MPL-A + 350 µl Alum 100 µl/mouse |
| SARS-CoV-2 S1-hFc (S1):Nanoparticle = 1.2:1 (molar ratio) | 5.11 µl SARS-CoV-2 S1-hFc + 3.96 µl Nanoparticle + 270.93 µl PBS + 70 µl MPL-A + 350 µl Alum 100 µl/mouse | 5.11 µl SARS-CoV-2 S1-hFc + 3.96 µl Nanoparticle + 270.93 µl PBS + 70 µl MPL-A + 350 µl Alum 100 µl/mouse |

Results

Mice were immunized using the study protocols described above. Strong binding and neutralizing antibody responses in the serum of immunized mice were detected. Additionally, it was determined that the immunized sera blocks SARS-CoV-2 pseudovirus entry into human cells.

Example 2. Novel Virus-Like Nanoparticle Vaccine Effectively Protects Animal Model from SARS-CoV-2 Infection The key to ending the COVID-19 pandemic and its potential aftermath is to develop a variety of vaccines that are efficacious and safe, elicit lasting immunity, and cover a range of SARS-CoV-2 variants. Recombinant viral receptor-binding domains (RBDs) are safe vaccine candidates but often have limited efficacy due to the lack of a virus-like immunogen display pattern. Here the development of a novel virus-like nanoparticle (VLP) vaccine that displays been approved by the FDA for clinical use to combat viral infections (fda.gov/vaccines-blood-biologics/vaccines/vaccines-licensed-use-united-states). These vaccines can be classified into three types: (I) 84% are virus-based vaccines (including inactivated viruses and attenuated viruses), (II) 10% are protein-based vaccines (i.e., subunit vaccines), and (III) the remaining 6% are virus-like particle vaccines (VLP vaccines). Type I, virus-based vaccines, are efficacious but may trigger safety concerns (Plotkin S (2014) *Proc Natl Acad Sci USA* 111(34):12283-12287; Huang et al., (2004) *The Journal of infection* 49(3):179-209). Specifically, attenuated virus vaccines may infect people, cause side effects, and may also revert back to wild type viruses; inactivated virus vaccines may lose their antigenicity due to the inactivation procedure. Type II, protein-based vaccines, are usually safe because they cannot infect people. However, they are generally not sufficiently efficacious because the human immune system has evolved to recognize virus particles rather than individual viral proteins (Bachmann M F & Jennings G T (2010) *Nature reviews. Immunology*

10(11):787-796; Tai W, et al. (2019) *J Virol* 93(17)). Type III, VLP vaccines, also do not infect people. They are made of protein scaffolds that present multiple copies of viral immunogens on their surface. They are designed to maximize the human immune responses by mimicking two unique features of virus particles: high local density of antigens and repetitive pattern of antigen display (Liu et al., (2010) *Cold Spring Harbor perspectives in biology* 2(7): a002295; Baschong et al., (2003) *Journal of structural biology* 143(3):258-262). Thus, the VLP vaccines combine the advantages of virus-based and protein-based vaccines, while reducing their drawbacks (Azuma et al., (2018) *Chemical Society reviews* 47(10):3543-3557; Ladenstein R & Morgunova E (2020) *Biotechnology reports* (Amsterdam, Netherlands) 27:e00494).

A novel coronavirus, SARS-CoV-2, is responsible for the COVID-19 pandemic and has caused catastrophic damage to global health and economies (Li Q, et al. (2020) Early Transmission Dynamics in Wuhan, China, of Novel Coronavirus-Infected Pneumonia. *N Engl J Med*.; Huang C, et al. (2020) Clinical features of patients infected with 2019 novel coronavirus in Wuhan, China. *Lancet*). A spike protein on the viral surface guides the entry of SARS-CoV-2 into host cells (Li F (2016) *Annual review of virology* 3(1):237-261; Perlman S & Netland J (2009) *Nature Reviews Microbiology* 7(6):439-450). It contains a receptor-binding S1 subunit and a membrane-fusion S2 subunit. As the first step of viral entry, a defined receptor-binding domain (RBD) on SARS-CoV-2 S1 specifically binds to the cell-surface receptor angiotensin-converting enzyme 2 (ACE2) for viral attachment (Wan et al., (2020) *J Virol* 94(7); Li F (2015) *J Virol* 89(4):1954-1964; Zhou P, et al. (2020) A pneumonia outbreak associated with a new coronavirus of probable bat origin. *Nature*). Coronavirus RBDs are major immunogens on virus particles. Antibodies targeting the RBDs can potentially block the viral attachment step (Du L, et al. (2017) *Expert opinion on therapeutic targets* 21(2):131-143; Du L Y, et al. (2009) *Nature Reviews Microbiology* 7(3):226-236). It has been shown that SARS-CoV-2 RBD has significantly higher affinity for human ACE2 than the RBD of a closely related SARS-CoV-1 (Shang J, et al. (2020) *Nature* 581 (7807):221-224). Moreover, it was shown that SARS-CoV-2 RBD is often hidden in the spike protein as a possible viral strategy to evade the host immune response (Shang J, et al. (2020) *Proc Nat Acad Sci USA* 117(21):11727-11734). Over the past year, many variants of SARS-CoV-2 have emerged as the virus circulated in different regions of the world. These variants contain naturally selected mutations in the spike protein including the RBD (Dejnirattisai W, et al. (2021) *Cell*. doi: 10.1016/j.cell.2021.03.055. PubMed PMID: 33852911; Garcia-Beltran W F, et al. (2021) *Cell*. 2021; 184(9):2372-83) Thus, highly efficacious RBD-containing vaccines are needed to elicit robust immune responses to block the potent, evasive and divergent RBD from binding to its ACE2 receptor.

Extensive efforts have been devoted to developing vaccines against SARS-CoV-2. Several nucleic acids-based vaccines (including mRNA and DNA), viral vector vaccines, and inactivated virus vaccines have reached clinical trials, and two mRNA-based vaccines and one viral vector-based vaccine have been authorized for emergency use in humans (Dong Y, et al. (2020) *Signal transduction and targeted therapy* 5(1):237; Krammer F (2020) *Nature* 586(7830): 516-527). These vaccines have shown great promise in controlling the pandemic. However, there is a possibility that SARS-CoV-2 will become endemic; new coronaviruses may also emerge in the future. One such strategy is to develop a variety of coronavirus vaccines that complement the existing COVID-19 vaccines in combatting SARS-CoV-2 and other coronaviruses. SARS-CoV-2 RBD has been shown to be an efficacious vaccine candidate against SARS-CoV-2 in preclinical trials (Yang J, et al. (2020) *Nature* 586(7830):572-577). However, over a decade of research on coronavirus RBDs (Du L, et al. (2016) *Nature communications* 7:13473; Ma C, et al. (2014) *Vaccine* 32(46):6170-6176) indicates that the efficacy of the SARS-CoV-2 RBD vaccine will need to be further improved.

In this study, a VLP vaccine was designed and developed and its immunogenicity was tested in vitro and efficacy in vivo. The VLP used lumazine synthase as a structural scaffold (Azuma et al., (2018) *Chemical Society reviews* 47(10):3543-3557; Ladenstein R & Morgunova E (2020) *Biotechnology reports* (Amsterdam, Netherlands) 27:e00494). Specifically, lumazine synthase self assembles into a 60-mer conformation, allowing the presentation of 60 copies of viral immunogens to mimic the pattern of immunogen presentation on virus particles (Azuma et al., (2018) *Chemical Society reviews* 47(10):3543-3557; Ladenstein R & Morgunova E (2020) *Biotechnology reports* (Amsterdam, Netherlands) 27:e00494). The data described herein showed that compared to the RBD vaccine, the VLP-based RBD vaccine induced significantly higher immune responses against SARS-CoV-2, SARS-CoV-1, and their variants. Importantly, the VLP-based RBD vaccine provides highly effective protection against SARS-CoV-2 infection in a mouse model, indicating that this vaccine can be a new tool in the arsenal against the spread of SARS-CoV-2.

Results

Design and Characterization of VLP-RBD Vaccine Targeting SARS-CoV-2

Figures 3A, 3B, 3C:
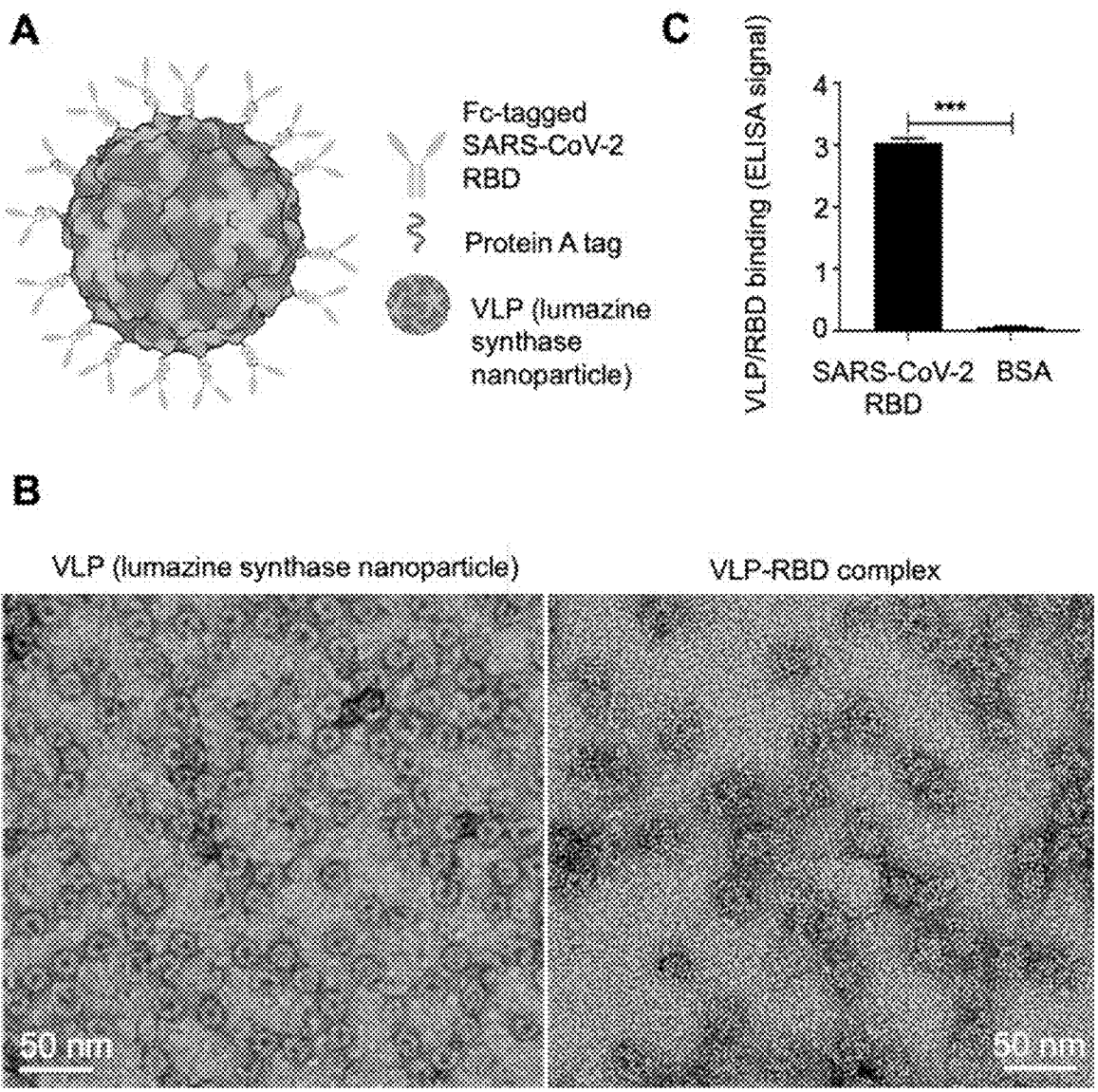
FIGS. 3A-3C. Design, construction and characterization of VLP-based SARS-CoV-2 RBD vaccine.

To develop a highly potent VLP-based RBD vaccine, the lumazine synthase (containing an N-terminal protein A tag) and SARS-CoV-2 RBD (containing a C-terminal Fc tag) was separately constructed (FIG. 3A). The lumazine synthase was expressed in both bacteria and mammalian cells and purified to high homogeneity (FIG. 8A). Independent of the expression source, the purified lumazine synthase spontaneously assembled to form a large VLP nanoparticle. The high molecular weight of the VLP nanoparticle was confirmed by its elution profile from gel filtration chromatography (FIG. 8A). Further, it was shown that under negative-stain electron microscopy (EM), the nanoparticle had the appearance of spheres with an average diameter of 15 nm (FIG. 3B). The Fc-tagged SARS-CoV-2 RBD was also expressed in mammalian cells and purified to high homogeneity (FIG. 8B). The purified SARS-CoV-2 RBD formed an oligomer, likely a dimer, as evidenced by its elution profile from its gel filtration chromatography (FIG. 8B). Thus, the lumazine synthase VLP nanoparticle and SARS-CoV-2 RBD were obtained, both of which were well formed as expected.

Next, the complex of the VLP nanoparticle and SARS-CoV-2 RBD was prepared and characterized. First, the binding interaction between the protein A-tagged VLP nanoparticle and Fc-tagged SARS-CoV-2 RBD was investigated using ELISA. The result confirmed binding of the two proteins to each other (FIG. 3C). Second, the protein A-tagged VLP nanoparticle and Fc-tagged SARS-CoV-2 RBD were mixed and the complex was purified via gel filtration chromatography. The result revealed that the two proteins formed a tight complex in solution and were co-eluted and co-purified from gel filtration chromatography (FIG. 8C). Third, it was shown that under negative-stain EM, the complex of VLP nanoparticle and SARS-CoV-2 RBD (i.e., VLP-RBD) retained the spherical shape of the nanoparticle, but attained a fuzzy surface (FIG. 3B). This design of the VLP-RBD vaccine allows 60 copies of Fc-tagged dimeric SARS-CoV-2 RBD, corresponding to 120 copies of SARS-CoV-2 RBD, to be displayed on the surface of the 60-meric protein A-tagged lumazine synthase VLP nanoparticle.

Figures 4A, 4B, 4C, 4D:
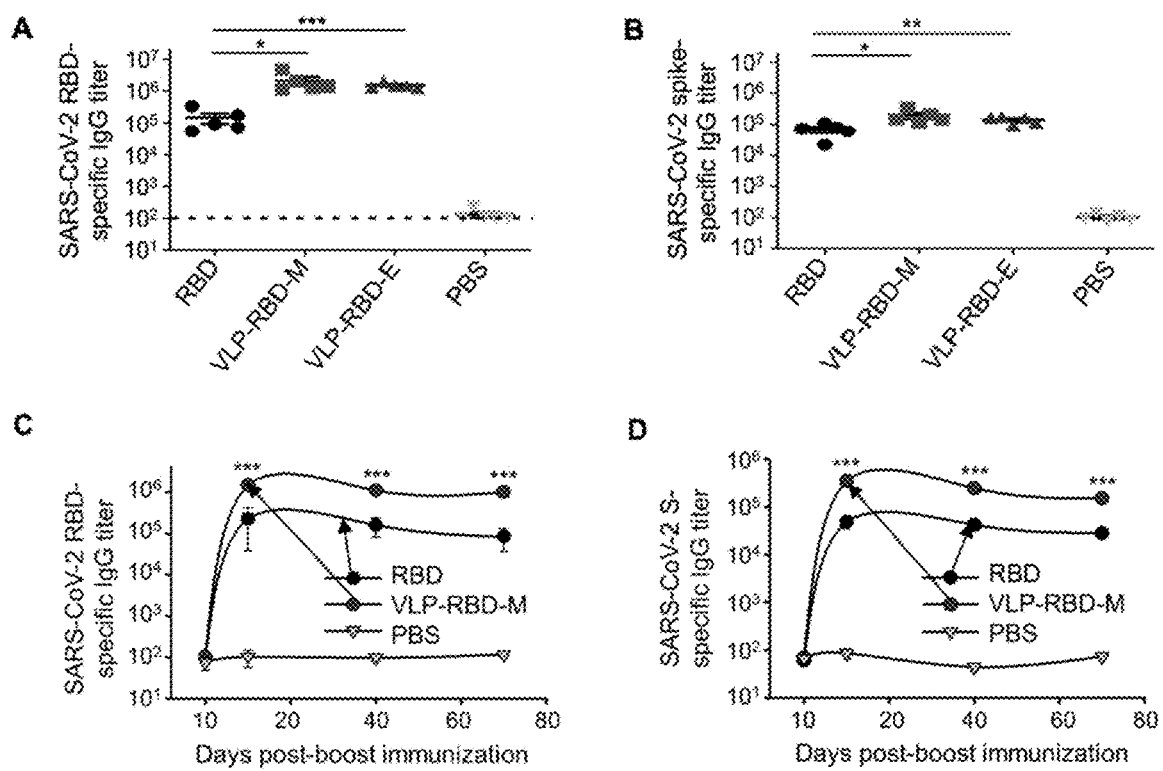
FIGS. 4A-4D. VLP-RBD vaccine induces high-titer antibody responses in mice. Mice were immunized with RBD, VLP-RBD-M (VLP was prepared from mammalian cells), VLP-RBD-E (VLP was prepared from bacteria cells), or PBS. Mouse sera were collected on day 10 post-$2^{nd}$ immunization for detection of RBD-specific antibodies (FIG. 4A) and spike-specific IgG antibodies (FIG. 4B) using ELISA. Mouse sera were also collected at later dates for detection of RBD-specific antibodies (FIG. 4C) and spike-specific IgG antibodies (FIG. 4D). For ELISA, plates were pre-coated with recombinant SARS-CoV-2 RBD or spike ectodomain, and antibody titers were reported as the highest serum dilution that remained detectable (defined as signal being at least twice of the blank). The dotted line indicates the detection limit (defined as the lowest serum dilution when signal was still below detectable levels). The data are presented as mean±SEM (n=5 for each mouse group). A Student's two-tailed t-test was performed to analyze the statistical differences among different groups. *p<0.001; p<0.01; *p<0.05. Experiments were repeated twice with similar results.
Figures 5A, 5B, 5C, 5D:
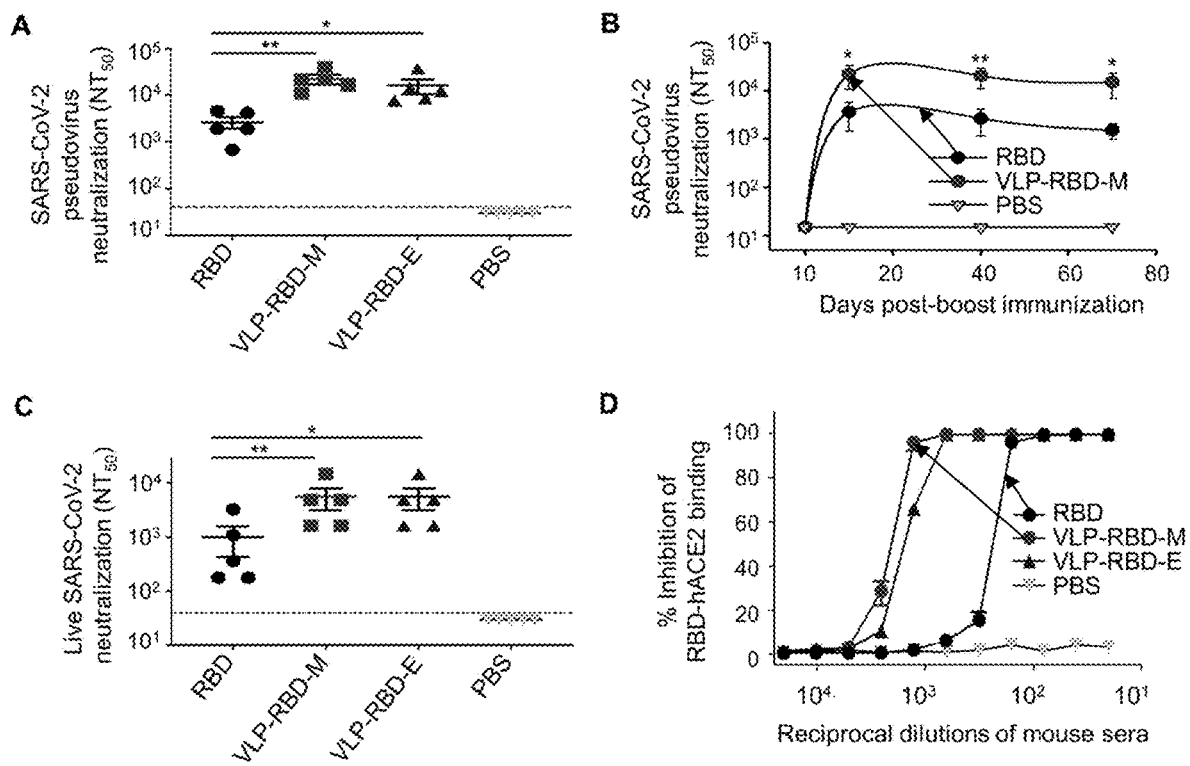
FIGS. 5A-5D. Antibody responses induced by VLP-RBD vaccine potently neutralize SARS-CoV-2 infection in vitro. Mouse sera from day 10 post-$2^{nd}$ immunization were examined for neutralizing antibodies against cell entry of pseudotyped SARS-CoV-2 (FIG. 5A) and cell infection of authentic SARS-CoV-2 (FIG. 5C). Mouse sera collected at later dates were also examined for neutralizing antibodies against cell entry of pseudotyped SARS-CoV-2 (FIG. 5B). For pseudovirus entry assay, retroviruses pseudotyped with SARS-CoV-2 were used to enter human cells in the presence of serially diluted mouse sera, and efficiency of pseudovirus entry was characterized as luciferase signal accompanying entry. For live virus assay, live SARS-CoV-2 was used to infect human cells in the presence of serially diluted mouse sera, and efficiency of live virus infection was characterized as cytopathic effect (CPE). Neutralizing activity of serum antibodies against pseudoviruses or live SARS-CoV-2 was expressed as $NT_{50}$ (neutralization titer that inhibits pseudovirus entry or live virus infection by 50%). The dotted lines indicate the detection limit for each experiment (defined as the lowest serum dilution).
Figures 12A, 12B:
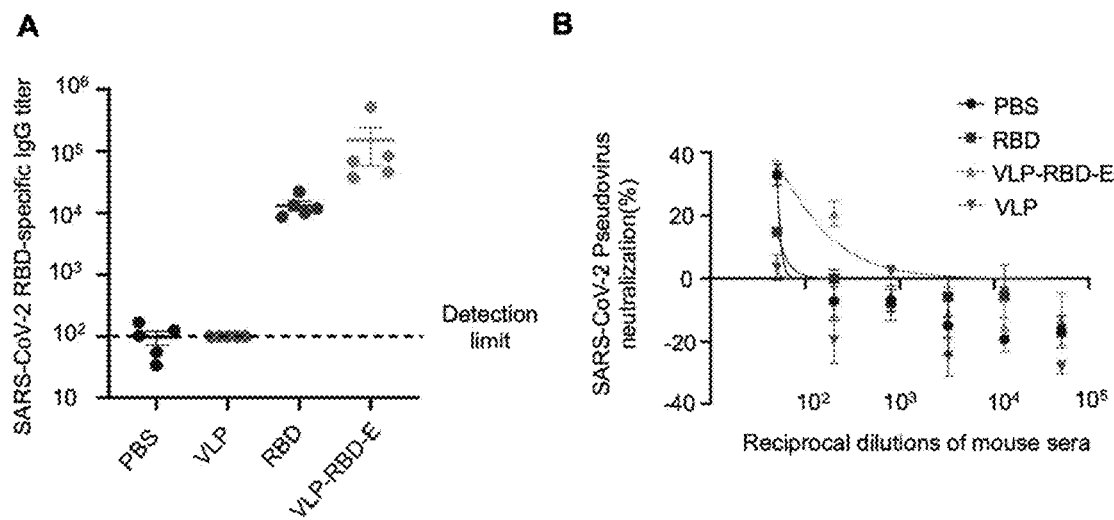
FIGS. 12A-12B. Antibody responses induced by VLP-RBD vaccine after the prime immunization. Mouse sera from day 10 post-$1^{st}$ immunization were examined for RBD-specific antibodies (FIG. 12A) and neutralizing antibodies against cell entry of pseudotyped SARS-CoV-2 (FIG. 12B). Mouse sera induced by VLP alone was analyzed and compared to those induced by the PBS buffer. The experiments in (FIG. 12A) and (FIG. 12B) were performed in the same way as in FIG. 4A and FIG. 9A, respectively, except that mouse sera from the prime immunization replaced those from the $2^{nd}$ immunization.

VLP-RBD Vaccine is Highly Potent in Inducing Neutralizing Antibody Responses in Mice The potency of the VLP-RBD vaccine in inducing neutralizing antibody responses against SARS-CoV-2 was evaluated. To this end, mice were immunized with one of two types of the VLP-RBD vaccines: VLP-RBD-E with the nanoparticle protein expressed from bacteria and VLP-RBD-M with the nanoparticle protein expressed from mammalian cells. The Fc-tagged RBD was used for comparison. The mice were further boosted with the same immunogen at 4 weeks after the prime immunization. Mouse sera were collected on days 10, 40, and 70 after the second immunization, and analyzed for their antibody titers and potency in neutralizing the cell entry of SARS-CoV-2. Compared to the RBD vaccine, the mouse sera induced by the VLP-RBD vaccine contained >5 times more RBD-specific and spike-specific IgG antibodies, respectively (FIG. 4A, 4B); they also neutralized the cell entry of SARS-CoV-2 pseudoviruses more potently (FIG. 5A). Moreover, compared to day 10, the mouse sera induced by the VLP-RBD vaccine and collected on days 40 and 70 contained similar amounts of RBD-specific and spike-specific IgG antibodies (FIG. 4C, 4D) and neutralized the cell entry of SARS-CoV-2 pseudoviruses with similar potency (FIG. 5B). Furthermore, compared with the RBD vaccine, the mouse sera induced by the VLP-RBD vaccine neutralized the cell infection of authentic SARS-CoV-2 more potently (FIG. 5C). Finally, VLP-RBD-E and VLP-RBD-M showed comparable potency in inducing neutralizing antibody titers (FIG. 4A, 4B and FIG. 5A, 5C) as well as in other parameters (see below), revealing that the nanoparticles prepared from mammalian cells and bacteria performed similarly well as the structural scaffold for the VLP-RBD vaccine. Finally, compared to the second immunization, the vaccine-induced mouse sera collected after the prime immunization contained significantly lower levels of RBD-specific IgG antibodies (FIG. 4A, FIG. 12A) and neutralized the cell entry of SARS-CoV-2 pseudoviruses less well (FIG. 12B); moreover, like the PBS buffer, VLP alone did not induce RBD-specific IgG antibodies (FIG. 12A). Together, these results demonstrate that compared to the RBD vaccine, the VLP-RBD vaccines induce higher-titer neutralizing antibody responses and inhibit SARS-CoV-2 infection more potently; additionally, these neutralizing antibody responses were boosted by the second immunization and last relatively long term.

Next, it was examined whether the antibody responses induced by the VLP-RBD vaccine neutralize different SARS-CoV-2 variants and other related coronaviruses. During the progression of COVID-19 pandemic, many SARS-CoV-2 variants have emerged. Among them, the recently emerged variants of P.1 lineage, B.1.351 lineage, and B.1.1.7 lineage are of great concern, owing to their ability to escape immune surveillance, spread more efficiently, and cause more severe disease (Dejnirattisai W, et al. (2021) *Cell*. doi: 10.1016/j.cell.2021.03.055. PubMed PMID: 33852911; Garcia-Beltran W F, et al. (2021) *Cell*. 2021; 184(9):2372-83). These variants contain mutations in the S1 subunit, particularly in the RBD. SARS-CoV-2 pseudoviruses corresponding to each of these three SARS-CoV-2 variants were generated. It was then shown that compared to the wild type SARS-CoV-2 pseudoviruses, the mouse sera induced by the VLP-RBD vaccine also neutralized the cell entry of the SARS-CoV-2 variant pseudoviruses with similar potency (FIG. 9A-9D).

Figures 9A, 9B, 9C, 9D:
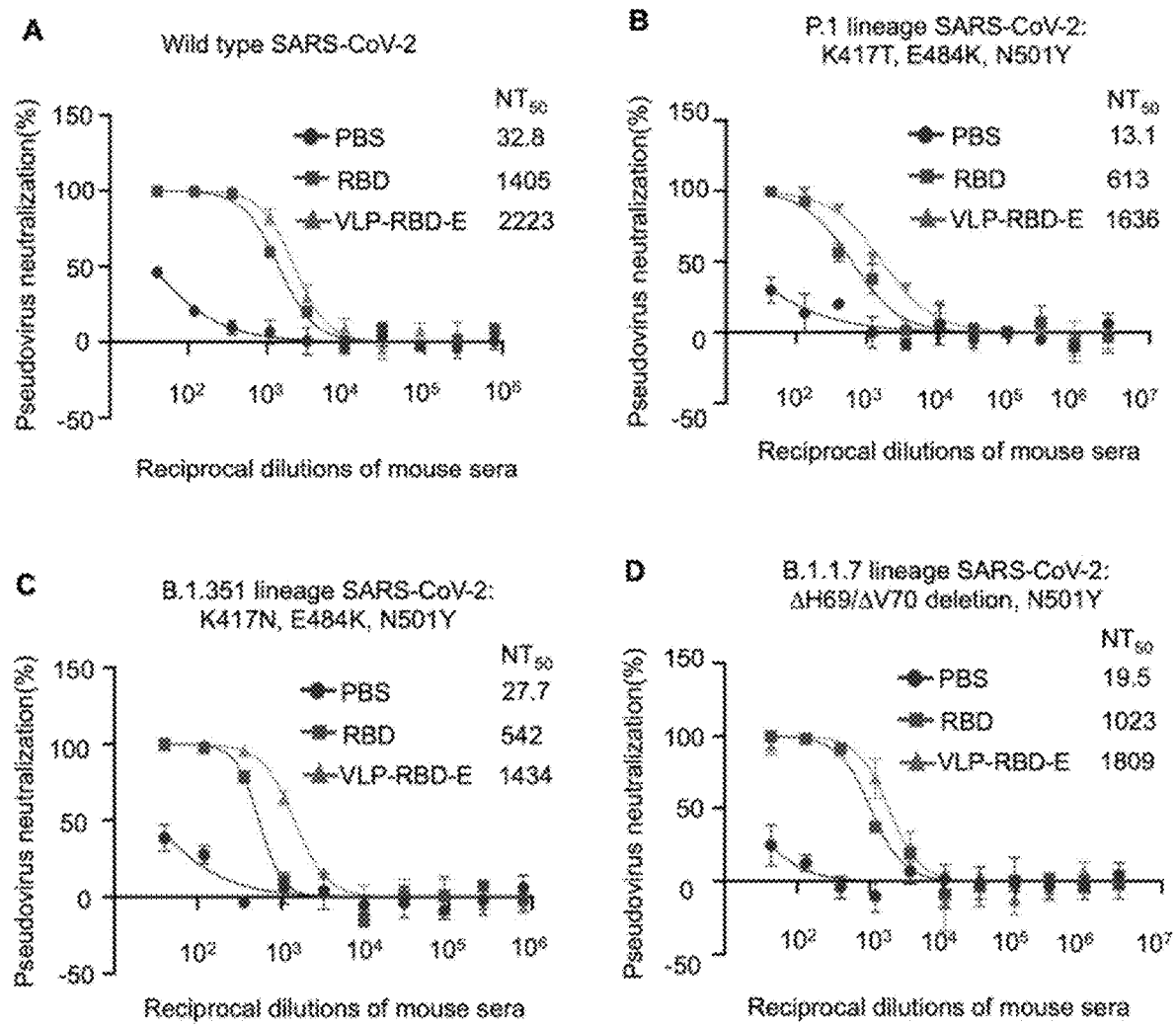
FIGS. 9A-9E. Antibody responses induced by VLP-RBD vaccine potently neutralize the cell entry of pseudotyped SARS-CoV-2 variants. Antibody responses induced by VLP-RBD vaccine potently neutralize the cell entry of pseudotyped SARS-CoV-2 wildtype (FIG. 9A) and variants (P.1 variant in FIG. 9B, B.1. 351 variant in FIG. 9C, or B.1.1.7 variant in FIG. 9D). The experiments were performed in the same way as in FIG. 6, except that a different pseudovirus system was used (see Materials and Methods) and also the mouse sera in each immunization group were pooled together. The mutation(s) in the S1 subunit of the SARS-CoV-2 variants (each defined as a lineage) are listed. Except for the ΔH69/ΔH70 deletions, all of the other mutations are located in the RBD.
Figure 9E:
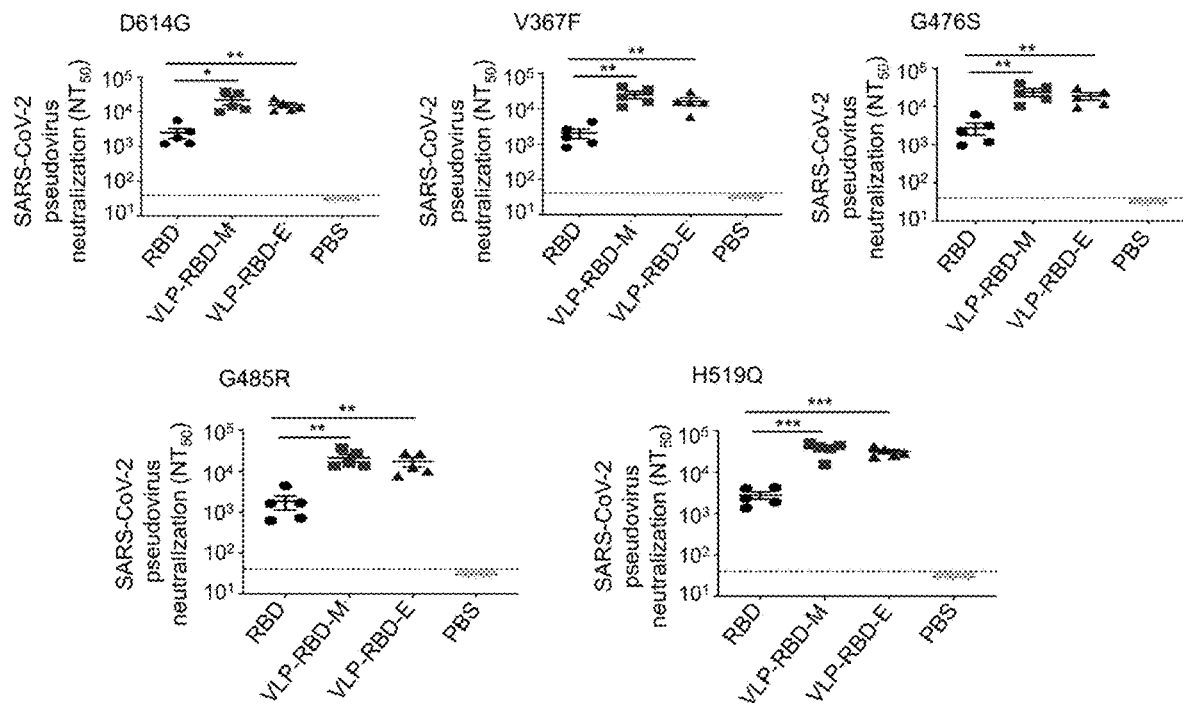

Similarly, numerous mutations have been identified in the SARS-CoV-2 spike protein including those in the RBD (e.g., V367F, G476S, G485R, and H519Q) and in the S2 (e.g., D614G) (Singh et al., (2020) *Journal of laboratory physicians* 12(2):154-160; Korber B, et al. (2020) *Cell* 182(4): 812-827.e819). SARS-CoV-2 pseudoviruses containing one of the above naturally occurring mutations in the spike protein (V367F, G476S, G485R, H519Q, or D614G) were also generated. It was then shown that compared to the wild type SARS-CoV-2 pseudoviruses, the mouse sera induced by the VLP-RBD vaccine also neutralized the cell entry of the SARS-CoV-2 variant pseudovirues with similar potency (FIG. 9E).

Figures 6A, 6B, 6C, 6D:
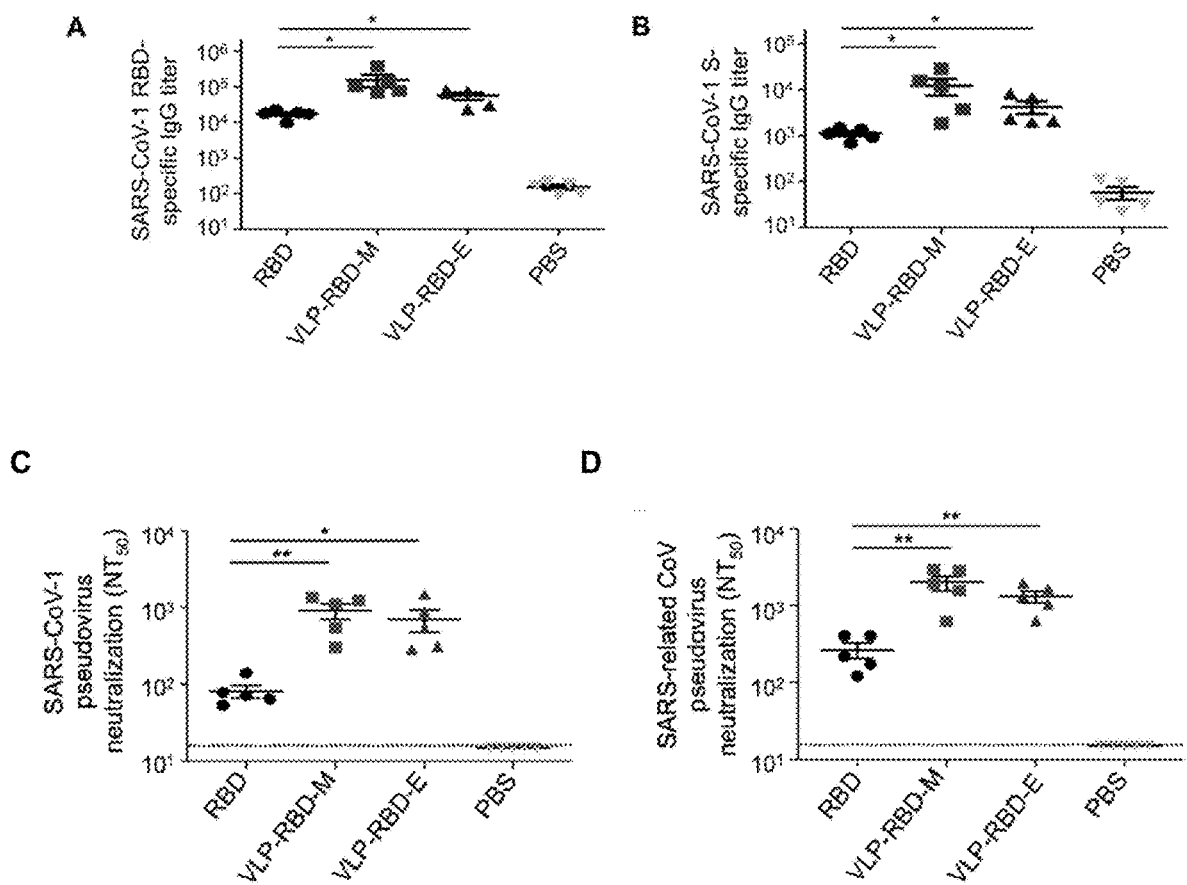
FIGS. 6A-6D. Antibody responses induced by VLP-RBD vaccine cross-neutralize the infections of SARS-CoV-1 and SARS-CoV-1-related bat coronavirus. The experiments were performed in the same way as in FIG. 4 and FIG. 5, except that SARS-CoV-1 and SARS-CoV-1-related bat coronavirus replaced SARS-CoV-2.

Additionally, compared to the SARS-CoV-2 variants, the SARS-CoV-2 spike protein shares lower but significant sequence similarities with the spike protein from SARS-CoV-1 and SARS-CoV-1-like bat coronaviruses (e.g., bat coronavirus SHC014) (Wan et al., (2020) *J Virol* 94(7); Ge X Y, et al. (2013) *Nature* 503(7477):535-538). Compared to the wild type SARS-CoV-2 pseudoviruses, the mouse sera induced by the VLP-RBD vaccine neutralized the cell entry of both SARS-CoV-1 and SHC014 pseudoviruses with lower but still significant potency (FIG. 6C, 6D). Overall, these data demonstrate that the VLP-RBD vaccine elicited antibody responses with potent cross-neutralizing capabilities against SARS-CoV-2 variants and significant cross-neutralizing capabilities against SARS-CoV-1 and its related bat coronavirus.

Figures 10A, 10B, 10C, 10D:
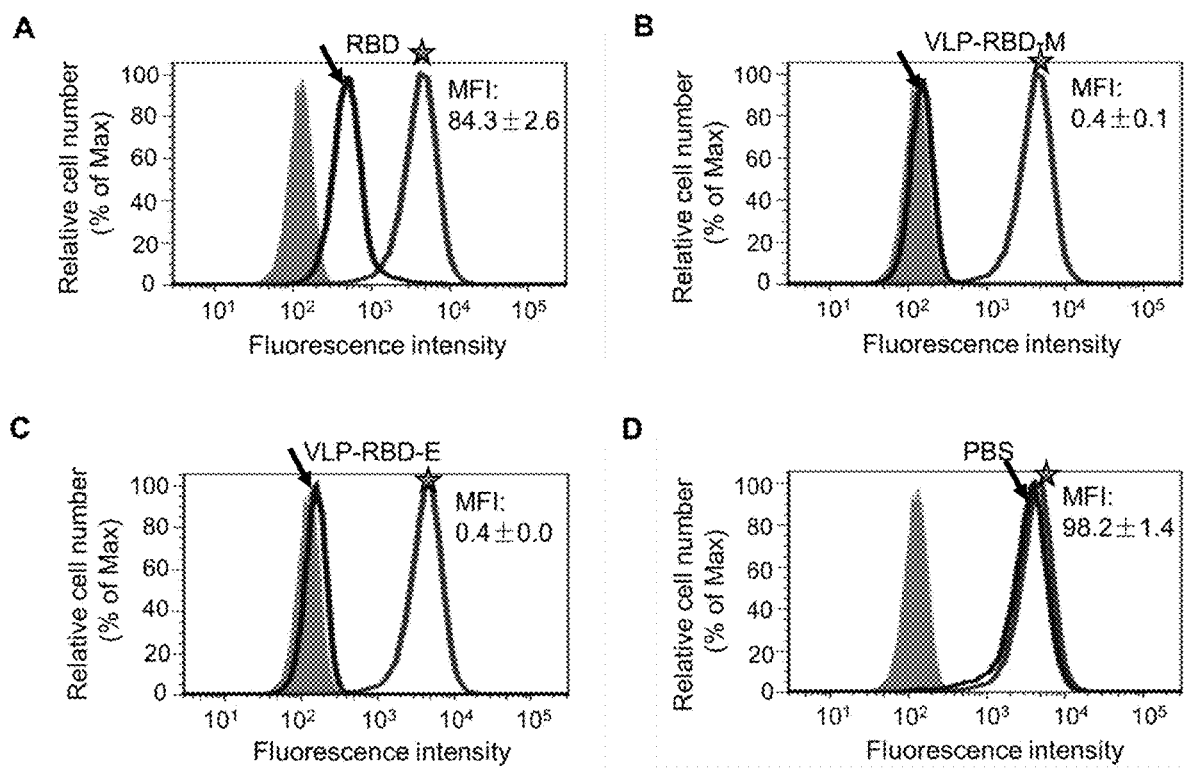
FIGS. 10A-10D. Representative images of flow cytometry showing that the mouse sera inhibit the interaction between SARS-CoV-2 RBD and human ACE2 receptor. The experiment was performed as described in FIG. 5D. Median fluorescence intensity (MFI) values (line marked with an arrow) indicate inhibitory activity of sera (1:320 dilution) from mice immunized with RBD vaccine (FIG. 10A), VLP-RBD-M (FIG. 10B), VLP-RBD-E (FIG. 10C), or PBS (FIG. 10D). The higher the MFI values, and the lower the inhibitory activity of the mouse sera. The interaction between SARS-CoV-2 RBD and ACE2 in the absence of mouse sera is shown with a line marked with a star. The interaction between Fc fragment and ACE2 in the presence of mouse sera is shown in gray shades. Experiments were repeated twice with similar results.

To investigate the mechanism by which the vaccine-induced antibodies neutralize SARS-CoV-2 infection, the interactions between SARS-CoV-2 RBD and human ACE2 were examined in the presence of the vaccine-induced mouse sera. To this end, a flow cytometry assay was performed where recombinant SARS-CoV-2 RBD was incubated with cell-surface-expressed human ACE2 in the presence of mouse sera. The result showed that mouse sera induced by either the RBD vaccine or VLP-RBD vaccine strongly blocked SARS-CoV-2 RBD binding to human ACE2, and that the latter sera were more potent than the former (FIG. 5D, FIG. 10). These data reveal that compared to the RBD vaccine, the VLP-RBD vaccine induces significantly higher-titer antibodies that block SARS-CoV-2 RBD binding to human ACE2 and neutralize SARS-CoV-2 infection of target cells.

VLP-RBD Vaccine Effectively Protected Mice from SARS-CoV-2 Challenge

The efficacy of the VLP-RBD vaccine in protecting animal models against SARS-CoV-2 infection was investigated. To this end, 3 weeks after the second immunization with either the RBD vaccine or VLP-RBD vaccine, the immunized mice were challenged with a mouse-adapted SARS-CoV-2 strain at high dosage ($10^5$ pfu) (Leist S R, et al. (2020) *Cell* 183(4):1070-1085.e1012). This mouse model of pathogenic SARS-CoV-2 infection replicates many of the features seen in severe COVID-19 cases in humans, including acute respiratory distress syndrome and acute lung injury. Here clinical disease was assessed by evaluating mice for clinical scores and weight changes, viral lung load was measured by plaque assay for infectious virus, and lung pathology was evaluated by scoring tissue for histopathological acute lung injury (ALI), gross lung discoloration (GLD) and diffuse alveolar damage (DAD) (Matute-Bello G, et al. (2011) *American journal of respiratory cell and molecular biology* 44(5):725-738; Schmidt M E, et al.

Figures 7A, 7B, 7C:
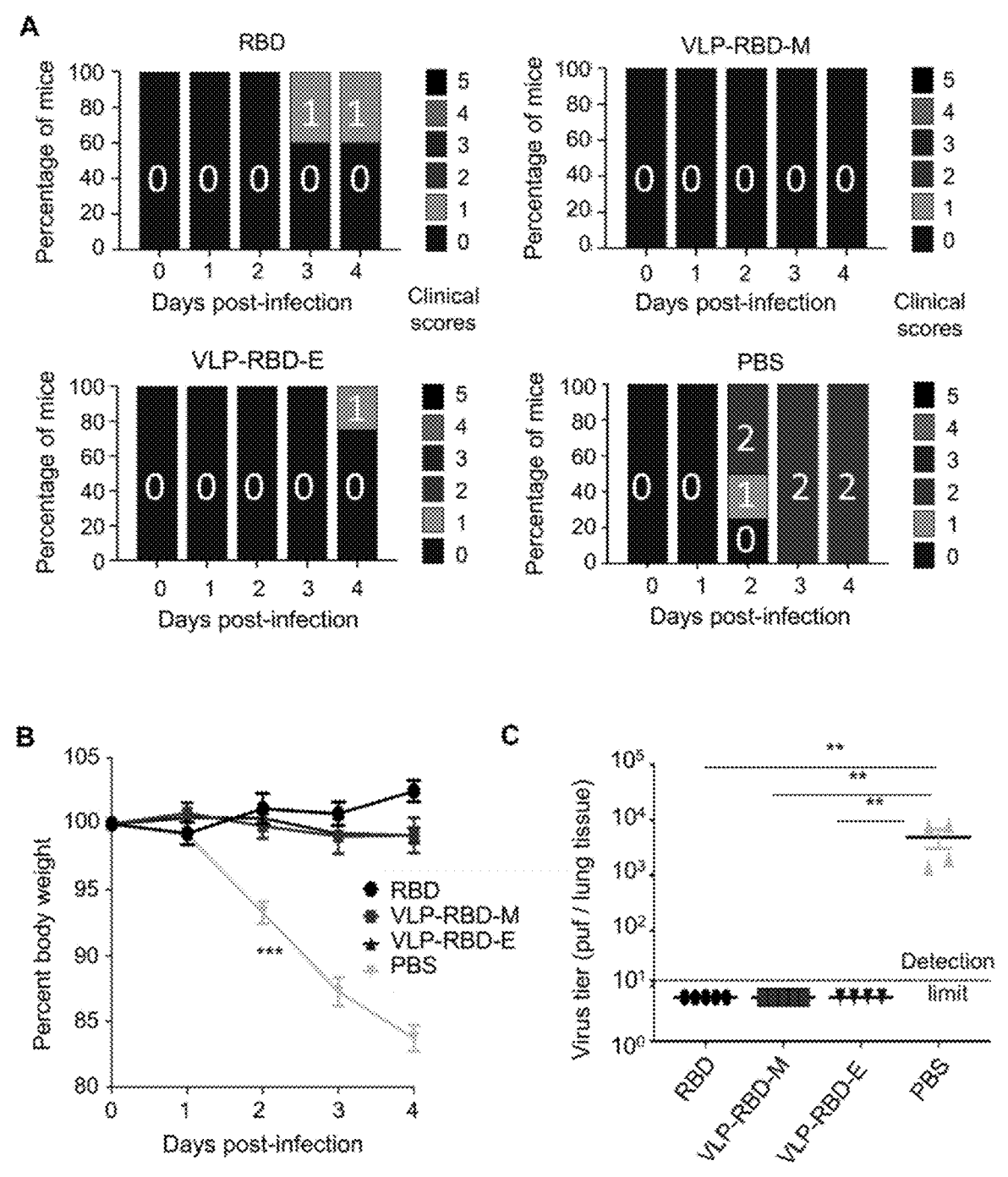
Figures 11A, 11B, 11C:
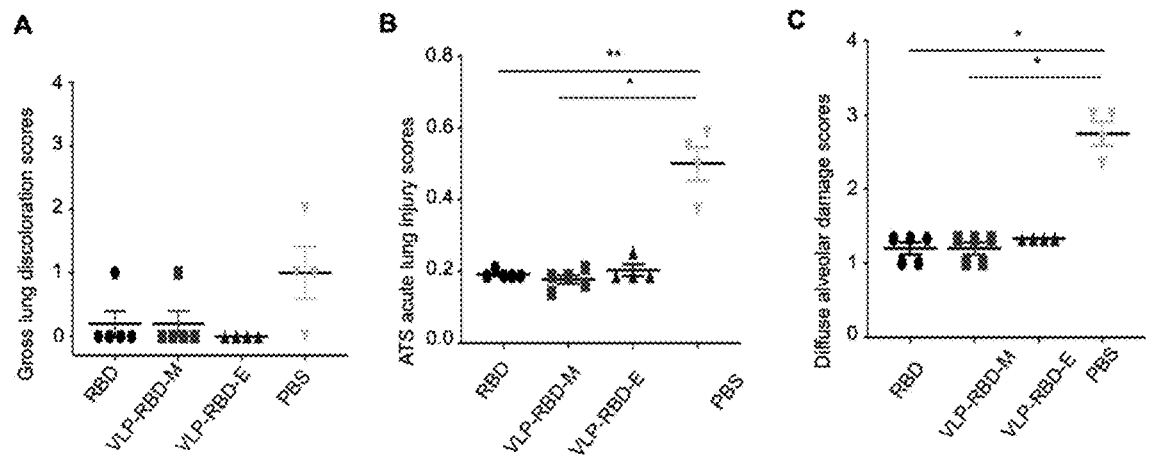
FIGS. 11A-11C. More data on the protective efficacy of VLP-RBD vaccine in mice against SARS-CoV-2 challenge. Gross lung discoloration scores (FIG. 11A), ATS acute lung injury scores (FIG. 11B), and diffuse alveolar damage scores (FIG. 11C) of mice on day 4 are shown. The data are presented as mean±SEM (n=4-5 for mice in each group). A Kruskal-Wallis test with Dunn's multiple comparisons was performed to analyze the statistical differences among different groups. **$p<0.01$; *$p<0.05$.

(2018) *PLoS Pathog* 14(1):e1006810; Sheahan T P, et al. (2020) *Nature communications* 11(1):222). Sham vaccinated mice immunized with PBS and adjuvants (referred to as PBS thereafter) were used as negative controls. On day 2, the sham vaccinated mice began to show progression in clinical scores and weight loss (FIG. 7A, 7B). By day 4, the sham vaccinated mice had lost an average of ~15% of their starting body weight and all of them had progressed to a clinical score of 2 (FIG. 7A, 7B). Moreover, the sham vaccinated mice contained high virus titers in the lung tissue (mean titer: $4.9 \times 10^3$ pfu per lung tissue) (FIG. 7C) and developed gross and histopathological signs of significant lung injury (average scores: 0.52 for ALI; 1 for GLD; 2.9 for DAD) (FIG. 11A-11C) on day 4. In contrast, mice immunized with either the RBD vaccine or the VLP-RBD vaccine showed no significant weight loss, contained no detectable infectious virus in the lung tissue, and developed minimal pathological changes of the lung (average scores: ~0.2 for ALI; 0.2 for GLD; ~1.1 for DAD) on day 4 (FIG. 7B, 7C; FIG. 11). However, among the five mice immunized with RBD vaccine, two mice developed clinical signs scored at 1 on days 3 and 4 and one developed a GLD score of 1 on day 4 (FIG. 7A, FIG. 11A). In comparison, among the four mice immunized with the VLP-RBD-E vaccine, none developed clinical signs or any GLD at day 4; among the five mice immunized with the VLP-RBD-M, none developed clinical signs, and one developed a GLD score of 1 at day 4 (FIG. 7A, FIG. 1 IA). Overall, these results demonstrate that the VLP-RBD vaccine offers nearly complete protection for mice against SARS-CoV-2 infection.

Discussion

Coronavirus vaccines hold the key to ending the COVID-19 pandemic and fighting potential future coronavirus infections. Currently SARS-CoV-2 vaccines, including mRNA vaccines, vector-based vaccines and inactivated virus particles, have been entering human clinical trials at an unprecedented speed. Among these vaccines, two mRNA-based vaccines and one viral vector-based vaccine have received FDA authorization for emergency use in humans. The demand for vaccines, however, far exceeds the supply. Together with an increase of SARS-CoV-2 variants, there is a pressing need for an increase in the variety of vaccines against SARS-CoV-2 and potential future coronavirus infections. Among the FDA-approved viral vaccines, 10% are protein-based subunit vaccines. Subunit vaccines do not contain any infectious viral components and hence are considered safer than virus-based vaccines. However, some subunit vaccines have relatively low immunogenicity. Coronavirus spike protein RBDs, which attach coronaviruses to host cells as the first step of infection, are one of the most immunogenic components among all coronavirus proteins, and hence are the prime targets for subunit vaccine design. A glycan shield approach was previously used to enhance the neutralizing immunogenicity of coronavirus RBDs as subunit vaccines (Du L, et al. (2016) *Nature communications* 7:13473). In this Example, a virus-like nanoparticle approach was used to enhance the neutralizing immunogenicity of SARS-CoV-2 RBD as subunit vaccine. Specifically, a nanoparticle scaffold protein was prepared that spontaneously assembled into a 60-mer VLP, displaying 60 copies of N-terminal protein A tag on the surface; Fc-tagged dimeric SARS-CoV-2 RBD was also prepared. When the protein A-tagged VLP nanoparticle and the Fc-tagged RBD were conjugated together, the assembled nanoparticle scaffold was capable of presenting 120 copies of RBD on the surface. The high local density and repetitive pattern of the presented RBD on the surface of the assembled VLP nanoparticle mimic those on the virus particles, likely accounting for the capacity of the VLP-RBD vaccine to induce potent and long-lasting immune responses (Liu et al., (2010) *Cold Spring Harbor perspectives in biology* 2(7):a002295; Baschong et al., (2003) *Journal of structural biology* 143 (3):258-262). Therefore, this design of VLP-based SARS-CoV-2 RBD vaccines holds promise for a novel SARS-CoV-2 vaccine with enhanced neutralizing immunogenicity.

The immunogenicity and protective efficacy of the VLP-RBD vaccine was also extensively examined using the RBD vaccine as a comparison. This study showed that both the VLP-RBD vaccine and the RBD vaccine trigger robust antibody responses in mice that potently block SARS-CoV-2 binding to its receptor, ACE2, and neutralize SARS-CoV-2 infection of human cells. In addition, the VLP-RBD vaccine is about five times more potent than the RBD vaccine in triggering neutralizing antibody responses in mice. The immune responses triggered by these vaccines last at least two months during the detection period. Moreover, both the VLP-RBD vaccine and the RBD vaccine effectively protected mice from challenge with a mouse-adapted SARS-CoV-2 strain, as evidenced by no significant weight loss, low or absent clinical scores, undetectable virus titer in the lungs and decreased lung pathology of vaccinated mice. However, while a subset of the mice immunized with the RBD vaccine still exhibited low disease scores, immunization with the VLP-RBD vaccine provided nearly complete protection from clinical disease, which is consistent with the observation that the VLP-RBD vaccine triggers much stronger neutralizing antibody responses than the RBD vaccine. It is also worth noting that the VLP-RBD vaccine works not only against wild type SARS-CoV-2, but also against SARS-CoV-2 variants, the related SARS-CoV-1 and a SARS-CoV-1-like bat coronavirus. This data suggest that these viruses share many neutralizing epitopes on their structurally related RBDs and that the VLP-RBD vaccine triggers potent immune responses to target these conserved neutralizing epitopes. Thus, the VLP-RBD vaccine described herein has the potential to be effective against a variety of SARS-CoV-2 strains, easing the concern about potential vaccine-escaping SARS-CoV-2 mutations. Overall, the design of VLP-based SARS-CoV-2 RBD vaccine described herein is highly potent in triggering robust and long-term immune responses against SARS-CoV-2 as well as its variants and in protecting animals from SARS-CoV-2 challenge.

In addition to their potency, cost-effectiveness is an important factor to consider for SARS-CoV-2 vaccines, given the world's vast population and the potential emergence of other coronaviruses. In this study, the VLP nanoparticle was prepared from both bacterial and mammalian cells, and it was shown that they performed similarly well as the structural scaffold for the VLP-RBD vaccine. This result is significant because it is more convenient and cost-effective to prepare proteins from bacteria than from mammalian cells. Although we prepared Fc-tagged SARS-CoV-2 RBD from mammalian cells to preserve the immunogenicity of the RBD, the yield of the RBD from mammalian cells was high due to the relatively small size and good folding of the RBD. Therefore, this design of the VLP-RBD vaccine enhances cost-effectiveness.

The VLP-RBD vaccine in this Example uses the lumazine synthase as the structural scaffold, which presents 120 copies of the RBD. Moreover, the study in this Example uniquely showed that the VLP-RBD vaccine design as described herein triggers longer-term neutralizing immune responses in mice and confers nearly complete protection against high-dose SARS-CoV-2 infection. The VLP-RBD vaccine in this Example also demonstrates a broad-spectrum activity against SARS-CoV-2 variants and other related coronaviruses with pandemic potential.

To summarize, a novel VLP-based RBD vaccine targeting SARS-CoV-2 was designed and produced. Its potency in inducing strong and long-lasting neutralizing immune responses against not only SARS-CoV-2 and its variants but also SARS-CoV-1 and its related bat coronavirus was demonstrated. It was also shown that the vaccine provides nearly complete protection against SARS-CoV-2 infection in available animal models. The preparation of this vaccine is easy, cost-effective and versatile. If further validated in human clinical trials, this vaccine can complement the existing vaccines in controlling the spread of SARS-CoV-2.

Materials and Methods

Cell Lines and Plasmids

HEK293T cells (human embryonic kidney cells) were obtained from the American Type Culture Collection (ATCC) and cultured in Dulbecco's modified Eagle medium (supplemented with 10% fetal bovine serum, 2 mM L-glutamine, 100 units/mL penicillin, and 100 µg/mL streptomycin). FreeStyle 293-F Cells were purchased from Gibco and cultured in FreeStyle 293 Expression Medium (Gibco) (supplemented with 100 units/mL penicillin and 100 µg/mL streptomycin). BL21 (DE3) E. coli cells were obtained from New England Biolabs and cultured in Luria Broth (Tryptone: 10 g/L, Yeast: 5 g/L, Sodium Chloride: 10 g/L) and 50 µg/mL Kanamycin.

Genes encoding SARS-CoV-2 spike (GenBank accession number QHD43416.1), SARS-CoV-1 spike (GenBank accession number AFR58740.1), SARS-CoV-1-related bat SHC014 spike protein (GenBank accession No. AGZ48806.1), human ACE2 (GenBank accession number: NM_021804), lumazine synthase of the hyperthermophile Aquifex aeolicus bacterium (GenBank accession number: WP_010880027.1), and domain B of protein A of S. aureus (UniProt accession number: P38507) were all synthesized (GenScript). SARS-CoV-2 RBD (residues 319-535) or SARS-CoV-1 RBD (residues 306-515) was subcloned into pLenti-transfer vector (Addgene) with an N-terminal tissue plasminogen activator (tPA) signal peptide and a C-terminal human IgG4 Fc region. Fc fragment was constructed in the same way as SARS-CoV-2 RBD, except the RBD gene was absent. Lumazine synthase was also subcloned into pET-42 b(+) vector (Addgene) with N-terminal Hiss-tag (SEQ ID NO: 13) and domain B of protein A (residues 212-270). ACE2 ectodomain (GenBank accession number: NM_021804) (residues 1-615) was also subcloned into pLenti-transfer vector with N-terminal TPA signal peptide and C-terminal Hiss-tag (SEQ ID NO: 13). The plasmids of $2^{nd}$ generation lentiviral packaging plasmid (psPAX2) (Addgene) and VSV-G envelope expressing plasmid (pMD2.G) (Addgene) were also used for packaging lentiviral particles used for stable cell construction. The pLKO.1 Protocol from Addgene was followed to generate the lentiviral particles. Puromycin (Gibco) was used for the selection of stable cell lines.

Protein Expression and Purification

Proteins were expressed from 293F cells as previously described (Ye G, et al. (2020) The Development of a Novel Nanobody Therapeutic for SARS-CoV-2. bioRxiv: 2020.2011.2017.386532). Briefly, the Fc-tagged proteins (SARS-CoV-2 RBD and Fc fragment alone) were collected from the cell culture medium, purified using Protein A column and gel filtration column (Cytiva). Mammalian cell-expressed and His-tagged lumazine synthase VLP nanoparticle protein (i.e., VLP-M) was prepared in the same way as the Fc-tagged SARS-CoV-2 RBD, except that Ni-NTA column replaced the protein A column in the procedure. E. coli-expressed and His-tagged lumazine synthase VLP nanoparticle protein (i.e., VLP-E) was expressed from bacterial BL21 (DE3) E. coli cells. The protein expression was induced using isopropyl-beta-D-thiogalactoside (Santa Cruz Biotechnology) at a final concentration of 1 mM when the bacterial growth reached the logarithmic phase. After induction, bacteria were allowed to grow for 4-5 h at 37° C. (shake speed 250 rpm). VLP-E was harvested from the cytoplasm of bacteria and purified in the same way as VLP-M. To prepare VLP-RBD, the purified VLP nanoparticle protein was incubated with Fc-tagged SARS-CoV-2 (the latter was in molar excess) at room temperature for 1 h and subsequently the formed complex was purified using gel filtration chromatography. Recombinant SARS-CoV-2 spike ectodomain was purchased from Sino Biological Inc.

Negative Staining Analysis

The negative-stain electron microscopy was performed as previously described (Wan Y, et al. (2020) Journal of Virology 94(5):e02015-02019). Briefly, the VLP-RBD-E sample was diluted to a final concentration of 0.3 mg/mL in Tris-HCl buffer (pH 10.0) and 200 mM NaCl, and was then loaded onto glow-discharged 400-mesh carbon grids (Electron Microscopy Sciences). The grids were stained with 0.75% uranyl formate. All micrographs were acquired using a FEI Tecnai $G^2$ F30 at 120 keV (FEI Company) and a 4 k×4 k Ultrascan CCD camera at 80,000× magnification at the University of Minnesota.

Immunization and Virus Challenge of Mice

Female BALB/cJ mice (6-8 weeks old) (THE JACKSON LABORATORY, stock 000651) were intramuscularly (I.M.) immunized with recombinant Fc-tagged SARS-CoV-2 RBD (10 µg/mouse), VLP-RBD-E (10 µg/mouse), VLP-RBD-M (10 µg/mouse), or PBS buffer in the presence of two adjuvants: aluminum hydroxide (Alum, 500 µg/mouse; InvivoGen) and monophosphoryl lipid A (MPL, 10 µg/mouse; InvivoGen). The mice were further boosted with same immunogen via I.M. at 4 weeks. Two separate experimental procedures were then performed. (i) Mouse sera were collected right before the $2^{nd}$ immunization and on days 10, 40, and 70 post-$2^{nd}$ immunization and were used for detection of antibody responses. (ii) 3 weeks post-$2^{nd}$ immunization, mice were challenged with mouse-adapted SARS-CoV-2 (see below).

ELISA

ELISA was carried out to detect the interaction between SARS-CoV-2 RBD and the nanoparticle as previously described (Ye G, et al. (2020) The Development of a Novel Nanobody Therapeutic for SARS-CoV-2. bioRxiv: 2020.2011.2017.386532). Briefly, ELISA plates were coated by 500 ng SARS-CoV-2 RBD (containing C-terminal Fc tag) or equal amount of BSA (which served as the negative control) at 4° C. overnight, and then washed with wash buffer (PBS+0.1% Tween-20). Subsequently, the ELISA plates were blocked with 5% milk at room temperature for 1 h. Then 250 ng VLP nanoparticle protein (containing N-terminal His tag and protein A tag) was added. After 2 h incubation at room temperature, the ELISA plates were washed and anti-His monoclonal antibody (1:1000) (Santa Cruz Biotechnology) was added. After another 1 h incubation at room temperature and more washes, secondary horseradish peroxidase (HRP)-conjugated anti-mouse antibodies (1:1000) (Santa Cruz Biotechnology) was added. After another 1 h incubation at room temperature, ELISA substrate (SIGMA-ALDRICH©) was added. The ELISA reaction was stopped using 1N $H_2SO_4$. The ELISA signal was read using the Epoch Microplate Spectrophotometer (BioTek Instruments) at the 450 nm wavelength.

ELISA was also performed to detect the interaction between SARS-CoV-2 RBD and RBD-specific antibodies in mouse sera as well as the interaction between SARS-CoV-2 spike ectodomain and spike-specific antibodies in mouse sera. The procedure was the same as described above, except that the ELISA plates were coated with 50 ng RBD or spike ectodomain and then sequentially incubated with serially diluted mouse sera (instead of VLP nanoparticle protein) and HRP-conjugated anti-mouse antibodies (1:5000) (Thermo Fisher Scientific).

Pseudovirus Neutralization Assay

The mouse sera collected above were examined for neutralizing antibodies against the cell entry of pseudotyped SARS-CoV-2, SARS-CoV-2 variants, SARS-CoV-1, and SARS-CoV-1-related bat coronavirus SHC014. Two types of pseudovirus systems were used. First, the pseudovirus particles for SARS-CoV-2, SARS-CoV-1, and SHC014 (FIG. 5A, 5B, FIG. 6D) were packaged as previously described (Ye G, et al. (2020) The Development of a Novel Nanobody Therapeutic for SARS-CoV-2. bioRxiv: 2020.2011.2017.386532). Briefly, HEK293T cells were co-transfected with a plasmid encoding one of the coronavirus spike proteins and a plasmid encoding Env-defective, luciferase-expressing HIV-1 genome (pNL4-3.luc.RE). Second, the pseudovirus particles for SARS-CoV-2 and its variants (FIG. 9A, 9B, 9C, 9D, FIG. 12B) were packaged as previously described (Peng G, et al. *J Biol Chem.* 2017 Feb. 10; 292(6): 2174-2181). Briefly, HEK293T cells were co-transfected with a plasmid encoding one of the coronavirus spike proteins, a helper plasmid psPAX2 and a reporter plasmid plenti-CMV-luc. For both pseudovirus systems, pseudoviruses were collected from culture supernatants at 72 h post-transfection and were incubated with serially diluted mouse sera at 37° C. for 1 h. The mixtures were then added to HEK293T cells stably expressing human ACE2 (Ye G, et al. (2020) The Development of a Novel Nanobody Therapeutic for SARS-CoV-2. bioRxiv: 2020.2011.2017.386532). After incubation at 37° C. for 72 h, the cells were lysed and transferred to luminometer plates. Then the luciferase substrate (Promega) was added and the relative luciferase activity was measured using Infinite 200 PRO Luminometer (Tecan). Neutralizing activity of serum antibodies against pseudoviruses was expressed as $NT_{50}$ (neutralization titer that inhibits pseudovirus entry by 50%).

Live Virus Neutralization Assay

The mouse sera collected above were examined for neutralizing antibodies against cell infection of live SARS-CoV-2 as previously described (Du L, et al. (2014) *J Virol* 88(12):7045-7053). Briefly, serially diluted mouse sera were mixed with SARS-CoV-2 (isolate US-WA-1; ~120 median tissue culture infectious dose or $TCID_{50}$), and incubated at room temperature for 1 h. The mixtures were subsequently added to Vero E6 cells pre-plated in 96-well tissue culture plates. The cells were then cultured at 37° C. for three days. Cells with or without virus were used as positive or negative control. Cytopathic effect (CPE) of cells was recorded on day 3 post-infection. Neutralizing antibody titer was expressed as the highest dilution of mouse sera being able to completely prevent virus-caused CPE in at least 50% of the wells.

Flow Cytometry

Flow cytometry was performed to detect the interaction between the SARS-CoV-2 RBD and ACE2 in the presence of mouse sera. Briefly, human ACE2-expressing HEK293T cells were incubated with recombinant Fc-tagged SARS-CoV-2 RBD (0.1 µg/ml) in the presence or absence of serially diluted mouse sera at room temperature for 1 h. After three washes with PBS (containing 2% FBS), the cells were incubated with FITC-labeled goat anti-human IgG-Fc antibody (1:500) (SIGMA-ALDRICH®) at room temperature for 20 min. After more washes, the cells were fixed with 4% formaldehyde, and the fluorescence intensity of the cells was measured using flow cytometry (BD LSRFortessa 4 system).

Mouse Infections and Tissue Collection

Mice were anesthetized with a cocktail of 50 mg/kg ketamine and 15 mg/kg xylazine and intranasally inoculated with $10^5$ pfu SARS-CoV-2 (mouse-passaged MA10; diluted in 50 µL PBS) (Leist S R, et al. (2020) *Cell* 183(4):1070-1085.e1012). Body weights of mice were measured daily, and clinical disease was assessed using a 6-point scoring system: 0=normal; 1=piloerection, 2=piloerection and kyphosis; 3=piloerection, kyphosis, and reduced movement; 4=piloerection, kyphosis, minimal spontaneous movement, +/−labored breathing (humane endpoint); 5=moribund, dead, or euthanized. Researchers were blinded to the vaccination status of the mice throughout the study. At 4 days post-infection, mice were euthanized by isoflurane overdose, and lungs were collected.

Lung Pathology

At the time of necropsy, lungs were evaluated for gross pathology using a 0-4-point gross lung discoloration scoring system (Sheahan T P, et al. (2020) *Nature communications* 11(1):222): 0=normal, pink lungs; 1=severe discoloration affecting less than 33% of the lung surface area or mild to moderate discoloration affecting less than 67% of the lung surface area; 2=severe discoloration affecting 34% to 67% of the lung surface area or mild to moderate discoloration affecting 68% to 99% of the lung surface area; 3=severe discoloration affecting 68% to 99% of the lung surface area or mild to moderate discoloration affecting 100% of the lung surface area; and 4=severe discoloration affecting 100% of the lung surface area. Dark pink or gray lung color was considered mild or moderate discoloration, and red, maroon, or brown lung color was considered severe discoloration. The left lung lobe was inflated with and immersed in 10% neutral buffered formalin for 7 days, embedded in paraffin (Leica Paraplast), sectioned at 4 µm thickness, and stained with hematoxylin and eosin (Richard Allan Scientific).

Lung sections were blindly evaluated for pathological changes using two scoring systems previously validated for SARS-CoV-2-MA10 infection (Matute-Bello G, et al. (2011) *American journal of respiratory cell and molecular biology* 44(5):725-738; Schmidt M E, et al. (2018) *PLoS Pathog* 14(1):e1006810) in three 600× fields per tissue by an ACVP-boarded veterinary pathologist (S.A.M). Acute lung injury (ALI) scores were analyzed using the following parameters: A) neutrophils in the alveolar space: 0=no cells, 1=1-5 cells, 2=>5 cells; B) neutrophils in the interstitium: 0=no cells, 1=1-5 cells, 2=>5 cells; C) hyaline membranes: 0=no membranes, 1=1 membrane, 2=>1 membrane; D) proteinaceous debris in the airspaces: 0=no debris, 1=1 instance, 2=>1 instance; E) alveolar septal thickening: 0=<2× thickness compared to mock-infected, 1=2-4× thickness compared to mock-infected, 2=>4× thickness compared to mock-infected. ALI scores were calculated using the following formula: $[(20 \times A)+(14 \times B)+(7 \times C)+(7 \times D)+(2 \times E)]/100$ and averaged among the three fields. Diffuse alveolar damage (DAD) scores were determined using the following: 1=no cellular sloughing or necrosis, 2=occasional solitary cell sloughing and necrosis, 3=>2 foci of cellular sloughing and necrosis with occasional septal wall hyalinization, and 4=cellular sloughing and necrosis in >75% of the field and/or prominent hyaline membranes. The scores of the three fields were averaged to determine the final DAD score.

Viral Lung Titers

Vero cells were plated at $2\times10^5$ cells per well in 12-well plates and allowed to grow to 90-95% confluency overnight. Superior and middle lung lobes were homogenized in 0.5 mL of media (DMEM+5% FBS+1 mM L-glutamine) at 6000 rpm for 40 sec using a Roche MagNA Lyser homogenizer and centrifuged for 1 min at full speed to pellet debris. 50 µL of the supernatant was added to 450 µL DMEM+5% FBS+1 mM L-glutamine media, and ten-fold serial dilutions were made to create a dilution series of $10^{-1}$ to $10^{-6}$. 200 µL of each homogenate dilution were added to the plated Vero cells and incubated at 37° C. After 1 hour, 2 mL of overlay (50:50 mixture of 2.5% carboxymethylcellulose and 2× alpha MEM+6% FBS+2% penicillin/streptomycin+2% L-glutamine+2% HEPES) was added to each well, and plates were incubated at 37° C., 5% $CO_2$ for 4 days. 2 mL of 4% paraformaldehyde was added to each well and allowed to fix cells overnight. Following removal of the fixative, wells were stained with 0.25% crystal violet, and visible plaques were counted and averaged between two technical replicate wells. Viral titers were calculated as pfu per lung tissue. The limit of detection (LOD) for the assay was determined to be 12.5 pfu/lung tissue, and samples that yielded no plaques were assigned a value of 6.25, half of the LOD.

Statistical Analyses

The values are presented as mean plus standard error of the mean (SEM). For FIGS. 3-6 and FIG. 9, a Student's two-tailed t-test was performed to analyze the statistical differences among different groups. For FIG. 7B, a two-way ANOVA with a Dunnett's multiple comparisons post-test was performed. For FIG. 7C and FIG. 11, a Kruskal-Wallis test with Dunn's multiple comparisons was performed. *P<0.05; P<0.01; *P<0.001. The statistics were analyzed using GraphPad Prism 5 statistical software.

TABLE 2

| SEQ ID NO: | Sequences | Comment |
|---|---|---|
| 1 | RVQPTESIVRFPNITNLCPFGEVFNATRFASVYAWNRKRISNCVADYS VLYNSASFSTFKCYGVSPTKLNDLCFTNVYADSFVIRGDEVRQIAPGQ TGKIADYNYKLPDDFTGCVIAWNSNNLDSKVGGNYNYLYRLFRKSNLK PFERDISTEIYQAGSTPCNGVEGFNCYFPLQSYGFQPTNGVGYQPYRV VVLSFELLHAPATVCGPKKSTNLVK | Protein sequence of SARS-CoV-2 RBD (aa 319 to 535 of Spike protein) |
| 2 | LTTRTQLPPAYTNSFTRGVYYPDKVFRSSVLHSTQDLFLPFFSNVTWF HAIHVSGTNGTKRFDNPVLPFNDGVYFASTEKSNIIRGWIFGTTLDSK TQSLLIVNNATNVVIKVCEFQFCNDPFLGVYYHKNNKSWMESEFRVYS SANNCTFEYVSQPFLMDLEGKQGNFKNLREFVFKNIDGYFKIYSKHTP INLVRDLPQGFSALEPLVDLPIGINITRFQTLLALHRSYLTPGDSSSG WTAGAAAYYVGYLQPRTFLLKYNENGTITDAVDCALDPLSETKCTLKS FTVEKGIYQTSNFRVQPTESIVRFPNITNLCPFGEVFNATRFASVYAW NRKRISNCVADYSVLYNSASFSTFKCYGVSPTKLNDLCFTNVYADSFV IRGDEVRQIAPGQTGKIADYNYKLPDDFTGCVIAWNSNNLDSKVGGNY NYLYRLFRKSNLKPFERDISTEIYQAGSTPCNGVEGFNCYFPLQSYGF QPTNGVGYQPYRVVVLSFELLHAPATVCGPKKSTNLVKNKCVNFNFNG LTGTGVLTESNKKFLPFQQFGRDIADTTDAVRDPQTLEILDITPCSFG GVSVITPGTNTSNQVAVLYQDVNCTEVPVAIHADQLTPTWRVYSTGSN VFQTRAGCLIGAEHVNNSYECDIPIGAGICASYQTQTNSP | SARS-CoV-2 Spike protein S1 amino acid sequence |
| 3 | MFVFLVLLPLVSSQCVNLTTRTQLPPAYTNSFTRGVYYPDKVFRSSVL HSTQDLFLPFFSNVTWFHAIHVSGTNGTKRFDNPVLPFNDGVYFASTE KSNIIRGWIFGTTLDSKTQSLLIVNNATNVVIKVCEFQFCNDPFLGVY YHKNNKSWMESEFRVYSSANNCTFEYVSQPFLMDLEGKQGNFKNLREF VFKNIDGYFKIYSKHTPINLVRDLPQGFSALEPLVDLPIGINITRFQT LLALHRSYLTPGDSSSGWTAGAAAYYVGYLQPRTFLLKYNENGTITDA VDCALDPLSETKCTLKSFTVEKGIYQTSNFRVQPTESIVRFPNITNLC PFGEVFNATRFASVYAWNRKRISNCVADYSVLYNSASFSTFKCYGVSP TKLNDLCFTNVYADSFVIRGDEVRQIAPGQTGKIADYNYKLPDDFTGC VIAWNSNNLDSKVGGNYNYLYRLFRKSNLKPFERDISTEIYQAGSTPC NGVEGFNCYFPLQSYGFQPTNGVGYQPYRVVVLSFELLHAPATVCGPK KSTNLVKNKCVNFNFNGLTGTGVLTESNKKFLPFQQFGRDIADTTDAV RDPQTLEILDITPCSFGGVSVITPGTNTSNQVAVLYQDVNCTEVPVAI HADQLTPTWRVYSTGSNVFQTRAGCLIGAEHVNNSYECDIPIGAGICA SYQTQTNSPRRARSVASQSIIAYTMSLGAENSVAYSNNSIAIPTNFTI SVTTEILPVSMTKTSVDCTMYICGDSTECSNLLLQYGSFCTQLNRALT GIAVEQDKNTQEVFAQVKQIYKTPPIKDFGGFNFSQILPDPSKPSKRS FIEDLLFNKVTLADAGFIKQYGDCLGDIAARDLICAQKFNGLTVLPPL LTDEMIAQYTSALLAGTITSGWTFGAGAALQIPFAMQMAYRFNGIGVT QNVLYENQKLIANQFNSAIGKIQDSLSSTASALGKLQDVVNQNAQALN TLVKQLSSNFGAISSVLNDILSRLDKVEAEVQIDRLITGRLQSLQTYV TQQLIRAAEIRASANLAATKMSECVLGQSKRVDFCGKGYHLMSFPQSA PHGVVFLHVTYVPAQEKNFTTAPAICHDGKAHFPREGVFVSNGTHWFV TQRNFYEPQIITTDNTFVSGNCDVVIGIVNNTVYDPLQPELDSFKEEL DKYFKNHTSPDVDLGDISGINASVVNIQKEIDRLNEVAKNLNESLIDL QELGKYEQYIKWPWYIWLGFIAGLIAIVMVTIMLCCMTSCCSCLKGCC SCGSCCKFDEDDSEPVLKGVKLHYT | SARS-CoV-2 Spike protein sequence |

TABLE 2-continued

| SEQ ID NO: | Sequences | Comment |
|---|---|---|
| 4 | PPCPSCPAPEFLGGPSVFLFPPKPKDTLMISRTPEVTCVVVDVSQEDP<br>EVQFNWYVDGVEVHNAKTKPREEQFNSTYRVVSVLTVLHQDWLNGKEY<br>KCKVSNKGLPSSIEKTISKAKGQPREPQVYTLPPSQEEMTKNQVSLTC<br>LVKGFYPSDIAVEWESNGQPENNYKTTPPVLDSDGSFFLYSRLTVDKS<br>RWQEGNVFSCSVMHEALHNHYTQKSLSLSLGK | Human IgG4 Fc |
| 5 | *MDAMKRGLCCVLLLCGAVFVSAS***RVQPTESIVRFPNITNLCPFGEVFN**<br>ATRFASVYANNRKRISNCVADYSVLYNSASFSTFKCYGVSPTKLNDLC<br>FTNVYADSFVIRGDEVRQIAPGQTGKIADYNYKLPDDFTGCVIANNSN<br>NLDSKVGGNYNYLYRLFRKSNLKPFERDISTEIYQAGSTPCNGVEGFN<br>CYFPLQSYGFQPTNGVGYQPYRVVVLSFELLHAPATVCGPKKSTNLVK<br>LEACGTPPCPSCPAPEFLGGPSVFLFPPKPKDTLMISRTPEVTCVVVD<br>VSQEDPEVQFNWYVDGVEVHNAKTKPREEQFNSTYRVVSVLTVLHQDW<br>LNGKEYKCKVSNKGLPSSIEKTISKAKGQPREPQVYTLPPSQEEMTKN<br>QVSLTCLVKGFYPSDIAVEWESNGQPENNYKTTPPVLDSDGSFFLYSR<br>LTVDKSRWQEGNVFSCSVMHEALHNHYTQKSLSLSLGK | An exemplary S-antigen-Fc polypeptide sequence having: tPA signal peptide (in itaiics) + SARS-CoV-2 RBD (in bold) + linker(underlined) human IgG4 Fc |
| 6 | RVQPTESIVRFPNITNLCPFGEVFNATRFASVYAWNRKRISNCVADYS<br>VLYNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSNLK<br>PFERDISTEIYQAGSTPCNGVEGFNCYFPLQSYGFQPTNGVGYQPYRV<br>VVLSFELLHAPATVCGPKKSTNLVKLEACGTPPCPSCPAPEFLGGPSV<br>FLFPPKPKDTLMISRTPEVTCVVVDVSQEDPEVQFNWYVDGVEVHNAK<br>TKPREEQFNSTYRVVSVLTVLHQDWLNGKEYKCKVSNKGLPSSIEKTI<br>SKAKGQPREPQVYTLPPSQEEMTKNQVSLTCLVKGFYPSDIAVEWESN<br>GQPENNYKTTPPVLDSDGSFFLYSRLTVDKSRWQEGNVFSCSVMHEAL<br>HNHYTQKSLSLSLGK | An exemplary S-antigen-Fc polypeptide sequence having: SARS-CoV-2 RBD in bold) + linker (under-lined) + human IgG4 Fc |
| 21 | *MDAMKRGLCCVLLLCGAVFVSAS***LTTRTQLPPAYTNSFTRGVYYPDKV**<br>FRSSVLHSTQDLFLPFFSNVTWFHAIHVSGTNGTKRFENPVLPFNEGV<br>YFASTEKSNIIRGWIFGTTLDSKTQSLLIVNNATNVVIKVCEFQFCND<br>PFLGVYYHKNNKSWMESEFRVYSSANNCTFEYVSQPFLMDLEGKQGNF<br>KNLREFVFKNIDGYFKIYSKHTPINLVRDLPQGFSALEPLVDLPIGIN<br>ITRFQTLLALHRSYLTPGDSSSGWTAGAAAYYVGYLQPRTFLLKYNEN<br>GTITDAVDCALDPLSETKCTLKSFTVEKGIYQTSNFRVQPTESIVRFP<br>NITNLCPFGEVFNATRFASVYAWNRKRISNCVADYSVLYNSASFSTFK<br>CYGVSPTKLNDLCFTNVYADSFVIRGDEVRQIAPGQTGKIADYNYKLP<br>DDFTGCVIAWNSNNLDSKVGGNYNYLYRLFRKSNLKPFERDISTEIYQ<br>AGSTPCNGVEGFNCYFPLQSYGFQPTNGVGYQPYRVVVLSFELLHAPA<br>TVCGPKKSTNLVKNKCVNFNFNGLTGTGVLTESNKKFLPFQQFGRDIA<br>DTTDAVRDPQTLEILDITPCSFGGVSVITPGTNTSNQVAVLYQDVNCT<br>EVPVAIHADQLTPTWRVYSTGSNVFQTRAGCLIGAEHVNNSYECDIPI<br>GAGICASYQTQTNSPLEACGTPPCPSCPAPEFLGGPSVFLFPPKPKDT<br>LMISRTPEVTCVVVDVSQEDPEVQFNWYVDGVEVHNAKTKPREEQFNS<br>TYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTT<br>PPVLDSDGSFFLYSRLTVDKSRWQEGNVFSCSVMHEALHNHYTQKSLS<br>LSLGK | An exemplary S-antigen-Fc polypeptide sequence having: tPA signal peptide (in italics) + SARS-CoV-2 S1 (in bold) + linker (under-lined) + human IgG4 Fc |
| 7 | LTTRTQLPPAYTNSFTRGVYYPDKVFRSSVLHSTQDLFLPFFSNVTWF<br>HAIHVSGTNGTKRFENPVLPFNEGVYFASTEKSNIIRGWIFGTTLESK<br>TQSLLIVNNATNVVIKVCEFQFCNDPFLGVYYHKNNKSWMESEFRVYS<br>SANNCTFEYVSQPFLMDLEGKQGNFKNLREFVFKNIDGYFKIYSKHTP<br>INLVRDLPQGFSALEPLVDLPIGINITRFQTLLALHRSYLTPGDSSSG<br>WTAGAAAYYVGYLQPRTFLLKYNENGTITDAVDCALDPLSETKCTLKS<br>FTVEKGIYQTSNFRVQPTESIVRFPNITNLCPFGEVFNATRFASVYAW<br>NRKRISNCVADYSVLYNSASFSTFKCYGVSPTKLNDLCFTNVYADSFV<br>IRGDEVRQIAPGQTGKIADYNYKLPDDFTGCVIAWNSNNLDSKVGGNY<br>NYLYRLFRKSNLKPFERDISTEIYQAGSTPCNGVEGFNCYFPLQSYGF<br>QPTNGVGYQPYRVVVLSFELLHAPATVCGPKKSTNLVKNKCVNFNFNG<br>LTGTGVLTESNKKFLPFQQFGRDIADTTDAVRDPQTLEILDITPCSFG<br>GVSVITPGTNTSNQVAVLYQDVNCTEVPVAIHADQLTPTWRVYSTGSN<br>VFQTRAGCLIGAEHVNNSYECDIPIGAGICASYQTQTNSPLEACGTPP<br>CPSCPAPEFLGGPSVFLFPPKPKDTLMISRTPEVTCVVVDVSQEDPEV<br>QFNWYVDGVEVHNAKTKPREEQFNSTYRVVSVLTVLHQDWLNGKEYKC<br>KVSNKGLPSSIEKTISKAKGQPREPQVYTLPPSQEEMTKNQVSLTCLV<br>KGFYPSDIAVEWESNGQPENNYKTTPPVLDSDGSFFLYSRLTVDKSRW<br>QEGNVFSCSVMHEALHNHYTQKSLSLSLGK | An exemplary S-antigen-Fc polypeptide sequence having: SARS-CoV-2 S1 (in bold) + linker (underlined) + human IgG4 Fc |
| 8 | LEACGT | Linker sequence |
| 9 | SALA | Linker sequence |
| 10 | LINGGSGGSGGSGGSGGG | Linker sequence |

TABLE 2-continued

| SEQ ID NO: | Sequences | Comment |
|---|---|---|
| 11 | ADNKFNKEQQNAFYEILHLPNLNEEQRNGFIQSLKDDPSQSANLLAEA KKLNDAQAPKA | a Protein A domain amino acid sequence (domain B of Protein A) |
| 12 | MQIYEGKLTAEGLRFGIVASRFNHALVDRLVEGAIDAIVRHGGREEDI TLVRVPGSWEIPVAAGELARKEDIDAVIAIGVLIRGATPHFDYIASEV SKGLAQLSLELRKPITFGVITADTLEQAIERAGTKHGNKGWEAALSAI EMANLFKSLR | a Lumazine Synthase (LS) domain amino acid sequence |
| 30 | MQIYEGKLTAEGLRFGIVASRFNHALVDRLVEGAIDCIVRHGGREEDI TLVRVPGSWEIPVAAGELARKEDIDAVIAIGVLIRGATPHFDYIASEV SKGLANLSLELRKPITFGVITADTLEQAIERAGTKHGNKGWEAALSAI EMANLFKSLR | A Lumazine Synthase (LS) domain amino acid sequence: WP_010880027.1 6,7-dimethyl-8-ribityllumazine synthase [Aquifex aeolicus] |
| 13 | HHHHHHHH | His8 tag |
| 14 | MDAMKRGLCCVLLLCGAVFVSAS | tPA signal peptide |
| 15 | ADNKENKEQQNAFYEILHLPNLNEEQRNGFIQSLKDDPSQSANLLAEA KKLNDAQAPKALINGGSGGSGGSGGSGGGMQIYEGKLTAEGLRFGIVA SRFNHALVDRLVEGAIDAIVRHGGREEDITLVRVPGSWEIPVAAGELA RKEDIDAVIAIGVLIRGATPHFDYIASEVSKGLAQLSLELRKPITFGV ITADTLEQAIERAGTKHGNKGWEAALSAIEMANLFKSLR | An exemplary VLP monomer polypeptide having a Protein A domain (in bold) + a linker (underlined) + a LS domain amino acid sequence |
| 16 | HHHHHHHH<u>SALA</u>ADNKFNKEQQNAFYEILHLPNLNEEQRNGFIQSLKD DPSQSANLLAEAKKLNDAQAPKA<u>LINGGSGGSGGSGGSGGG</u>MQIYEGK LTAEGLRFGIVASRFNHALVDRLVEGAIDAIVRHGGREEDITLVRVPG SWEIPVAAGELARKEDIDAVIAIGVLIRGATPHFDYIASEVSKGLAQL SLELRKPITFGVITADTLEQAIERAGTKHGNKGWEAALSAIEMANLFK SLR | An exemplary VLP monomer polypeptide having His8 tag + a linker (underlined) + a Protein A domain (in bold) + a linker (underlined) + a LS domain amino acid sequence |
| 17 | *MDAMKRGLCCVLLLCGAVFVSAS*HHHHHHHH<u>SALA</u>ADNKFNKEQQNAF YEILHLPNLNEEQRNGFIQSLKDDPSQSANLLAEAKKLNDAQAPKA<u>LI NGGSGGSGGSGGSGGG</u>MQIYEGKLTAEGLRFGIVASRFNHALVDRLVE GAIDAIVRHGGREEDITLVRVPGSWEIPVAAGELARKEDIDAVIAIGV LIRGATPHFDYIASEVSKGLAQLSLELRKPITFGVITADTLEQAIERA GTKHGNKGWEAALSAIEMANLFKSLR | An exemplary VLP monomer polypeptide having tPA signal peptide (in italics) + His8 tag + a linker (underlined) + a Protein A domain (in bold) + a linker (underlined) + a LS domain amino acid sequence |
| 18 | *ATGGACGCCATGAAAAGAGGCCTGTGCTGCGTGCTGCTGCTGTGTGGC GCCGTGTTCGTGTCCGCCTCT*CACCACCACCACCACCACCACCATTCT GCTCTCGCTGCTGATAACAAGTTCAACAAGGAACAGCAGAACGCCTTC TACGAGATCCTGCACCTGCCTAACCTGAACGAGGAACAGAGAAACGGC TTCATCCAGTCCCTGAAGGACGATCCTAGCCAGAGCGCTAATCTGCTG GCCGAGGCCAAGAAGCTGAACGACGCCCAGGCCCCTAAGGCCCTGATC <u>AACGGAGGAAGCGGCGGATCTGGCGGCAGCGGAGGCAGCGGCGGCGGC</u> ATGCAGATCTACGAGGGCAAGCTGACCGCCGAGGGCCTGAGGTTTGGC ATCGTGGCCAGCAGATTTAACGCCCTGGTCGACAGACTGGTGGAA GGCGCTATTGACGCCATTGTGCGGCACGGCGGAAGAGAGGAAGATATC ACCCTGGTGCGGGTGCCAGGCAGCTGGGAGATCCCCGTGGCCGCCGGC GAGCTGGCCAGAAAAGAGGACATCGATGCCGTGATCGCCATCGGCGTT CTGATCCGGGGCGCCACCCCTCACTTCGACTACATCGCCAGCGAGGTG TCTAAGGGCCTGGCTCAGCTGAGCCTGGAACTGAGAAAGCCCATCACC TTCGGCGTGATCACAGCCGACACCCTGGAACAAGCCATCGAGAGAGCC GGTACAAAGCATGGAAATAAAGGCTGGGAAGCCGCTCTCAGCGCCATC GAGATGGCCAATCTGTTCAAGAGCCTGCGG<u>TGA</u> | Nucleic acid encoding SEQ. ID NO 17: nucleotides in italics encode the tPA signal peptide; the nucleotides in bold/underline encode the His tag; nucleotides encoding linkers SEQ ID NOs: 9 and 10 are underlined; nucleotides in bold encode the proten A domain; nucleotides |

TABLE 2-continued

| SEQ ID NO: | Sequences | Comment |
|---|---|---|
| | | encoding the shaded nucleotides represent the stop codon, and the rest encodes the lumazine synthase domain. |
| 19 | *ATGGACGCCATGAAGAGGGGCCTGTGCTGCGTGCTGCTGCTGTGCGGC GCCGTGTTCGTGAGCGCCAGC*CGCGTGCAGCCAACCGAGAGCATCGTG CGCTTCCCCAATATCACCAACCTGTGCCCATTCGGCGAGGTGTTCAAC GCTACCAGGTTCGCCAGCGTGTACGCTTGGAATCGCAAGCGCATCTCC AACTGCGTGGCCGACTACAGCGTGCTGTACAACTCCGCCAGCTTCTCC ACCTTCAAGTGCTACGGCGTGTCCCCCACCAAGCTGAATGATCTGTGC TTCACCAACGTGTACGCCGATAGCTTCGTGATCAGGGGCGACGAGGTG CGCCAGATCGCTCCAGGACAGACCGGCAAGATCGCTGACTACAATTAC AAGCTGCCCGACGATTTCACCGGCTGCGTGATCGCCTGGAACTCCAAC AATCTGGATAGCAAAGTGGGCGGCAACTACAATTACCTGTACCGCCTG TTCCGCAAGTCCAATCTGAAGCCATTCGAGCGCGACATCTCCACCGAG ATCTACCAGGCTGGAAGCACCCCATGCAATGGAGTGGAGGGCTTCAAC TGCTACTTCCCCCTGCAGAGCTACGGCTTCCAGCCAACCAACGGAGTG GGATACCAGCCATACAGGGTGGTGGTGCTGTCCTTCGAGCTGCTGCAC GCTCCAGCTACCGTGTGCGGACCAAAGAAGAGCACCAATCTGGTGAAG CTCGAGGCATGCGGTACCCCCCATGCCCATCATGCCCAGCACCTGAG TTCCTGGGGGGACCATCAGTCTTCCTGTTCCCCCCAAAACCCAAGGAC ACTCTCATGATCTCCCGGACCCCTGAGGTCACGTGCGTGGTGGTGGAC GTGAGCCAGGAAGACCCCGAGGTCCAGTTCAACTGGTACGTGGATGGC GTGGAGGTGCATAATGCCAAGACAAAGCCGCGGGAGGAGCAGTTCAAC AGCACGTACCGTGTGGTCAGCGTCCTCACCGTCCTGCACCAGGACTGG CTGAACGGCAAGGAGTACAAGTGCAAGGTCTCCAACAAAGGCCTCCCG TCCTCCATCGAGAAAACCATCTCCAAAGCCAAAGGGCAGCCCCGAGAG CCACAGGTGTACACCCTGCCCCCATCCCAGGAGGAGATGACCAAGAAC CAGGTCAGCCTGACCTGCCTGGTCAAAGGCTTCTACCCCAGCGACATC GCCGTGGAGTGGGAGAGCAATGGGCAGCCGGAGAACAACTACAAGACC ACGCCTCCCGTGCTGGACTCCGACGGCTCCTTCTTCCTCTACAGCAGG CTAACCGTGGACAAGAGCAGGTGGCAGGAGGGGAATGTCTTCTCATGC TCCGTGATGCATGAGGCTCTGCACAACCACTACACACAGAAGAGCCTC TCCCTGTCTCTGGGTAAATGA | Nucleic acid encoding SEQ ID NO: 5; nucleotides in italics encode the tPA signal peptide; nucleotides in bold encode the SARS-CoV-2 RBD; nucleotides encoding linker SEQ ID NO: 8 is underlined; nucleotides encoding the shaded nucleotides represent the stop codon, and the rest encodes human I TABLE 2-continued

| SEQ ID NO: | Sequences | Comment |
|---|---|---|
| | GATACCACCGACGCCGTGCGCGACCCACAGACCCTGGAGATCCTGGAT<br>ATCACCCCATGCTCCTTCGGCGGCGTGAGCGTGATCACCCCAGGAACC<br>AATACCAGCAACCAGGTGGCCGTGCTGTACCAGGACGTGAATTGCACC<br>GAGGTGCCAGTGGCTATCCACGCTGATCAGCTGACCCCAACCTGGCGC<br>GTGTACAGCACCGGATCCAACGTGTTCCAGACCCGCGCCGGATGCCTG<br>ATCGGAGCTGAGCACGTGAACAATTCCTACGAGTGCGACATCCCAATC<br>GGAGCTGGAATCTGCGCCAGCTACCAGACCCAGACCAACTCCCCACTC<br>GAGGCATGCGGTACCCCCCCATGCCCATCATGCCCAGCACCTGAGTTC<br>CTGGGGGGACCATCAGTCTTCCTGTTCCCCCCAAAACCCAAGGACACT<br>CTCATGATCTCCCGGACCCCTGAGGTCACGTGCGTGGTGGTGGACGTG<br>AGCCAGGAAGACCCCGAGGTCCAGTTCAACTGGTACGTGGATGGCGTG<br>GAGGTGCATAATGCCAAGACAAAGCCGCGGGAGGAGCAGTTCAACAGC<br>ACGTACCGTGTGGTCAGCGTCCTCACCGTCCTGCACCAGGACTGGCTG<br>AACGGCAAGGAGTACAAGTGCAAGGTCTCCAACAAAGGCCTCCCGTCC<br>TCCATCGAGAAAACCATCTCCAAAGCCAAAGGGCAGCCCCGAGAGCCA<br>CAGGTGTACACCCTGCCCCCATCCCAGGAGGAGATGACCAAGAACCAG<br>GTCAGCCTGACCTGCCTGGTCAAAGGCTTCTACCCCAGCGACATCGCC<br>GTGGAGTGGGAGAGCAATGGGCAGCCGGAGAACAACTACAAGACCACG<br>CCTCCCGTGCTGGACTCCGACGGCTCCTTCTTCCTCTACAGCAGGCTA<br>ACCGTGGACAAGAGCAGGTGGCAGGAGGGGAATGTCTTCTCATGCTCC<br>GTGATGCATGAGGCTCTGCACAACCACTACACACAGAAGAGCCTCTCC<br>CTGTCTCTGGGTAAATGA | |
| 22 | MHHHHHHHHSALAADNKFNKEQQNAFYEILHLPNLNEEQRNGFIQSLK<br>DDPSQSANLLAEAKKLNDAQAPKALINGGSGGSGGSGGSGGGMQIYEG<br>KLTAEGLRFGIVASRFNHALVDRLVEGAIDAIVRHGGREEDITLVRVP<br>GSWEIPVAAGELARKEDIDAVIAIGVLIRGATPHFDYIASEVSKGLAQ<br>LSLELRKPITFGVITADTLEQAIERAGTKHGNKGWEAALSAIEMANLF<br>KSLR | An exemplary VLP monomer polypeptide having M(methionine, start codon, bold and underlined) + His8 tag + a linker (underlined) + a Protein A domain (in bold) + a linker (underlined) + a LS domain amino acid sequence |
| 23 | ATG*CACCACCACCACCACCACCACCAT*TCTGCTCTCGCTGCTGATAAC<br>AAGTTCAACAAGGAACAGCAGAACGCCTTCTACGAGATCCTGCACCTG<br>CCTAACCTGAACGAGGAACAGAGAAACGGCTTCATCCAGTCCCTGAAG<br>GACGATCCTAGCCAGAGCGCTAATCTGCTGGCCGAGGCCAAGAAGCTG<br>AACGACGCCCAGGCCCCTAAGGCCCTGATCAACGGAGGAAGCGGCGGA<br>TCTGGCGGCAGCGGAGGCAGCGGCGGCGGCATGCAGATCTACGAGGGC<br>AAGCTGACCGCCGAGGGCCTGAGGTTTGGCATCGTGGCCAGCAGATTT<br>AACCACGCCCTGGTCGACAGACTGGTGGAAGGCGCTATTGACGCCATT<br>GTGCGGCACGGCGGAAGAGAGGAAGATATCACCCTGGTGCGGGTGCCA<br>GGCAGCTGGGAGATCCCCGTGGCCGCCGGCGAGCTGGCCAGAAAAGAG<br>GACATCGATGCCGTGATCGCCATCGGCGTTCTGATCCGGGGCGCCACC<br>CCTCACTTCGACTACATCGCCAGCGAGGTGTCTAAGGGCCTGGCTCAG<br>CTGAGCCTGGAACTGAGAAAGCCCATCACCTTCGGCGTGATCACAGCC<br>GACACCCTGGAACAAGCCATCGAGAGAGCCGGTACAAAGCATGGAAAT<br>AAAGGCTGGGAAGCCGCTCTCAGCGCCATCGAGATGGCCAATCTGTTC<br>AAGAGCCTGCGGTGA | Nucleic acid encoding SEQ ID NO: 22: nucleotides in bold and underlined encode the methionine start codon; the nucleotides in italics encode the His8 tag; nucleotides encoding linkers SEQ ID NOs: 9 and 10 are underlined; nucleotides in bold encode the Protein A domain; nucleotides encoding the shaded nucleotides represent the stop codon, and the rest encodes the lumazine synthase domain. |
| 24 | EKGIYQTSNFRVQPTESIVRFPNITNLCPFGEVFNATRFASVYAWNRK<br>RISNCVADYSVLYNSASFSTFKCYGVSPTKLNDLCFTNVYADSFVIRG<br>DEVRQIAPGQTGKIADYNYKLPDDFTGCVIAWNSNNLDSKVGGNYNYL<br>YRLFRKSNLKPFERDISTEIYQAGSTPCNGVEGFNCYFPLQSYGFQPT<br>NGVGYQPYRVVVLSFELLHAPATVCGPKKSTNLVKNKCVNFNFNG | Certain protein sequence comprising SARS-CoV-2 RBD segment |
| 25 | FPNITNLCPFGEVFNATRFASVYAWNRKRISNCVADYSVLYNSASFST<br>FKCYGVSPTKLNDLCFTNVYADSFVIRGDEVRQIAPGQTGKIADYNYK<br>LPDDFTGCVIAWNSNNLDSKVGGNYNYLYRLFRKSNLKPFERDISTEI | SEQ ID NO: 1 without first 10 or last 10 residues; Protein |

TABLE 2-continued

| SEQ ID NO: | Sequences | Comment |
|---|---|---|
| | YQAGSTPCNGVEGFNCYFPLQSYGFQPTNGVGYQPYRVVVLSFELLHAPATVC | sequence of SARS-CoV-2 RBD segment (aa 329 to 525) |
| 26 | RVQPTESIVR | First 10 residues of SEQ ID NO: 1; Protein sequence of SARS-CoV-2 RBD segment (aa 319-328) |
| 27 | GPKKSTNLVK | Last 10 residues of SEQ ID NO: 1; Protein sequence of SARS-CoV-2 RBD segment (aa 526-535) |
| 28 | EKGIYQTSNF | First 10 residues of SEQ ID NO: 24; Protein sequence of SARS-CoV-2 RBD segment (aa 309-318) |
| 29 | NKCVNFNFNG | Last 10 residues of SEQ ID NO: 24; Protein sequence of SARS-CoV-2 RBD segment (aa 536-545) |

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and "or" and similar referents in the context of describing the invention are to be construed to cover both the singular and the plural, unless otherwise indicated herein or clearly contradicted by context. Thus, for example, reference to "a subject polypeptide" includes a plurality of such polypeptides and reference to "the agent" includes reference to one or more agents and equivalents thereof known to those skilled in the art, and so forth.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventor for carrying out the invention. Variations of those embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention. Further, all publications mentioned herein are incorporated by reference in their entireties.

What is claimed is:

1. A virus-like nanoparticle (VLP) comprising:
   1) a plurality of oligomerized VLP monomer polypeptides, wherein each VLP monomer polypeptide comprises an Fc binding domain amino acid sequence operably linked to a lumazine synthase (LS) amino acid sequence; and
   2) a plurality of S-antigen-Fc polypeptides, wherein each S-antigen-Fc polypeptide comprises a SARS-CoV-2 Spike protein domain amino acid sequence operably linked to a Fc domain amino acid sequence.

2. The VLP of claim 1, wherein the LS amino acid sequence is derived from the LS of *Aquifex aeolicus*, *Brucella* spp., *Brucella abortus*, or *Bacillus anthracis*.

3. The VLP of claim 1, wherein the LS amino acid sequence comprises an amino acid sequence having at least about 90% sequence identity to SEQ ID NO:12.

4. The VLP of claim 1, wherein the Fc binding domain amino acid sequence comprises a Protein A domain sequence.

5. The VLP of claim 4, wherein the Protein A domain sequence comprises an amino acid sequence having at least about 90% sequence identity to SEQ ID NO:11.

6. The VLP of claim 1, wherein the VLP monomer polypeptide further comprises one or more linker group(s), an affinity tag and/or a signal peptide sequence.

7. The VLP of claim 1, wherein the Fc binding domain amino acid sequence is operably linked to the lumazine synthase (LS) amino acid sequence via a linker group.

8. The VLP of claim 1, wherein the VLP monomer polypeptide comprises an amino acid sequence having at least about 90% sequence identity to SEQ ID NO:15, 16, 17 or 22.

9. The VLP of claim 1, wherein the SARS-CoV-2 Spike protein domain amino acid sequence comprises a SARS-CoV-2 receptor binding domain (RBD) amino acid sequence or SARS-CoV-2 S1 amino acid sequence.

10. The VLP of claim 1, wherein the SARS-CoV-2 Spike protein domain amino acid sequence comprises an amino acid sequence having at least about 90% sequence identity to SEQ ID NO:1, or SEQ ID NO:2.

11. The VLP of claim 10, wherein the SARS-CoV-2 Spike protein domain amino acid sequence comprises SEQ ID NO:1.

12. The VLP of claim 1, wherein the S-antigen-Fc polypeptide further comprises one or more linker group(s) and/or a signal peptide sequence.

13. The VLP of claim 1, wherein the SARS-CoV-2 Spike protein domain amino acid sequence is operably linked to the Fc domain amino acid sequence via a linker group.

14. The VLP of claim 1, wherein the Fc domain amino acid sequence comprises a human IgG1, IgG2, IgG3 or IgG4 Fc domain amino acid sequence.

15. The VLP of claim 1, wherein the Fc domain amino acid sequence comprises an amino acid sequence having at least about 90% sequence identity to SEQ ID NO:4.

16. The VLP of claim 1, wherein the S-antigen-Fc polypeptide comprises an amino acid sequence having at least about 90% sequence identity to SEQ ID NO:5, 6, 7, or 21.

17. A pharmaceutical composition comprising a VLP as described in claim 1 and a pharmaceutically acceptable carrier.

18. The composition of 17, which is a vaccine composition comprising one or more adjuvant(s).

19. A method of eliciting a coronavirus neutralizing antibody response in an animal, comprising administering a first dose of an effective amount of a VLP as described in claim 1 to the animal.

20. The method of claim 19, wherein the coronavirus is SARS-CoV-1, SARS-CoV-1-like bat coronavirus, or SARS-CoV-2.

21. The method of claim 20, wherein the coronavirus is SARS-CoV-2.

22. The method of claim 21, wherein the SARS-CoV-2 is a SARS-CoV-2 variant.

23. The method of claim 19, further comprising administering to the animal at least one additional agent.

24. The method of claim 23, wherein the at least one additional agent is an adjuvant, and wherein the adjuvant is selected from the group consisting of monophosphoryl lipid A, aluminum salt, Complete Freund's Adjuvant (CFA), Incomplete Freund's Adjuvant (IFA), MF59, Montanide ISA 51, CpG, Glucopyranosyl Lipid Adjuvant (GLA), QS-21, and combinations thereof.

25. A method of treating a coronavirus infection in an animal, comprising administering a first dose of the composition of claim 17 to the animal.

26. The VLP of claim 1, wherein the plurality of S-antigen-Fc polypeptides comprises 120 copies of the S-antigen-Fc polypeptide.

27. The VLP of claim 26, wherein the S-antigen-Fc polypeptide comprises an amino acid sequence having at least about 95% sequence identity to SEQ ID NO:6.

28. The VLP of claim 27, wherein the VLP monomer polypeptide comprises an amino acid sequence having at least about 95% sequence identity to SEQ ID NO:15.

* * * * *

```
                         SEQUENCE LISTING

<160> NUMBER OF SEQ ID NOS: 57

<210> SEQ ID NO 1
<211> LENGTH: 217
<212> TYPE: PRT
<213> ORGANISM: Severe acute respiratory syndrome coronavirus 2

<400> SEQUENCE: 1

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys
    210                 215

<210> SEQ ID NO 2
<211> LENGTH: 664
<212> TYPE: PRT
<213> ORGANISM: Severe acute respiratory syndrome coronavirus 2

<400> SEQUENCE: 2

Leu Thr Thr Arg Thr Gln Leu Pro Pro Ala Tyr Thr Asn Ser Phe Thr
1               5                   10                  15

Arg Gly Val Tyr Tyr Pro Asp Lys Val Phe Arg Ser Ser Val Leu His
            20                  25                  30

Ser Thr Gln Asp Leu Phe Leu Pro Phe Phe Ser Asn Val Thr Trp Phe
        35                  40                  45
```

```
His Ala Ile His Val Ser Gly Thr Asn Gly Thr Lys Arg Phe Asp Asn
 50                  55                  60

Pro Val Leu Pro Phe Asn Asp Gly Val Tyr Phe Ala Ser Thr Glu Lys
 65                  70                  75                  80

Ser Asn Ile Ile Arg Gly Trp Ile Phe Gly Thr Thr Leu Asp Ser Lys
                 85                  90                  95

Thr Gln Ser Leu Leu Ile Val Asn Asn Ala Thr Asn Val Val Ile Lys
            100                 105                 110

Val Cys Glu Phe Gln Phe Cys Asn Asp Pro Phe Leu Gly Val Tyr Tyr
        115                 120                 125

His Lys Asn Asn Lys Ser Trp Met Glu Ser Glu Phe Arg Val Tyr Ser
    130                 135                 140

Ser Ala Asn Asn Cys Thr Phe Glu Tyr Val Ser Gln Pro Phe Leu Met
145                 150                 155                 160

Asp Leu Glu Gly Lys Gln Gly Asn Phe Lys Asn Leu Arg Glu Phe Val
                165                 170                 175

Phe Lys Asn Ile Asp Gly Tyr Phe Lys Ile Tyr Ser Lys His Thr Pro
            180                 185                 190

Ile Asn Leu Val Arg Asp Leu Pro Gln Gly Phe Ser Ala Leu Glu Pro
        195                 200                 205

Leu Val Asp Leu Pro Ile Gly Ile Asn Ile Thr Arg Phe Gln Thr Leu
    210                 215                 220

Leu Ala Leu His Arg Ser Tyr Leu Thr Pro Gly Asp Ser Ser Ser Gly
225                 230                 235                 240

Trp Thr Ala Gly Ala Ala Ala Tyr Tyr Val Gly Tyr Leu Gln Pro Arg
                245                 250                 255

Thr Phe Leu Leu Lys Tyr Asn Glu Asn Gly Thr Ile Thr Asp Ala Val
            260                 265                 270

Asp Cys Ala Leu Asp Pro Leu Ser Glu Thr Lys Cys Thr Leu Lys Ser
        275                 280                 285

Phe Thr Val Glu Lys Gly Ile Tyr Gln Thr Ser Asn Phe Arg Val Gln
    290                 295                 300

Pro Thr Glu Ser Ile Val Arg Phe Pro Asn Ile Thr Asn Leu Cys Pro
305                 310                 315                 320

Phe Gly Glu Val Phe Asn Ala Thr Arg Phe Ala Ser Val Tyr Ala Trp
                325                 330                 335

Asn Arg Lys Arg Ile Ser Asn Cys Val Ala Asp Tyr Ser Val Leu Tyr
            340                 345                 350

Asn Ser Ala Ser Phe Ser Thr Phe Lys Cys Tyr Gly Val Ser Pro Thr
        355                 360                 365

Lys Leu Asn Asp Leu Cys Phe Thr Asn Val Tyr Ala Asp Ser Phe Val
    370                 375                 380

Ile Arg Gly Asp Glu Val Arg Gln Ile Ala Pro Gly Gln Thr Gly Lys
385                 390                 395                 400

Ile Ala Asp Tyr Asn Tyr Lys Leu Pro Asp Asp Phe Thr Gly Cys Val
                405                 410                 415

Ile Ala Trp Asn Ser Asn Asn Leu Asp Ser Lys Val Gly Gly Asn Tyr
            420                 425                 430

Asn Tyr Leu Tyr Arg Leu Phe Arg Lys Ser Asn Leu Lys Pro Phe Glu
        435                 440                 445

Arg Asp Ile Ser Thr Glu Ile Tyr Gln Ala Gly Ser Thr Pro Cys Asn
    450                 455                 460
```

Gly Val Glu Gly Phe Asn Cys Tyr Phe Pro Leu Gln Ser Tyr Gly Phe
465                 470                 475                 480

Gln Pro Thr Asn Gly Val Gly Tyr Gln Pro Tyr Arg Val Val Val Leu
            485                 490                 495

Ser Phe Glu Leu Leu His Ala Pro Ala Thr Val Cys Gly Pro Lys Lys
            500                 505                 510

Ser Thr Asn Leu Val Lys Asn Lys Cys Val Asn Phe Asn Phe Asn Gly
            515                 520                 525

Leu Thr Gly Thr Gly Val Leu Thr Glu Ser Asn Lys Lys Phe Leu Pro
            530                 535                 540

Phe Gln Gln Phe Gly Arg Asp Ile Ala Asp Thr Thr Asp Ala Val Arg
545                 550                 555                 560

Asp Pro Gln Thr Leu Glu Ile Leu Asp Ile Thr Pro Cys Ser Phe Gly
            565                 570                 575

Gly Val Ser Val Ile Thr Pro Gly Thr Asn Thr Ser Asn Gln Val Ala
            580                 585                 590

Val Leu Tyr Gln Asp Val Asn Cys Thr Glu Val Pro Val Ala Ile His
            595                 600                 605

Ala Asp Gln Leu Thr Pro Thr Trp Arg Val Tyr Ser Thr Gly Ser Asn
610                 615                 620

Val Phe Gln Thr Arg Ala Gly Cys Leu Ile Gly Ala Glu His Val Asn
625                 630                 635                 640

Asn Ser Tyr Glu Cys Asp Ile Pro Ile Gly Ala Gly Ile Cys Ala Ser
            645                 650                 655

Tyr Gln Thr Gln Thr Asn Ser Pro
            660

<210> SEQ ID NO 3
<211> LENGTH: 1273
<212> TYPE: PRT
<213> ORGANISM: Severe acute respiratory syndrome coronavirus 2

<400> SEQUENCE: 3

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

```
Met Asp Leu Glu Gly Lys Gln Gly Asn Phe Lys Asn Leu Arg Glu Phe
            180                 185                 190
Val Phe Lys Asn Ile Asp Gly Tyr Phe Lys Ile Tyr Ser Lys His Thr
        195                 200                 205
Pro Ile Asn Leu Val Arg Asp Leu Pro Gln Gly Phe Ser Ala Leu Glu
    210                 215                 220
Pro Leu Val Asp Leu Pro Ile Gly Ile Asn Ile Thr Arg Phe Gln Thr
225                 230                 235                 240
Leu Leu Ala Leu His Arg Ser Tyr Leu Thr Pro Gly Asp Ser Ser Ser
                245                 250                 255
Gly Trp Thr Ala Gly Ala Ala Ala Tyr Tyr Val Gly Tyr Leu Gln Pro
            260                 265                 270
Arg Thr Phe Leu Leu Lys Tyr Asn Glu Asn Gly Thr Ile Thr Asp Ala
        275                 280                 285
Val Asp Cys Ala Leu Asp Pro Leu Ser Glu Thr Lys Cys Thr Leu Lys
    290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
                325                 330                 335
Pro Phe Gly Glu Val Phe Asn Ala Thr Arg Phe Ala Ser Val Tyr Ala
            340                 345                 350
Trp Asn Arg Lys Arg Ile Ser Asn Cys Val Ala Asp Tyr Ser Val Leu
        355                 360                 365
Tyr Asn Ser Ala Ser Phe Ser Thr Phe Lys Cys Tyr Gly Val Ser Pro
    370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
        435                 440                 445
Tyr Asn Tyr Leu Tyr Arg Leu Phe Arg Lys Ser Asn Leu Lys Pro Phe
    450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
                485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
        515                 520                 525
Lys Ser Thr Asn Leu Val Lys Asn Lys Cys Val Asn Phe Asn Phe Asn
    530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
                565                 570                 575
Arg Asp Pro Gln Thr Leu Glu Ile Leu Asp Ile Thr Pro Cys Ser Phe
            580                 585                 590
```

-continued

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

```
Thr Gln Gln Leu Ile Arg Ala Ala Glu Ile Arg Ala Ser Ala Asn
    1010            1015                1020

Leu Ala Ala Thr Lys Met Ser Glu Cys Val Leu Gly Gln Ser Lys
    1025            1030                1035

Arg Val Asp Phe Cys Gly Lys Gly Tyr His Leu Met Ser Phe Pro
    1040            1045                1050

Gln Ser Ala Pro His Gly Val Val Phe Leu His Val Thr Tyr Val
    1055            1060                1065

Pro Ala Gln Glu Lys Asn Phe Thr Thr Ala Pro Ala Ile Cys His
    1070            1075                1080

Asp Gly Lys Ala His Phe Pro Arg Glu Gly Val Phe Val Ser Asn
    1085            1090                1095

Gly Thr His Trp Phe Val Thr Gln Arg Asn Phe Tyr Glu Pro Gln
    1100            1105                1110

Ile Ile Thr Thr Asp Asn Thr Phe Val Ser Gly Asn Cys Asp Val
    1115            1120                1125

Val Ile Gly Ile Val Asn Asn Thr Val Tyr Asp Pro Leu Gln Pro
    1130            1135                1140

Glu Leu Asp Ser Phe Lys Glu Glu Leu Asp Lys Tyr Phe Lys Asn
    1145            1150                1155

His Thr Ser Pro Asp Val Asp Leu Gly Asp Ile Ser Gly Ile Asn
    1160            1165                1170

Ala Ser Val Val Asn Ile Gln Lys Glu Ile Asp Arg Leu Asn Glu
    1175            1180                1185

Val Ala Lys Asn Leu Asn Glu Ser Leu Ile Asp Leu Gln Glu Leu
    1190            1195                1200

Gly Lys Tyr Glu Gln Tyr Ile Lys Trp Pro Trp Tyr Ile Trp Leu
    1205            1210                1215

Gly Phe Ile Ala Gly Leu Ile Ala Ile Val Met Val Thr Ile Met
    1220            1225                1230

Leu Cys Cys Met Thr Ser Cys Cys Ser Cys Leu Lys Gly Cys Cys
    1235            1240                1245

Ser Cys Gly Ser Cys Cys Lys Phe Asp Glu Asp Asp Ser Glu Pro
    1250            1255                1260

Val Leu Lys Gly Val Lys Leu His Tyr Thr
    1265            1270

<210> SEQ ID NO 4
<211> LENGTH: 224
<212> TYPE: PRT
<213> ORGANISM: Homo sapiens

<400> SEQUENCE: 4

Pro Pro Cys Pro Ser Cys Pro Ala Pro Glu Phe Leu Gly Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser Gln Glu Asp Pro
            35                  40                  45

Glu Val Gln Phe Asn Trp Tyr Val Asp Gly Val Glu Val His Asn Ala
        50                  55                  60

Lys Thr Lys Pro Arg Glu Glu Gln Phe Asn Ser Thr Tyr Arg Val Val
65                  70                  75                  80
```

```
Ser Val Leu Thr Val Leu His Gln Asp Trp Leu Asn Gly Lys Glu Tyr
                85                  90                  95

Lys Cys Lys Val Ser Asn Lys Gly Leu Pro Ser Ser Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Gln Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Arg Leu Thr Val Asp Lys Ser
            180                 185                 190

Arg Trp Gln Glu Gly Asn Val Phe Ser Cys Ser Val Met His Glu Ala
        195                 200                 205

Leu His Asn His Tyr Thr Gln Lys Ser Leu Ser Leu Ser Leu Gly Lys
    210                 215                 220
```

<210> SEQ ID NO 5
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Asp Ala Met Lys Arg Gly Leu Cys Cys Val Leu Leu Leu Cys Gly
1               5                   10                  15

Ala Val Phe Val Ser Ala Ser Arg Val Gln Pro Thr Glu Ser Ile Val
            20                  25                  30

Arg Phe Pro Asn Ile Thr Asn Leu Cys Pro Phe Gly Glu Val Phe Asn
        35                  40                  45

Ala Thr Arg Phe Ala Ser Val Tyr Ala Trp Asn Arg Lys Arg Ile Ser
    50                  55                  60

Asn Cys Val Ala Asp Tyr Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205
```

Gly Tyr Gln Pro Tyr Arg Val Val Leu Ser Phe Glu Leu Leu His
210                 215                 220

Ala Pro Ala Thr Val Cys Gly Pro Lys Lys Ser Thr Asn Leu Val Lys
225                 230                 235                 240

Leu Glu Ala Cys Gly Thr Pro Pro Cys Pro Ser Cys Pro Ala Pro Glu
            245                 250                 255

Phe Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser Gln Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Gly Leu Pro
            340                 345                 350

Ser Ser Ile Glu Lys Thr Ile Ser Lys Ala Lys Gly Gln Pro Arg Glu
            355                 360                 365

Pro Gln Val Tyr Thr Leu Pro Pro Ser Gln Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Arg
            420                 425                 430

Leu Thr Val Asp Lys Ser Arg Trp Gln Glu Gly Asn Val Phe Ser Cys
            435                 440                 445

Ser Val Met His Glu Ala Leu His Asn His Tyr Thr Gln Lys Ser Leu
450                 455                 460

Ser Leu Ser Leu Gly Lys
465                 470

<210> SEQ ID NO 6
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Leu Glu Ala Cys Gly Thr Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 7
<211> LENGTH: 894
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 7

Leu Thr Thr Arg Thr Gln Leu Pro Pro Ala Tyr Thr Asn Ser Phe Thr
1               5                   10                  15

Arg Gly Val Tyr Tyr Pro Asp Lys Val Phe Arg Ser Ser Val Leu His
            20                  25                  30

Ser Thr Gln Asp Leu Phe Leu Pro Phe Phe Ser Asn Val Thr Trp Phe
        35                  40                  45

His Ala Ile His Val Ser Gly Thr Asn Gly Thr Lys Arg Phe Asp Asn
    50                  55                  60

Pro Val Leu Pro Phe Asn Asp Gly Val Tyr Phe Ala Ser Thr Glu Lys
65                  70                  75                  80

Ser Asn Ile Ile Arg Gly Trp Ile Phe Gly Thr Thr Leu Asp Ser Lys
                85                  90                  95

Thr Gln Ser Leu Leu Ile Val Asn Asn Ala Thr Asn Val Val Ile Lys
            100                 105                 110

Val Cys Glu Phe Gln Phe Cys Asn Asp Pro Phe Leu Gly Val Tyr Tyr
        115                 120                 125

His Lys Asn Asn Lys Ser Trp Met Glu Ser Glu Phe Arg Val Tyr Ser
    130                 135                 140

Ser Ala Asn Asn Cys Thr Phe Glu Tyr Val Ser Gln Pro Phe Leu Met
145                 150                 155                 160

Asp Leu Glu Gly Lys Gln Gly Asn Phe Lys Asn Leu Arg Glu Phe Val
                165                 170                 175

Phe Lys Asn Ile Asp Gly Tyr Phe Lys Ile Tyr Ser Lys His Thr Pro
            180                 185                 190

Ile Asn Leu Val Arg Asp Leu Pro Gln Gly Phe Ser Ala Leu Glu Pro
        195                 200                 205

Leu Val Asp Leu Pro Ile Gly Ile Asn Ile Thr Arg Phe Gln Thr Leu
    210                 215                 220

Leu Ala Leu His Arg Ser Tyr Leu Thr Pro Gly Asp Ser Ser Ser Gly
225                 230                 235                 240

Trp Thr Ala Gly Ala Ala Ala Tyr Tyr Val Gly Tyr Leu Gln Pro Arg
                245                 250                 255

Thr Phe Leu Leu Lys Tyr Asn Glu Asn Gly Thr Ile Thr Asp Ala Val
            260                 265                 270

Asp Cys Ala Leu Asp Pro Leu Ser Glu Thr Lys Cys Thr Leu Lys Ser
        275                 280                 285

Phe Thr Val Glu Lys Gly Ile Tyr Gln Thr Ser Asn Phe Arg Val Gln
    290                 295                 300

Pro Thr Glu Ser Ile Val Arg Phe Pro Asn Ile Thr Asn Leu Cys Pro
305                 310                 315                 320

Phe Gly Glu Val Phe Asn Ala Thr Arg Phe Ala Ser Val Tyr Ala Trp
                325                 330                 335

Asn Arg Lys Arg Ile Ser Asn Cys Val Ala Asp Tyr Ser Val Leu Tyr
            340                 345                 350

Asn Ser Ala Ser Phe Ser Thr Phe Lys Cys Tyr Gly Val Ser Pro Thr
        355                 360                 365

Lys Leu Asn Asp Leu Cys Phe Thr Asn Val Tyr Ala Asp Ser Phe Val
    370                 375                 380

Ile Arg Gly Asp Glu Val Arg Gln Ile Ala Pro Gly Gln Thr Gly Lys
385                 390                 395                 400

Ile Ala Asp Tyr Asn Tyr Lys Leu Pro Asp Asp Phe Thr Gly Cys Val
                405                 410                 415
```

```
Ile Ala Trp Asn Ser Asn Asn Leu Asp Ser Lys Val Gly Gly Asn Tyr
                420                 425                 430

Asn Tyr Leu Tyr Arg Leu Phe Arg Lys Ser Asn Leu Lys Pro Phe Glu
        435                 440                 445

Arg Asp Ile Ser Thr Glu Ile Tyr Gln Ala Gly Ser Thr Pro Cys Asn
    450                 455                 460

Gly Val Glu Gly Phe Asn Cys Tyr Phe Pro Leu Gln Ser Tyr Gly Phe
465                 470                 475                 480

Gln Pro Thr Asn Gly Val Gly Tyr Gln Pro Tyr Arg Val Val Val Leu
                485                 490                 495

Ser Phe Glu Leu Leu His Ala Pro Ala Thr Val Cys Gly Pro Lys Lys
        500                 505                 510

Ser Thr Asn Leu Val Lys Asn Lys Cys Val Asn Phe Asn Phe Asn Gly
    515                 520                 525

Leu Thr Gly Thr Gly Val Leu Thr Glu Ser Asn Lys Lys Phe Leu Pro
530                 535                 540

Phe Gln Gln Phe Gly Arg Asp Ile Ala Asp Thr Thr Asp Ala Val Arg
545                 550                 555                 560

Asp Pro Gln Thr Leu Glu Ile Leu Asp Ile Thr Pro Cys Ser Phe Gly
                565                 570                 575

Gly Val Ser Val Ile Thr Pro Gly Thr Asn Thr Ser Asn Gln Val Ala
        580                 585                 590

Val Leu Tyr Gln Asp Val Asn Cys Thr Glu Val Pro Val Ala Ile His
    595                 600                 605

Ala Asp Gln Leu Thr Pro Thr Trp Arg Val Tyr Ser Thr Gly Ser Asn
610                 615                 620

Val Phe Gln Thr Arg Ala Gly Cys Leu Ile Gly Ala Glu His Val Asn
625                 630                 635                 640

Asn Ser Tyr Glu Cys Asp Ile Pro Ile Gly Ala Gly Ile Cys Ala Ser
                645                 650                 655

Tyr Gln Thr Gln Thr Asn Ser Pro Leu Glu Ala Cys Gly Thr Pro Pro
        660                 665                 670

Cys Pro Ser Cys Pro Ala Pro Glu Phe Leu Gly Gly Pro Ser Val Phe
    675                 680                 685

Leu Phe Pro Pro Lys Pro Lys Asp Thr Leu Met Ile Ser Arg Thr Pro
690                 695                 700

Glu Val Thr Cys Val Val Val Asp Val Ser Gln Glu Asp Pro Glu Val
705                 710                 715                 720

Gln Phe Asn Trp Tyr Val Asp Gly Val Glu Val His Asn Ala Lys Thr
                725                 730                 735

Lys Pro Arg Glu Glu Gln Phe Asn Ser Thr Tyr Arg Val Val Ser Val
        740                 745                 750

Leu Thr Val Leu His Gln Asp Trp Leu Asn Gly Lys Glu Tyr Lys Cys
    755                 760                 765

Lys Val Ser Asn Lys Gly Leu Pro Ser Ser Ile Glu Lys Thr Ile Ser
770                 775                 780

Lys Ala Lys Gly Gln Pro Arg Glu Pro Gln Val Tyr Thr Leu Pro Pro
785                 790                 795                 800

Ser Gln Glu Glu Met Thr Lys Asn Gln Val Ser Leu Thr Cys Leu Val
                805                 810                 815

Lys Gly Phe Tyr Pro Ser Asp Ile Ala Val Glu Trp Glu Ser Asn Gly
        820                 825                 830
```

```
Gln Pro Glu Asn Asn Tyr Lys Thr Thr Pro Pro Val Leu Asp Ser Asp
                835                 840                 845

Gly Ser Phe Phe Leu Tyr Ser Arg Leu Thr Val Asp Lys Ser Arg Trp
        850                 855                 860

Gln Glu Gly Asn Val Phe Ser Cys Ser Val Met His Glu Ala Leu His
865                 870                 875                 880

Asn His Tyr Thr Gln Lys Ser Leu Ser Leu Ser Leu Gly Lys
                885                 890
```

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Glu Ala Cys Gly Thr
1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ala Leu Ala
1
```

```
<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Ile Asn Gly Gly Ser Gly Gly Ser Gly Gly Ser Gly Gly Ser Gly
1               5                   10                  15

Gly Gly
```

```
<210> SEQ ID NO 11
<211> LENGTH: 59
<212> TYPE: PRT
<213> ORGANISM: Staphylococcus aureus

<400> SEQUENCE: 11

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55
```

```
<210> SEQ ID NO 12
<211> LENGTH: 154
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Gln Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 13

His His His His His His His His
1               5

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Asp Ala Met Lys Arg Gly Leu Cys Cys Val Leu Leu Leu Cys Gly
1               5                   10                  15

Ala Val Phe Val Ser Ala Ser
            20

<210> SEQ ID NO 15
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala Leu Ile Asn Gly Gly
50                  55                  60

Ser Gly Gly Ser Gly Gly Ser Gly Gly Ser Gly Gly Met Gln Ile
65                  70                  75                  80

Tyr Glu Gly Lys Leu Thr Ala Glu Gly Leu Arg Phe Gly Ile Val Ala
                85                  90                  95

Ser Arg Phe Asn His Ala Leu Val Asp Arg Leu Val Glu Gly Ala Ile
            100                 105                 110

Asp Ala Ile Val Arg His Gly Gly Arg Glu Glu Asp Ile Thr Leu Val
            115                 120                 125

Arg Val Pro Gly Ser Trp Glu Ile Pro Val Ala Ala Gly Glu Leu Ala
130                 135                 140

Arg Lys Glu Asp Ile Asp Ala Val Ile Ala Ile Gly Val Leu Ile Arg
145                 150                 155                 160

Gly Ala Thr Pro His Phe Asp Tyr Ile Ala Ser Glu Val Ser Lys Gly
                165                 170                 175

Leu Ala Gln Leu Ser Leu Glu Leu Arg Lys Pro Ile Thr Phe Gly Val
            180                 185                 190

Ile Thr Ala Asp Thr Leu Glu Gln Ala Ile Glu Arg Ala Gly Thr Lys
        195                 200                 205

His Gly Asn Lys Gly Trp Glu Ala Ala Leu Ser Ala Ile Glu Met Ala
    210                 215                 220

Asn Leu Phe Lys Ser Leu Arg
225                 230

<210> SEQ ID NO 16
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

His His His His His His His Ser Ala Leu Ala Ala Asp Asn Lys
1               5                   10                  15

Phe Asn Lys Glu Gln Gln Asn Ala Phe Tyr Glu Ile Leu His Leu Pro
            20                  25                  30

Asn Leu Asn Glu Glu Gln Arg Asn Gly Phe Ile Gln Ser Leu Lys Asp
        35                  40                  45

Asp Pro Ser Gln Ser Ala Asn Leu Leu Ala Glu Ala Lys Lys Leu Asn
50                  55                  60

Asp Ala Gln Ala Pro Lys Ala Leu Ile Asn Gly Gly Ser Gly Gly Ser
65                  70                  75                  80

Gly Gly Ser Gly Gly Ser Gly Gly Met Gln Ile Tyr Glu Gly Lys
                85                  90                  95

Leu Thr Ala Glu Gly Leu Arg Phe Gly Ile Val Ala Ser Arg Phe Asn
            100                 105                 110

```
His Ala Leu Val Asp Arg Leu Val Glu Gly Ala Ile Asp Ala Ile Val
        115                 120                 125

Arg His Gly Gly Arg Glu Glu Asp Ile Thr Leu Val Arg Val Pro Gly
    130                 135                 140

Ser Trp Glu Ile Pro Val Ala Ala Gly Glu Leu Ala Arg Lys Glu Asp
145                 150                 155                 160

Ile Asp Ala Val Ile Ala Ile Gly Val Leu Ile Arg Gly Ala Thr Pro
                165                 170                 175

His Phe Asp Tyr Ile Ala Ser Glu Val Ser Lys Gly Leu Ala Gln Leu
            180                 185                 190

Ser Leu Glu Leu Arg Lys Pro Ile Thr Phe Gly Val Ile Thr Ala Asp
        195                 200                 205

Thr Leu Glu Gln Ala Ile Glu Arg Ala Gly Thr Lys His Gly Asn Lys
    210                 215                 220

Gly Trp Glu Ala Ala Leu Ser Ala Ile Glu Met Ala Asn Leu Phe Lys
225                 230                 235                 240

Ser Leu Arg

<210> SEQ ID NO 17
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Ala Met Lys Arg Gly Leu Cys Cys Val Leu Leu Leu Cys Gly
1               5                   10                  15

Ala Val Phe Val Ser Ala Ser His His His His His His Ser
            20                  25                  30

Ala Leu Ala Ala Asp Asn Lys Phe Asn Lys Glu Gln Gln Asn Ala Phe
        35                  40                  45

Tyr Glu Ile Leu His Leu Pro Asn Leu Asn Glu Glu Gln Arg Asn Gly
    50                  55                  60

Phe Ile Gln Ser Leu Lys Asp Asp Pro Ser Gln Ser Ala Asn Leu Leu
65                  70                  75                  80

Ala Glu Ala Lys Lys Leu Asn Asp Ala Gln Ala Pro Lys Ala Leu Ile
                85                  90                  95

Asn Gly Gly Ser Gly Gly Ser Gly Gly Ser Gly Gly Ser Gly Gly Gly
            100                 105                 110

Met Gln Ile Tyr Glu Gly Lys Leu Thr Ala Glu Gly Leu Arg Phe Gly
        115                 120                 125

Ile Val Ala Ser Arg Phe Asn His Ala Leu Val Asp Arg Leu Val Glu
    130                 135                 140

Gly Ala Ile Asp Ala Ile Val Arg His Gly Gly Arg Glu Glu Asp Ile
145                 150                 155                 160

Thr Leu Val Arg Val Pro Gly Ser Trp Glu Ile Pro Val Ala Ala Gly
                165                 170                 175

Glu Leu Ala Arg Lys Glu Asp Ile Asp Ala Val Ile Ala Ile Gly Val
            180                 185                 190

Leu Ile Arg Gly Ala Thr Pro His Phe Asp Tyr Ile Ala Ser Glu Val
        195                 200                 205

Ser Lys Gly Leu Ala Gln Leu Ser Leu Glu Leu Arg Lys Pro Ile Thr
    210                 215                 220
```

```
Phe Gly Val Ile Thr Ala Asp Thr Leu Glu Gln Ala Ile Glu Arg Ala
225                 230                 235                 240

Gly Thr Lys His Gly Asn Lys Gly Trp Glu Ala Ala Leu Ser Ala Ile
            245                 250                 255

Glu Met Ala Asn Leu Phe Lys Ser Leu Arg
            260                 265
```

<210> SEQ ID NO 18
<211> LENGTH: 801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| | | |
|---|---|---|
| atggacgcca tgaaaagagg cctgtgctgc gtgctgctgc tgtgtggcgc cgtgttcgtg | 60 |
| tccgcctctc accaccacca ccaccaccac cattctgctc tcgctgctga taacaagttc | 120 |
| aacaaggaac agcagaacgc cttctacgag atcctgcacc tgcctaacct gaacgaggaa | 180 |
| cagagaaacg gcttcatcca gtccctgaag gacgatccta gccagagcgc taatctgctg | 240 |
| gccgaggcca agaagctgaa cgacgcccag gcccctaagg ccctgatcaa cggaggaagc | 300 |
| ggcggatctg gcggcagcgg aggcagcggc ggcggcatgc agatctacga gggcaagctg | 360 |
| accgccgagg gcctgaggtt tggcatcgtg gccagcagat ttaaccacgc cctggtcgac | 420 |
| agactggtgg aaggcgctat tgacgccatt gtgcggcacg gcggaagaga ggaagatatc | 480 |
| accctggtgc gggtgccagg cagctgggag atccccgtgg ccgccggcga gctggccaga | 540 |
| aaagaggaca tcgatgccgt gatcgccatc ggcgttctga tccggggcgc cacccctcac | 600 |
| ttcgactaca tcgccagcga ggtgtctaag ggcctggctc agctgagcct ggaactgaga | 660 |
| aagcccatca ccttcggcgt gatcacagcc gacaccctgg aacaagccat cgagagagcc | 720 |
| ggtacaaagc atggaaataa aggctgggaa gccgctctca gcgccatcga gatggccaat | 780 |
| ctgttcaaga gcctgcggtg a | 801 |

<210> SEQ ID NO 19
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | | |
|---|---|---|
| atggacgcca tgaagagggg cctgtgctgc gtgctgctgc tgtgcggcgc cgtgttcgtg | 60 |
| agcgccagcc gcgtgcagcc aaccgagagc atcgtgcgct cccccaatat caccaacctg | 120 |
| tgcccattcg gcgaggtgtt caacgctacc aggttcgcca gcgtgtacgc ttggaatcgc | 180 |
| aagcgcatct ccaactgcgt ggccgactac agcgtgctgt acaactccgc cagcttctcc | 240 |
| accttcaagt gctacggcgt gtcccccacc aagctgaatg atctgtgctt caccaacgtg | 300 |
| tacgccgata gcttcgtgat caggggcgac gaggtgcgcc agatcgctcc aggacagacc | 360 |
| ggcaagatcg ctgactacaa ttacaagctg cccgacgatt tcaccggctg cgtgatcgcc | 420 |
| tggaactcca caatctggga tagcaaagtg ggcggcaact acaattacct gtaccgcctg | 480 |
| ttccgcaagt ccaatctgaa gccattcgag cgcgacatct ccaccgagat ctaccaggct | 540 |
| ggaagcaccc catgcaatgg agtggagggc ttcaactgct acttccccct gcagagctac | 600 |

| | |
|---|---|
| ggcttccagc caaccaacgg agtgggatac cagccataca gggtggtggt gctgtccttc | 660 |
| gagctgctgc acgctccagc taccgtgtgc ggaccaaaga agagcaccaa tctggtgaag | 720 |
| ctcgaggcat gcggtacccc cccatgccca tcatgcccag cacctgagtt cctgggggga | 780 |
| ccatcagtct tcctgttccc cccaaaaccc aaggacactc tcatgatctc ccggacccct | 840 |
| gaggtcacgt gcgtggtggt ggacgtgagc caggaagacc ccgaggtcca gttcaactgg | 900 |
| tacgtggatg gcgtggaggt gcataatgcc aagacaaagc cgcgggagga gcagttcaac | 960 |
| agcacgtacc gtgtggtcag cgtcctcacc gtcctgcacc aggactggct gaacggcaag | 1020 |
| gagtacaagt gcaaggtctc caacaaaggc ctcccgtcct ccatcgagaa aaccatctcc | 1080 |
| aaagccaaag gcagccccg agagccacag gtgtacaccc tgcccccatc ccaggaggag | 1140 |
| atgaccaaga accaggtcag cctgacctgc ctggtcaaag gcttctaccc cagcgacatc | 1200 |
| gccgtggagt gggagagcaa tgggcagccg gagaacaact acaagaccac gcctcccgtg | 1260 |
| ctggactccg acggctcctt cttcctctac agcaggctaa ccgtggacaa gagcaggtgg | 1320 |
| caggagggga atgtcttctc atgctccgtg atgcatgagg ctctgcacaa ccactacaca | 1380 |
| cagaagagcc tctccctgtc tctgggtaaa tga | 1413 |

<210> SEQ ID NO 20
<211> LENGTH: 2754
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

| | |
|---|---|
| atggacgcca tgaagagggg cctgctgctg gtgctgctgc tgtgcggcgc cgtgttcgtg | 60 |
| agcgccagcc tgactactag aacccagctg cctcctgcct atactaactc cttcacccgc | 120 |
| ggcgtgtact acccagacaa ggtgttccgc agctccgtgc tgcactccac ccaggatctg | 180 |
| ttcctgccct tcttcagcaa cgtgacctgg ttccacgcca tccacgtgag cggcaccaat | 240 |
| ggcaccaagc ggttcgacaa tcccgtgctg ccattcaacg atggcgtgta cttcgcctcc | 300 |
| accgagaaga gcaacatcat ccgcggctgg atcttcggca ccaccctgga ctccaagacc | 360 |
| cagagcctgc tgatcgtgaa caatgccacc aacgtggtca tcaaggtgtg cgagttccag | 420 |
| ttctgcaatg atccattcct gggcgtgtac taccacaaga acaataagtc ctggatggag | 480 |
| agcgagttcc gcgtgtacag ctccgccaac aattgcacct tcgagtacgt gtcccagccc | 540 |
| ttcctgatgg acctggaggg caagcagggc aatttcaaga acctgcgcga gttcgtgttc | 600 |
| aagaatatcg atggctactt caagatctac tccaagcaca ccccatcaa cctggtgcgc | 660 |
| gacctgccac agggcttcag cgccctggag ccactggtgg atctgccaat cggcatcaac | 720 |
| atcaccaggt tccagaccct gctggccctg caccgcagct acctgacccc aggcgacagc | 780 |
| tccagcggat ggaccgctgg agctgctgcc tactacgtgg gctacctgca gccccgcacc | 840 |
| ttcctgctga gtacaacga gaatggcacc atcaccgacg ccgtggattg cgccctggat | 900 |
| ccactgtccg agacaaagtg caccctgaag agcttcaccg tggagaaggg catctaccag | 960 |
| acctccaatt tccgcgtgca gccaaccgag agcatcgtgc gcttccccaa tatcaccaac | 1020 |
| ctgtgcccat tcggcgaggt gttcaacgct accaggttcg ccagcgtgta cgcttggaat | 1080 |
| cgcaagcgca tctccaactg cgtggccgac tacagcgtgc tgtacaactc cgccagcttc | 1140 |
| tccaccttca gtgctacgg cgtgtcccc accaagctga atgatctgtg cttcaccaac | 1200 |

```
gtgtacgccg atagcttcgt gatcaggggc gacgaggtgc gccagatcgc tccaggacag   1260
accggcaaga tcgctgacta caattacaag ctgcccgacg atttcaccgg ctgcgtgatc   1320
gcctggaact ccaacaatct ggatagcaaa gtgggcggca actacaatta cctgtaccgc   1380
ctgttccgca gtccaatctg aagccattcg agcgcgacat ctccaccgag atctaccagg   1440
gctggaagca ccccatgcaa tggagtggag ggcttcaact gctacttccc cctgcagagc   1500
tacggcttcc agccaaccaa cggagtggga taccagccat acagggtggt ggtgctgtcc   1560
ttcgagctgc tgcacgctcc agctaccgtg tgcggaccaa gaagagcac caatctggtg    1620 aagaacaagt gcgtgaactt caatttcaac ggcctgaccg gaaccggcgt gctgaccgag   1680
tccaacaaga agttcctgcc attccagcag ttcggaaggg acatcgctga ccaccgac    1740 gccgtgcgcg acccacagac cctggagatc ctggatatca ccccatgctc cttcggcggc   1800
gtgagcgtga tcaccccagg aaccaatacc agcaaccagg tggccgtgct gtaccaggac   1860
gtgaattgca ccgaggtgcc agtggctatc cacgctgatc agctgacccc aacctggcgc   1920
gtgtacagca ccggatccaa cgtgttccag accgcgccg gatgcctgat cggagctgag   1980
cacgtgaaca attcctacga gtgcgacatc ccaatcggag ctggaatctg cgccagctac   2040
cagacccaga ccaactcccc actcgaggca tgcggtaccc cccatgccc atcatgccca   2100 gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
ctgcccccat cccaggagga gatgaccaag aaccaggtca gcctgacctg cctggtcaaa   2520
ggcttctacc ccagcgacat cgccgtggag tgggagagca atgggcagcc ggagaacaac   2580
tacaagacca cgcctcccgt gctggactcc gacggctcct tcttcctcta cagcaggcta   2640
accgtggaca agagcaggtg gcaggagggg aatgtcttct catgctccgt gatgcatgag   2700
gctctgcaca accactacac acagaagagc ctctccctgt ctctgggtaa atga         2754
```

<210> SEQ ID NO 21
<211> LENGTH: 917
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Asp Ala Met Lys Arg Gly Leu Cys Cys Val Leu Leu Leu Cys Gly
1               5                   10                  15

Ala Val Phe Val Ser Ala Ser Leu Thr Thr Arg Thr Gln Leu Pro Pro
                20                  25                  30

Ala Tyr Thr Asn Ser Phe Thr Arg Gly Val Tyr Tyr Pro Asp Lys Val
            35                  40                  45

Phe Arg Ser Ser Val Leu His Ser Thr Gln Asp Leu Phe Leu Pro Phe
        50                  55                  60

Phe Ser Asn Val Thr Trp Phe His Ala Ile His Val Ser Gly Thr Asn
65                  70                  75                  80

```
Gly Thr Lys Arg Phe Asp Asn Pro Val Leu Pro Phe Asn Asp Gly Val
            85                  90                  95

Tyr Phe Ala Ser Thr Glu Lys Ser Asn Ile Ile Arg Gly Trp Ile Phe
       100                 105                 110

Gly Thr Thr Leu Asp Ser Lys Thr Gln Ser Leu Leu Ile Val Asn Asn
           115                 120                 125

Ala Thr Asn Val Val Ile Lys Val Cys Glu Phe Gln Phe Cys Asn Asp
130                 135                 140

Pro Phe Leu Gly Val Tyr Tyr His Lys Asn Asn Lys Ser Trp Met Glu
145                 150                 155                 160

Ser Glu Phe Arg Val Tyr Ser Ser Ala Asn Asn Cys Thr Phe Glu Tyr
                165                 170                 175

Val Ser Gln Pro Phe Leu Met Asp Leu Glu Gly Lys Gln Gly Asn Phe
            180                 185                 190

Lys Asn Leu Arg Glu Phe Val Phe Lys Asn Ile Asp Gly Tyr Phe Lys
        195                 200                 205

Ile Tyr Ser Lys His Thr Pro Ile Asn Leu Val Arg Asp Leu Pro Gln
    210                 215                 220

Gly Phe Ser Ala Leu Glu Pro Leu Val Asp Leu Pro Ile Gly Ile Asn
225                 230                 235                 240

Ile Thr Arg Phe Gln Thr Leu Leu Ala Leu His Arg Ser Tyr Leu Thr
                245                 250                 255

Pro Gly Asp Ser Ser Ser Gly Trp Thr Ala Gly Ala Ala Ala Tyr Tyr
            260                 265                 270

Val Gly Tyr Leu Gln Pro Arg Thr Phe Leu Leu Lys Tyr Asn Glu Asn
        275                 280                 285

Gly Thr Ile Thr Asp Ala Val Asp Cys Ala Leu Asp Pro Leu Ser Glu
    290                 295                 300

Thr Lys Cys Thr Leu Lys Ser Phe Thr Val Glu Lys Gly Ile Tyr Gln
305                 310                 315                 320

Thr Ser Asn Phe Arg Val Gln Pro Thr Glu Ser Ile Val Arg Phe Pro
                325                 330                 335

Asn Ile Thr Asn Leu Cys Pro Phe Gly Glu Val Phe Asn Ala Thr Arg
            340                 345                 350

Phe Ala Ser Val Tyr Ala Trp Asn Arg Lys Arg Ile Ser Asn Cys Val
        355                 360                 365

Ala Asp Tyr Ser Val Leu Tyr Asn Ser Ala Ser Phe Ser Thr Phe Lys
    370                 375                 380

Cys Tyr Gly Val Ser Pro Thr Lys Leu Asn Asp Leu Cys Phe Thr Asn
385                 390                 395                 400

Val Tyr Ala Asp Ser Phe Val Ile Arg Gly Asp Glu Val Arg Gln Ile
                405                 410                 415

Ala Pro Gly Gln Thr Gly Lys Ile Ala Asp Tyr Asn Tyr Lys Leu Pro
            420                 425                 430

Asp Asp Phe Thr Gly Cys Val Ile Ala Trp Asn Ser Asn Asn Leu Asp
        435                 440                 445

Ser Lys Val Gly Gly Asn Tyr Asn Tyr Leu Tyr Arg Leu Phe Arg Lys
    450                 455                 460

Ser Asn Leu Lys Pro Phe Glu Arg Asp Ile Ser Thr Glu Ile Tyr Gln
465                 470                 475                 480

Ala Gly Ser Thr Pro Cys Asn Gly Val Glu Gly Phe Asn Cys Tyr Phe
                485                 490                 495
```

-continued

Pro Leu Gln Ser Tyr Gly Phe Gln Pro Thr Asn Gly Val Gly Tyr Gln
              500                 505                 510

Pro Tyr Arg Val Val Leu Ser Phe Glu Leu Leu His Ala Pro Ala
        515                 520                 525

Thr Val Cys Gly Pro Lys Lys Ser Thr Asn Leu Val Lys Asn Lys Cys
        530                 535                 540

Val Asn Phe Asn Phe Asn Gly Leu Thr Gly Thr Gly Val Leu Thr Glu
545                 550                 555                 560

Ser Asn Lys Lys Phe Leu Pro Phe Gln Gln Phe Gly Arg Asp Ile Ala
                565                 570                 575

Asp Thr Thr Asp Ala Val Arg Asp Pro Gln Thr Leu Glu Ile Leu Asp
            580                 585                 590

Ile Thr Pro Cys Ser Phe Gly Gly Val Ser Val Ile Thr Pro Gly Thr
        595                 600                 605

Asn Thr Ser Asn Gln Val Ala Val Leu Tyr Gln Asp Val Asn Cys Thr
        610                 615                 620

Glu Val Pro Val Ala Ile His Ala Asp Gln Leu Thr Pro Thr Trp Arg
625                 630                 635                 640

Val Tyr Ser Thr Gly Ser Asn Val Phe Gln Thr Arg Ala Gly Cys Leu
                645                 650                 655

Ile Gly Ala Glu His Val Asn Asn Ser Tyr Glu Cys Asp Ile Pro Ile
            660                 665                 670

Gly Ala Gly Ile Cys Ala Ser Tyr Gln Thr Gln Thr Asn Ser Pro Leu
        675                 680                 685

Glu Ala Cys Gly Thr Pro Cys Pro Ser Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
        770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
        850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

```
Leu Ser Leu Gly Lys
        915
```

<210> SEQ ID NO 22
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met His His His His His His His Ser Ala Leu Ala Ala Asp Asn
1               5                   10                  15

Lys Phe Asn Lys Glu Gln Gln Asn Ala Phe Tyr Glu Ile Leu His Leu
            20                  25                  30

Pro Asn Leu Asn Glu Glu Gln Arg Asn Gly Phe Ile Gln Ser Leu Lys
        35                  40                  45

Asp Asp Pro Ser Gln Ser Ala Asn Leu Leu Ala Glu Ala Lys Lys Leu
    50                  55                  60

Asn Asp Ala Gln Ala Pro Lys Ala Leu Ile Asn Gly Gly Ser Gly Gly
65                  70                  75                  80

Ser Gly Gly Ser Gly Gly Ser Gly Gly Met Gln Ile Tyr Glu Gly
                85                  90                  95

Lys Leu Thr Ala Glu Gly Leu Arg Phe Gly Ile Val Ala Ser Arg Phe
            100                 105                 110

Asn His Ala Leu Val Asp Arg Leu Val Glu Gly Ala Ile Asp Ala Ile
        115                 120                 125

Val Arg His Gly Gly Arg Glu Glu Asp Ile Thr Leu Val Arg Val Pro
    130                 135                 140

Gly Ser Trp Glu Ile Pro Val Ala Ala Gly Glu Leu Ala Arg Lys Glu
145                 150                 155                 160

Asp Ile Asp Ala Val Ile Ala Ile Gly Val Leu Ile Arg Gly Ala Thr
                165                 170                 175

Pro His Phe Asp Tyr Ile Ala Ser Glu Val Ser Lys Gly Leu Ala Gln
            180                 185                 190

Leu Ser Leu Glu Leu Arg Lys Pro Ile Thr Phe Gly Val Ile Thr Ala
        195                 200                 205

Asp Thr Leu Glu Gln Ala Ile Glu Arg Ala Gly Thr Lys His Gly Asn
    210                 215                 220

Lys Gly Trp Glu Ala Ala Leu Ser Ala Ile Glu Met Ala Asn Leu Phe
225                 230                 235                 240

Lys Ser Leu Arg
```

<210> SEQ ID NO 23
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atgcaccacc accaccacca ccaccattct gctctcgctg ctgataacaa gttcaacaag     60
gaacagcaga acgccttcta cgagatcctg cacctgccta acctgaacga ggaacagaga    120
aacggcttca tccagtccct gaaggacgat cctagccaga gcgctaatct gctggccgag    180
gccaagaagc tgaacgacgc ccaggcccct aaggccctga tcaacggagg aagcggcgga    240
```

```
tctggcggca gcggaggcag cggcggcggc atgcagatct acgagggcaa gctgaccgcc    300
gagggcctga ggtttggcat cgtggccagc agatttaacc acgccctggt cgacagactg    360
gtggaaggcg ctattgacgc cattgtgcgg cacggcggaa gagaggaaga tatcaccctg    420
gtgcgggtgc caggcagctg ggagatcccc gtggccgccg cgagctggc cagaaaagag    480 gacatcgatg ccgtgatcgc catcggcgtt ctgatccggg cgccaccc tcacttcgac      540 tacatcgcca gcgaggtgtc taagggcctg gctcagctga gcctggaact gagaaagccc    600
atcaccttcg gcgtgatcac agccgacacc ctggaacaag ccatcgagag agccggtaca    660
aagcatggaa ataaaggctg ggaagccgct ctcagcgcca tcgagatggc caatctgttc    720
aagagcctgc ggtga                                                      735
```

```
<210> SEQ ID NO 24
<211> LENGTH: 237
<212> TYPE: PRT
<213> ORGANISM: Severe acute respiratory syndrome coronavirus 2

<400> SEQUENCE: 24
```

```
Glu Lys Gly Ile Tyr Gln Thr Ser Asn Phe Arg Val Gln Pro Thr Glu
1               5                   10                  15

Ser Ile Val Arg Phe Pro Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Lys Ser Thr Asn
    210                 215                 220

Leu Val Lys Asn Lys Cys Val Asn Phe Asn Phe Asn Gly
225                 230                 235
```

```
<210> SEQ ID NO 25
<211> LENGTH: 197
<212> TYPE: PRT
<213> ORGANISM: Severe acute respiratory syndrome coronavirus 2
```

<400> SEQUENCE: 25

Phe Pro Asn Ile Thr Asn Leu Cys Pro Phe Gly Glu Val Phe Asn Ala
1               5                   10                  15

Thr Arg Phe Ala Ser Val Tyr Ala Trp Asn Arg Lys Arg Ile Ser Asn
            20                  25                  30

Cys Val Ala Asp Tyr Ser Val Leu Tyr Asn Ser Ala Ser Phe Ser Thr
        35                  40                  45

Phe Lys Cys Tyr Gly Val Ser Pro Thr Lys Leu Asn Asp Leu Cys Phe
    50                  55                  60

Thr Asn Val Tyr Ala Asp Ser Phe Val Ile Arg Gly Asp Glu Val Arg
65                  70                  75                  80

Gln Ile Ala Pro Gly Gln Thr Gly Lys Ile Ala Asp Tyr Asn Tyr Lys
                85                  90                  95

Leu Pro Asp Asp Phe Thr Gly Cys Val Ile Ala Trp Asn Ser Asn Asn
            100                 105                 110

Leu Asp Ser Lys Val Gly Gly Asn Tyr Asn Tyr Leu Tyr Arg Leu Phe
        115                 120                 125

Arg Lys Ser Asn Leu Lys Pro Phe Glu Arg Asp Ile Ser Thr Glu Ile
130                 135                 140

Tyr Gln Ala Gly Ser Thr Pro Cys Asn Gly Val Glu Gly Phe Asn Cys
145                 150                 155                 160

Tyr Phe Pro Leu Gln Ser Tyr Gly Phe Gln Pro Thr Asn Gly Val Gly
                165                 170                 175

Tyr Gln Pro Tyr Arg Val Val Val Leu Ser Phe Glu Leu Leu His Ala
            180                 185                 190

Pro Ala Thr Val Cys
        195

<210> SEQ ID NO 26
<211> LENGTH: 10
<212> TYPE: PRT
<213> ORGANISM: Severe acute respiratory syndrome coronavirus 2

<400> SEQUENCE: 26

Arg Val Gln Pro Thr Glu Ser Ile Val Arg
1               5                   10

<210> SEQ ID NO 27
<211> LENGTH: 10
<212> TYPE: PRT
<213> ORGANISM: Severe acute respiratory syndrome coronavirus 2

<400> SEQUENCE: 27

Gly Pro Lys Lys Ser Thr Asn Leu Val Lys
1               5                   10

<210> SEQ ID NO 28
<211> LENGTH: 10
<212> TYPE: PRT
<213> ORGANISM: Severe acute respiratory syndrome coronavirus 2

<400> SEQUENCE: 28

Glu Lys Gly Ile Tyr Gln Thr Ser Asn Phe
1               5                   10

<210> SEQ ID NO 29
<211> LENGTH: 10
<212> TYPE: PRT

```
<213> ORGANISM: Severe acute respiratory syndrome coronavirus 2

<400> SEQUENCE: 29

Asn Lys Cys Val Asn Phe Asn Phe Asn Gly
1               5                   10

<210> SEQ ID NO 30
<211> LENGTH: 154
<212> TYPE: PRT
<213> ORGANISM: Aquifex aeolicus

<400> SEQUENCE: 30

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asn Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 31
<211> LENGTH: 7
<212> TYPE: PRT
<213> ORGANISM: Severe acute respiratory syndrome coronavirus 2

<400> SEQUENCE: 31

Lys Ser Thr Asn Leu Val Lys
1               5

<210> SEQ ID NO 32
<211> LENGTH: 6
<212> TYPE: PRT
<213> ORGANISM: Severe acute respiratory syndrome coronavirus 2

<400> SEQUENCE: 32

Ser Thr Asn Leu Val Lys
1               5

<210> SEQ ID NO 33
<211> LENGTH: 7
<212> TYPE: PRT
<213> ORGANISM: Severe acute respiratory syndrome coronavirus 2

<400> SEQUENCE: 33

Asn Lys Cys Val Asn Phe Ser
1               5
```

```
<210> SEQ ID NO 34
<211> LENGTH: 6
<212> TYPE: PRT
<213> ORGANISM: Severe acute respiratory syndrome coronavirus 2

<400> SEQUENCE: 34

Asn Lys Cys Val Asn Phe
1               5

<210> SEQ ID NO 35
<211> LENGTH: 9
<212> TYPE: PRT
<213> ORGANISM: Severe acute respiratory syndrome coronavirus 2

<400> SEQUENCE: 35

Val Gln Pro Thr Glu Ser Ile Val Arg
1               5

<210> SEQ ID NO 36
<211> LENGTH: 8
<212> TYPE: PRT
<213> ORGANISM: Severe acute respiratory syndrome coronavirus 2

<400> SEQUENCE: 36

Gln Pro Thr Glu Ser Ile Val Arg
1               5

<210> SEQ ID NO 37
<211> LENGTH: 7
<212> TYPE: PRT
<213> ORGANISM: Severe acute respiratory syndrome coronavirus 2

<400> SEQUENCE: 37

Pro Thr Glu Ser Ile Val Arg
1               5

<210> SEQ ID NO 38
<211> LENGTH: 6
<212> TYPE: PRT
<213> ORGANISM: Severe acute respiratory syndrome coronavirus 2

<400> SEQUENCE: 38

Thr Glu Ser Ile Val Arg
1               5

<210> SEQ ID NO 39
<211> LENGTH: 5
<212> TYPE: PRT
<213> ORGANISM: Severe acute respiratory syndrome coronavirus 2

<400> SEQUENCE: 39

Glu Ser Ile Val Arg
1               5

<210> SEQ ID NO 40
<211> LENGTH: 4
<212> TYPE: PRT
<213> ORGANISM: Severe acute respiratory syndrome coronavirus 2

<400> SEQUENCE: 40

Ser Ile Val Arg
1

<210> SEQ ID NO 41
<211> LENGTH: 9
```

```
<212> TYPE: PRT
<213> ORGANISM: Severe acute respiratory syndrome coronavirus 2

<400> SEQUENCE: 41

Gly Pro Lys Lys Ser Thr Asn Leu Val
1               5

<210> SEQ ID NO 42
<211> LENGTH: 8
<212> TYPE: PRT
<213> ORGANISM: Severe acute respiratory syndrome coronavirus 2

<400> SEQUENCE: 42

Gly Pro Lys Lys Ser Thr Asn Leu
1               5

<210> SEQ ID NO 43
<211> LENGTH: 7
<212> TYPE: PRT
<213> ORGANISM: Severe acute respiratory syndrome coronavirus 2

<400> SEQUENCE: 43

Gly Pro Lys Lys Ser Thr Asn
1               5

<210> SEQ ID NO 44
<211> LENGTH: 6
<212> TYPE: PRT
<213> ORGANISM: Severe acute respiratory syndrome coronavirus 2

<400> SEQUENCE: 44

Gly Pro Lys Lys Ser Thr
1               5

<210> SEQ ID NO 45
<211> LENGTH: 5
<212> TYPE: PRT
<213> ORGANISM: Severe acute respiratory syndrome coronavirus 2

<400> SEQUENCE: 45

Gly Pro Lys Lys Ser
1               5

<210> SEQ ID NO 46
<211> LENGTH: 4
<212> TYPE: PRT
<213> ORGANISM: Severe acute respiratory syndrome coronavirus 2

<400> SEQUENCE: 46

Gly Pro Lys Lys
1

<210> SEQ ID NO 47
<211> LENGTH: 9
<212> TYPE: PRT
<213> ORGANISM: Severe acute respiratory syndrome coronavirus 2

<400> SEQUENCE: 47

Lys Gly Ile Tyr Gln Thr Ser Asn Phe
1               5

<210> SEQ ID NO 48
<211> LENGTH: 8
<212> TYPE: PRT
<213> ORGANISM: Severe acute respiratory syndrome coronavirus 2
```

```
<400> SEQUENCE: 48

Gly Ile Tyr Gln Thr Ser Asn Phe
1               5

<210> SEQ ID NO 49
<211> LENGTH: 7
<212> TYPE: PRT
<213> ORGANISM: Severe acute respiratory syndrome coronavirus 2

<400> SEQUENCE: 49

Ile Tyr Gln Thr Ser Asn Phe
1               5

<210> SEQ ID NO 50
<211> LENGTH: 6
<212> TYPE: PRT
<213> ORGANISM: Severe acute respiratory syndrome coronavirus 2

<400> SEQUENCE: 50

Tyr Gln Thr Ser Asn Phe
1               5

<210> SEQ ID NO 51
<211> LENGTH: 5
<212> TYPE: PRT
<213> ORGANISM: Severe acute respiratory syndrome coronavirus 2

<400> SEQUENCE: 51

Gln Thr Ser Asn Phe
1               5

<210> SEQ ID NO 52
<211> LENGTH: 4
<212> TYPE: PRT
<213> ORGANISM: Severe acute respiratory syndrome coronavirus 2

<400> SEQUENCE: 52

Thr Ser Asn Phe
1

<210> SEQ ID NO 53
<211> LENGTH: 9
<212> TYPE: PRT
<213> ORGANISM: Severe acute respiratory syndrome coronavirus 2

<400> SEQUENCE: 53

Asn Lys Cys Val Asn Phe Asn Phe Asn
1               5

<210> SEQ ID NO 54
<211> LENGTH: 8
<212> TYPE: PRT
<213> ORGANISM: Severe acute respiratory syndrome coronavirus 2

<400> SEQUENCE: 54

Asn Lys Cys Val Asn Phe Asn Phe
1               5

<210> SEQ ID NO 55
<211> LENGTH: 7
<212> TYPE: PRT
<213> ORGANISM: Severe acute respiratory syndrome coronavirus 2
```

```
<400> SEQUENCE: 55

Asn Lys Cys Val Asn Phe Asn
1               5

<210> SEQ ID NO 56
<211> LENGTH: 5
<212> TYPE: PRT
<213> ORGANISM: Severe acute respiratory syndrome coronavirus 2

<400> SEQUENCE: 56

Asn Lys Cys Val Asn
1               5

<210> SEQ ID NO 57
<211> LENGTH: 4
<212> TYPE: PRT
<213> ORGANISM: Severe acute respiratory syndrome coronavirus 2

<400> SEQUENCE: 57

Asn Lys Cys Val
1
```